(12) United States Patent
Han et al.

(10) Patent No.: US 11,191,775 B2
(45) Date of Patent: Dec. 7, 2021

(54) PAPD5 AND PAPD7 INHIBITORS FOR TREATING A HEPATITIS B INFECTION

(71) Applicant: HOFFMANN-LA ROCHE INC., Little Falls, NJ (US)

(72) Inventors: Xingchun Han, Shanghai (CN); Hassan Javanbakht, San Francisco, CA (US); Henrik Mueller, Basel (CH); Yongguang Wang, Shanghai (CN); Song Yang, Shanghai (CN)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/310,765

(22) PCT Filed: Jun. 19, 2017

(86) PCT No.: PCT/EP2017/064981
§ 371 (c)(1),
(2) Date: Dec. 17, 2018

(87) PCT Pub. No.: WO2017/216391
PCT Pub. Date: Dec. 21, 2017

(65) Prior Publication Data
US 2019/0194768 A1    Jun. 27, 2019

(30) Foreign Application Priority Data

Jun. 17, 2016   (EP) .................................. 16175045

(51) Int. Cl.
| | | |
|---|---|---|
| *C07K 16/40* | (2006.01) | |
| *A61K 31/20* | (2006.01) | |
| *A61K 31/4745* | (2006.01) | |
| *A61K 31/7125* | (2006.01) | |
| *C12Q 1/6883* | (2018.01) | |
| *C12N 15/113* | (2010.01) | |
| *C12Q 1/70* | (2006.01) | |
| *A61P 31/14* | (2006.01) | |
| *A61K 31/519* | (2006.01) | |
| *A61P 31/20* | (2006.01) | |

(52) U.S. Cl.
CPC ...... *A61K 31/7125* (2013.01); *A61K 31/4745* (2013.01); *A61K 31/519* (2013.01); *A61P 31/14* (2018.01); *A61P 31/20* (2018.01); *C07K 16/40* (2013.01); *C12N 15/113* (2013.01); *C12N 15/1137* (2013.01); *C12Q 1/6883* (2013.01); *C12Q 1/706* (2013.01); *C07K 2317/732* (2013.01); *C12N 2310/14* (2013.01)

(58) Field of Classification Search
CPC ................................................. A61K 31/7125
See application file for complete search history.

(56) References Cited

U.S. PATENT DOCUMENTS

| | | |
|---|---|---|
| 4,711,955 A | 12/1987 | Ward et al. |
| 5,525,711 A | 6/1996 | Hawkins et al. |
| 5,792,608 A | 8/1998 | Swaminathan et al. |
| 5,885,968 A | 3/1999 | Biessen et al. |
| 8,090,542 B2 | 1/2012 | Khvorova et al. |
| 8,349,809 B2 | 1/2013 | Brown |
| 8,513,207 B2 | 8/2013 | Brown |
| 9,458,153 B2 | 10/2016 | Han |
| 10,093,671 B2 * | 10/2018 | Han ..................... C07D 471/04 |
| 10,953,034 B2 | 3/2021 | Kammler |
| 2004/0157780 A1 | 8/2004 | Grey |
| 2005/0272080 A1 | 12/2005 | Palma |
| 2006/0257851 A1 | 11/2006 | Bentwich |
| 2010/0173974 A1 | 7/2010 | Brown |
| 2011/0118337 A1 | 5/2011 | Chau et al. |
| 2012/0040460 A1 | 2/2012 | Rigoutsos et al. |

(Continued)

FOREIGN PATENT DOCUMENTS

| | | |
|---|---|---|
| CL | 201803561 | 12/2018 |
| CL | 201900945 | 4/2020 |

(Continued)

OTHER PUBLICATIONS

Mangos, MM et al., "Efficient RNase H-Directed Cleavage of RNA Promoted by Antisense DNA or 2'F-ANA Constructs Containing Acyclic Nucleotide Inserts," J. Am. Chem. Soc., 2003, vol. 125(3), pp. 654-661, 8 pages.

Manoharan, M., "Oligonucleotide Conjugates in Antisense Technology," Antisense Drug Technology, Marcel Dekker, Inc., 2001, Ch. 16, pp. 391-469, 81 pages.

Marcellin et al., "Peginterferon Alfa-2a Alone, Lamivudine Alone, and the Two in Combination in Patients with HBeAg-Negative Chronic Hepatitis B," N. Engl. J. Med., 2004, vol. 351:12, pp. 1206-1217, 12 pages.

(Continued)

*Primary Examiner* — Bao Q Li
(74) *Attorney, Agent, or Firm* — Holland & Hart LLP

(57) ABSTRACT

The present invention relates to a method for identifying a compound that prevents, ameliorates and/or inhibits a hepatitis B virus (HBV) infection, wherein a compound that (i) reduces the expression and/or activity of PAP associated domain containing 5 (PAPD5) and/or PAP associated domain containing 7 (PAPD7); and/or (ii) binds to PAPD5 and/or PAPD7 and inhibits 5 propagation of HBV; is identified as a compound that prevents, ameliorates and/or inhibits a HBV infection. The invention also provides for an inhibitor of PAPD5 and/or PAPD7 for use in treating and/or preventing a HBV infection; as well as a combined preparation comprising an inhibitor of PAPD5 and an inhibitor of PAPD7 for simultaneous or sequential use in the treatment or prevention of a HBV infection. Also comprised in the present invention is a 10 pharmaceutical composition for use in the treatment and/or prevention of a HBV infection, and a method for monitoring the therapeutic success during the treatment of a HBV infection.

8 Claims, 7 Drawing Sheets

Specification includes a Sequence Listing.

(56) References Cited

U.S. PATENT DOCUMENTS

| | | | |
|---|---|---|---|
| 2017/0023568 A1 | 8/2017 | Ouardi | |
| 2019/0111073 A1 | 4/2019 | Kammler et al. | |
| 2019/0194768 A1 | 6/2019 | Han | |
| 2019/0211339 A1 | 7/2019 | Agarwal et al. | |
| 2019/0216846 A1 | 7/2019 | Javanbakht | |
| 2020/0147123 A1 | 5/2020 | Kammler et al. | |

FOREIGN PATENT DOCUMENTS

| | | | |
|---|---|---|---|
| CL | 202001638 | | 6/2020 |
| CN | 101541977 | A | 9/2009 |
| CN | 104080481 | A | 10/2014 |
| CN | 109328237 | | 2/2019 |
| EP | 0302175 | A2 | 2/1989 |
| EP | 1013661 | A1 | 6/2000 |
| EP | 1152009 | A1 | 7/2001 |
| EP | 1752536 | A1 | 12/2005 |
| EP | 2213738 | A2 | 8/2010 |
| EP | 221373 | | 10/2012 |
| EP | 2890789 | | 7/2016 |
| JP | 2005116204 | A1 | 12/2005 |
| JP | 2017515862 | | 6/2017 |
| JP | 2017557384 | | 6/2018 |
| JP | 2019-523649 | | 8/2019 |
| WO | 1993007883 | | 4/1993 |
| WO | 1998039352 | A1 | 9/1998 |
| WO | 1999014226 | A2 | 3/1999 |
| WO | 2000047599 | A1 | 8/2000 |
| WO | 2000066604 | A2 | 11/2000 |
| WO | 2001023613 | A2 | 4/2001 |
| WO | 03022987 | A2 | 3/2003 |
| WO | 2004046160 | A2 | 6/2004 |
| WO | 2005014806 | | 2/2005 |
| WO | 2005014806 | A2 | 2/2005 |
| WO | 2007031091 | A2 | 3/2007 |
| WO | 2007090071 | A2 | 8/2007 |
| WO | 2007106407 | A2 | 9/2007 |
| WO | 2007134181 | A2 | 11/2007 |
| WO | 2007146511 | A2 | 12/2007 |
| WO | 2008049085 | A1 | 4/2008 |
| WO | 2008082730 | A2 | 7/2008 |
| WO | 2008113832 | A2 | 9/2008 |
| WO | 2008150729 | A2 | 12/2008 |
| WO | 2008154401 | A2 | 12/2008 |
| WO | 2009006478 | A2 | 1/2009 |
| WO | 2009067647 | A1 | 5/2009 |
| WO | 2009090182 | A1 | 7/2009 |
| WO | 2009124238 | A1 | 10/2009 |
| WO | 2010036698 | A1 | 4/2010 |
| WO | 2010040571 | A2 | 4/2010 |
| WO | 2010077578 | A1 | 7/2010 |
| WO | 2010093788 | A2 | 8/2010 |
| WO | 2011017521 | A2 | 2/2011 |
| WO | 2011108699 | A1 | 9/2011 |
| WO | 2011156202 | A1 | 12/2011 |
| WO | 2012024170 | A2 | 2/2012 |
| WO | 2012055362 | A1 | 5/2012 |
| WO | 2012109395 | A1 | 8/2012 |
| WO | 2012145697 | A1 | 10/2012 |
| WO | 2013003520 | A1 | 1/2013 |
| WO | 2013022984 | A1 | 2/2013 |
| WO | 2013033230 | A1 | 3/2013 |
| WO | 2013036868 | A1 | 3/2013 |
| WO | 2013113501 | A1 | 8/2013 |
| WO | 2013154798 | A1 | 10/2013 |
| WO | 2013159109 | A1 | 10/2013 |
| WO | 2013166264 | A2 | 11/2013 |
| WO | 2014012081 | A2 | 1/2014 |
| WO | 2014036429 | A1 | 3/2014 |
| WO | 2014076195 | A1 | 5/2014 |
| WO | 2014076196 | A1 | 5/2014 |
| WO | 2014179620 | A1 | 11/2014 |
| WO | 2014179629 | A2 | 11/2014 |
| WO | 2014207232 | A1 | 12/2014 |
| WO | 2015031694 | A2 | 3/2015 |
| WO | 2015113922 | A1 | 8/2015 |
| WO | 2015113990 | A1 | 8/2015 |
| WO | 2015173164 | A1 | 11/2015 |
| WO | 2015173208 | A2 | 11/2015 |
| WO | 2016055601 | A1 | 4/2016 |
| WO | 2016079181 | A1 | 5/2016 |
| WO | 2016051116 | | 7/2016 |
| WO | 2016127002 | A1 | 8/2016 |
| WO | 2016177655 | A1 | 11/2016 |
| WO | 2017015175 | A1 | 1/2017 |
| WO | 2017027350 | A2 | 2/2017 |
| WO | 2017066712 | A2 | 4/2017 |
| WO | 2017178656 | A1 | 10/2017 |
| WO | 2017216390 | A1 | 12/2017 |
| WO | 2017216391 | A1 | 12/2017 |
| WO | 2018059718 | A1 | 4/2018 |
| WO | 2019145543 | A1 | 8/2019 |

OTHER PUBLICATIONS

McTigue, PM et al., "Sequence-Dependent Thermodynamic Parameters for Locked Nucleic Acid (LNA)-DNA Duplex Formation," Biochemistry, 2004, vol. 43(18), pp. 5388-5405, 18 pages.

Mergny, JL et al., "Analysis of Thermal Melting Curves," Oligonucleotides, 2003, vol. 13(6), pp. 515-537, 23 pages.

Milich, DR, "Influence of T-helper cell subsets and crossregulation in hepatitis B virus infection," Journal of Viral Hepatitis, 1997, vol. 4 (suppl 2), pp. 48-59, 12 pages.

Milich et al., "The Secreted Hepatitis B Precore Antigen Can Modulate the Immune Response to the Nucleocapsid: A Mechanism for Persistence," 1998, J. Immunol. 160, pp. 2013-2021, 10 pages.

Mitsuoka, Y et al., "A bridged nucleic acid, 2',4'-BNACOC: synthesis of fully modified oligonucleotides bearing thymine, 5-methylcytosine, adenine and guanine 2',4'-BNACOC monomers and RNA-selective nucleic-acid recognition," Nucleic Acids Research, 2009, vol. 37, No. 4, pp. 1225-1238, 14 pages.

Morita, K. et al., "2'-O,4'C-ethylene-bridged nucleic acids (ENA): highly nuclease-resistant and thermodynamically stable oligonucleotides for antisense drug," Bioorganic & Medicinal Chemistry Letters, 2002, vol. 12:1, pp. 73-76, 4 pages.

Mueller et al., "PAPD5/7 are novel host factors that are required for Hepatitis B virus RNA stabilization," Hepatology, 2018, XP-002787333, pp. 1527-3350.

Nayersina, R et al, "HLA A2 restricted cytotoxic T lymphocyte responses to multiple hepatitis B surface antigen epitopes during hepatitis B virus infection," Journal of Immunology, 1993, vol. 150:10, pp. 4659-4671, 14 pages.

Ogami, K et al., "Molecular cloning and characterization of a novel isoform of the non-canonical poly(A) polymerase PAPD7", Biochemical and Biophysical Research Communications, 2013, 432.1, pp. 135-140, 6 pages.

OP Den Brouw et al., "Hepatitis B virus surface antigen impairs myeloid dendritic cellfunction: a possible immune escape mechanism of hepatitis B virus," Immunology, 2009b, 126, pp. 280-289, 10 pages.

Rammelt, C et al, "PAPD5, a noncanonical poly(A) polymerase with an unusual RNA-binding motif", RNA, 2011, vol. 17, pp. 1737-1746, 10 pages.

RA Palma et al., Database entry: GC056445, Aug. 12, 2005 (Aug. 12, 2005), pp. 1-1, XP055404289, Retrieved from the Internet: URL:file:///C:/Users/TL23249/Documents/Downloads/EM_PAT_GC056445.pdf [retrieved on Sep. 6, 2017], 1 page.

Rukov, JL et al., "Dissecting the target specificity of RNase H recruiting oligonucleotides using massively parallel reporter analysis of short RNA motifs," Nucleic Acids Research, 2015, vol. 43:17, pp. 8476-8487, 12 pages.

Santalucia, J Jr., "Unified view of polymer, dumbbell, and oligonucleotide DNA nearest-neighbor thermodynamics," Proc. National Academy Science USA., 1998, vol. 95:4, pp. 1460-1465, 6 pages.

Schulze et al., "Detection of CD4+ T Cell Responses in Patients with acute HCV Infection Irrespective of Clinical Outcome," Hepatology, 463, 2007, 1 page.

(56) References Cited

OTHER PUBLICATIONS

Sells, MA et al., "Production of hepatitis B virus particles in Hep G2 cells transfected with cloned hepatitis B virus DNA," Proceedings of National Academy Science USA, 1987, vol. 84:4, pp. 1005-1009, 5 pages.
Seth, PP et al.,"Synthesis and Biophysical Evaluation of 2',4'-Constrained 2'O-Methoxyethyl and 2',4'-Constrained 2'O-Ethyl Nucleic Acid Analogues," J. Org. Chem., 2010, vol. 75:5, pp. 1569-1581, 7 pages.
Shi, CC et al., "Hepatitis B virus suppresses the functional interaction between natural killer cells and plasmacytoid dendritic cells," Journal Viral Hepatitas, 2012, vol. 19:2, e26-e33, 8 pages.
Shin et al., "Prediction of response to entecavir therapy in patients withHBeAg-positive chronic hepatitis B based on on-treatmentHBsAg, HBeAg and HBV DNA levels," Journal of Viral Hepatitis, 2012, 19, pp. 724-731, 8 pages.
Sugimoto, N et al., "Thermodynamic Parameters to Predict Stability of RNA/DNA Hybrid Duplexes," Biochemistry, 1995, vol. 34:35, pp. 11211-11216, 6 pages.
Tavis John E. et al., "The hepatitis B virus ribonuclease H as a drug target," Antiviral Research, vol. 118, 2015, pp. 132-138, 8 pages.
Thompson, JD et al., "CLUSTAL W: improving the sensitivity of progressive multiple sequence alignment through sequence weighting, position-specific gap penalties and weight matrix choice," Nucleic Acids Res., 1994, vol. 22(22), pp. 4673-4680, 8 pages.
Uhlmann, E, "Recent advances in the medicinal chemistry of antisense olignonucleotides," Current Opinion in Drug Discovery & Development, 2000, vol. 3:2, pp. 203-213, 12 pages.
Vester, B et al., "Chemically modified oligonucleotides with efficient RNase H response," Bioorganic & Medicinal Chemistry Letters, 2008, vol. 18:7, pp. 2296-2300, 5 pages.
Walsh, R et al., "Targeting the hepatits B virus procore antigen with a novel IgNAR singel variable domain intrabody," Virology, 2011, vol. 411:1, pp. 132-141, 10 pages.
Ward, ES et al., "Binding activities of a repertoire of single immunoglobulin variable domains secreted from *Escherichia coli*," Nature, 1989, vol. 341, pp. 544-546, 3 pages.
Wieland, SF et al., "Stealth and Cunning: Hepatitis B and Hepatitis C Viruses," J Virol, 2005, 79, pp. 9369-9680, 12 pages.
Winther, TH et al., "Circulating MicroRNAs in Plasma of Hepatitis B e Antigent Positive Children Reveal Liver-Specifc Target Genes", International Journal of Hepatology, 2014, article ID791045, pp. 1-10, 10 pages.
Woltman et al., Hepatitis B Virus Lacks Immune Activating Capacity, but Actively Inhibits Plasmacytoid Dendritic Cell Function; PLoS One, Jun. 2011, e15324, 14 pages.
Wooddell, CI et al., "RNAi-based treatment of chronically infected patients and chimpanzees reveals that integrated hepatitis B virus DNA is a source of HBsAg," Science Translational Medicine, 2017, vol. 9, No. 409, eaan0241, 12 pages.
Wu Q et al., "EM_EST:EH352838; SV 1; linear; mRNA; EST; HUM; 105 BP," Mar. 2, 2007; Retrieved from the Internet: URL:file:///ibis.internal.epo.org/exam/dbfetch.jsp?id=EM_EST:EH352838 [retrieved on Jan. 15, 2020], 1 page.
Yan et al., "Molecular Determinants of Hepatitis B and D Virus Entry Restriction in Mouse Sodium Taurocholate Cotransporting Polypeptide," J Virol, 87, 2013, pp. 7977-7991, 8 pages.
Yang, D et al., "A mouse model for HBV immunotolerance and immunotherapy," Cellular & Molecular Immunology, 2014, vol. 11, pp. 71-78, 8 pages.
Zhou, T et al., HBsAg mRNA degradation induced by a dihydroquinolizinone compound depends on the HBV posttranscription regulatory element, Antiviral Research, 2018, vol. 149, pp. 191-201, 11 pages.
N.N: Database entry GS _ NUC ALERT:W02015031694.237191, Mar. 5, 2015 (Mar. 5, 2015), pp. 1-1, XP055404257, Retrieved from the Internet: URL:www C:/Users/TL23249/Documents/Downloads/GS_NUC_ALERT_WO2015031694.pdf [retrieved on Sep. 6, 2017], 1 page.
N.N: Database entry: ATJ17241, Sep. 20, 2007 (Sep. 20, 2007), pp. 1-1, XP055404262, Retrieved from the Internet: URL:file:///C:/Users/TL23249/Documents/Downloads/GSN_ATJ17241.pdt [retrieved on Sep. 6, 2017], 1 page.
N.N: "Database entry: GZ986077", Jun. 4, 2013, XP05544295, Retrieved from the Internet: URL: https://www.ncbi.nlm.nih.gov/pubmed/ [retrieved on Sep. 6, 2017].
N.N: Database entry: miRTarBase—targets for hsa-mir-192-5p, Jun. 3, 2014 (Jun. 3, 2014), XP055404326, Retrieved from the Internet: URL:file:///C:/Users/TL23249/Documents/Downloads/miRNA-Target Interaction Search Results.pdf [retrieved on Sep. 6, 2017], 6 pages.
N.N: Database entry: mRNA—"EM_EST:AW015126; SV 1; linear; mRNA; EST; HUM; 244 BP," Sep. 13, 1999; Retrieved from the Internet: URL:file:///ibis.internal.epo.org/exam/dbfetch.jsp?id=EM_EST:AW015126 [retrieved on Jan. 15, 2020], 1 page.
Database EMBL, Aug. 18, 2010, (Aug. 18, 2010) Sequence 593709 from Patent EP2213738., XP002787331, retrieved from EBI accession No. EM PAT:HD716993 Database accession No. HD716993 sequence, 1 page.
Database EMBL, Apr. 19, 2011, (Apr. 19, 2011) WO 2005116204-A/507823: Double strand polynucleotides generating RNA interference., XP002787332, retrieved from EBI accession No. EM PAT:FZ101298 Database accession No. FZ101298 sequence.
Database EMBL, Aug. 18, 2011, (Aug. 18, 2011) 11 Sequence 447635 from Patent EP2213738. II XP002787330, retrieved from EBI accession No. EM PAT:HD570919 Database accession No. HD570919 sequence, 1 page.
PCT International Search Report for PCT International Patent Application No. PCT/EP2017/064980, dated Oct. 2, 2017.
Altschul, SF et al., "Basic Local Alignment Search Tool," J Mol Biol, 1990, vol. 215, pp. 403-410, 8 pages.
Altschul, SF, "A Protein Alignment Scoring System Sensitive at All Evolutionary Distances," Journal Molecular Evolution, 1993, vol. 36, pp. 290-300; 11 pages.
Altschul, SF et al., "Gapped BLAST and PSI-BLAST: a new generation of protein database search programs," Nucleic Acids Research, 1997, vol. 25:17, pp. 3389-3402, 14 pages.
Ansel, HC et al., "Pharmaceutical Dosage Forms and Drug Delivery Systems," 1995, Williams & Wilkins, pp. xi-xii, 105-116, 194-200, 497-514, cover pages, 41 pages.
Bartel et al., "Cellular interactions in Development: A practical approach." Oxford University Press, pp. 153-179, 28 pages.
Bastin, RJ et al., "Salt Selection and Optimisation Procedures for Pharmaceutical New Chemical Entities," Organic Process Research & Development, 2000, vol. 4, pp. 427-435, 9 pages.
Bergstrom DE, "Unnatural Nucleosides with Unusual Base Pairing Properties," Current Protocols in Nucleic Acid Chemistry, 2001, Suppl. 5, pp. 1.4.1-1.4.13, 13 pages.
Biessen, E.A.L. et al., "Synthesis of Cluster Galactosides with High Affinity for the Hepatic Asialoglycoprotein Receptor," J. Med. Chem., 1995, vol. 38(9), pp. 1538-1546, 9 pages.
Biessen, E.A.L. et al., "Receptor-Dependent Cell Specific Delivery of Antisense Oligonucleotides," Developments in Cardiovascular Medicine, 1999, 24, pp. 285-299, 15 pages.
Block, Timothy M. et al., "Chronic hepatitis B: A wave of new therapies on the horizon," Antiviral Research, Elsevier BV, NL, vol. 121, 2015, pp. 69-81, 14 pages.
Brutlag et al., "Improved sensitivity of biological sequence database searches," 1990, vol. 6:3, pp. 237-245, 9 pages.
Buster, EH et al., "Peginterferon alpha-2b is safe and effective in HBeAg-positive chronic hepatitis B patients with advanced fibrosis," Hepatology, 2007, vol. 46, No. 2, pp. 388-394, 7 pages.
Buster et al., "Withdrawal Flares After Treatment with Peginterferon Alpha-2b alone or in Combination with Lamivudine in HBeAg-Positive Chronic Hepatitis B," Hepatology, 2007, 46, 1 page.
Cahn, RS, et al., "Specification of Molecular Chirality," Angewandte Chemie International Edition, 1966, vol. 5, No. 4, pp. 385-415, 31 pages.
Caruthers, MH et al., "Chemical Synthesis of Deoxyoligonucleotides by the Phosphoramidite Method," Methods in Enzymology, 1987, vol. 154, pp. 287-313, 27 pages.

(56) References Cited

OTHER PUBLICATIONS

Chang, Mei-Hwei, "Hepatitis B virus infection," Elsevier, Seminars in Fetal Neonatal Medicine, 2007, vol. 12, pp. 160-167, 8 pages.
Chen et al., "Immune Tolerance Split between Hepatitis B Virus Precore and Core Proteins," Journal of Virology, 2005, 79:5, pp. 3016-3027, 12 pages.
Chidley, C. et al., "A yeast-based screen reveals that sulfasalazine inhibits tetrahydrobiopterin biosynthesis", Nature Chemical Biology, 2011, vol. 7, pp. 375-383, 9 pages.
Deleavey, GF et al., "Designing Chemically Modified Oligonucleotides for Targeted Gene Silencing," Chemistry and Biology, 2012, vol. 19(8), pp. 937-954, 18 pages.
Duff, RJ et al., "Intrabody Tissue-Specific Delivery of Antisense Conjugates in Animals: Ligand-Linker-Antisense Oligomer Conjugates," Methods in Enzymolology, 2000, vol. 313(17), pp. 297-321, 25 pages.
Fisicaro et al., "Antiviral Intrahepatic T-Cell Responses Can Be Restored by Blocking Programmed Death-1 Pathway in Chronic Hepatitis B," Gastroenterology, 2010, 138, pp. 682-693, 16 pages.
Fluiter, K et al., "Filling the gap in LNA antisense oligo gapmers: the effects of unlocked nucleic acid (UNA) and 4'C-hydroxymethyl-DNA modifications on RNase H recruitment and efficacy of an LNA gapmer," Molecular Biosystems, 2009, vol. 5, pp. 838-843, 6 pages.
Freier, SM et al., "The ups and downs of nucleic acid duplex stability: structure-stability studies on chemically-modified DNA:RNA duplexes," Nucleic Acids Research, 1997, vol. 25(22), pp. 4429-4443, 16 pages.
Geng, Ca et al., "Small-molecule inhibitors for the treatment of hepatitis B virus documented in patents," Mini Reviews in Medicinal Chemistry, Bentham Science Publ, NL, vol. 13, No. 5, 2013, pp. 749-776, 28 pages.
Hadziyannis, S.J., "Natural history of chronic hepatitis B in Euro-Mediterranean and African Countries," Journal of Hepatology, 2011, vol. 55, 183-191, 1 page.
Hansen, LD et al., "Entropy Titration. A calorimetric method for the determination of $\Delta G°$ (K), $\Delta H°$ and $\Delta S°$ 1," Chemical Communications, 1965, No. 3, pp. 36-38, 3 pages.
Hantz, O et al., "Persistence of the hepatitis B virus covalently closed circular DNA in HepaRG human hepatocyte-like cells," Journal of General Virology, 2009, vol. 90, Part 1, pp. 127-135, 9 pages.
Heidenreich, M et al., "Applications of CRISPR-Cas systems in neuroscience", Nat Rev Neurosci, 2016, vol. 17(1) pp. 36-44, 23 pages.
Hirao, I et al., "Natural versus Artificial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.
Holdgate, GA et al., "Measurements of binding thermodynamics in drug discovery," Drug Discovery Today, 2005, vol. 10, No. 22, pp. 1543-1550, 8 pages.
Ishida, Y et al., "Novel Robust in Vitro Hepatitis B Virus Infection Model Using Fresh Human Hepatocytes Isolated from Humanized Mice," American Journal of Pathology, 2015, vol. 185, No. 5, pp. 1275-1285, 11 pages.
Janssen et al., "Pegylated interferon alfa-2b alone or in combination with lamivudine for HBeAg-positive chronic hepatitis B: a randomised trial," Lancet, 2005, 365, pp. 123-129, 7 pages.
Khorev, O et al., "Trivalent, Gal/GalNAc-containing ligands designed for the asialoglycoprotein receptor," Bioorganic & Medicinal Chemistry, 2008, vol. 16(9), pp. 5216-5231, 16 pages.
Knowles, BB et al., "Human Hepatocellular Carcinoma Cell Lines Secrete the Major Plasma Proteins and Hepatitis B Surface Antigen," Science, 1980, vol. 209(4455), pp. 497-499, 3 pages.
Kondo et al., "Recovery of Functional Cytotoxic T LymphocytesDuring Lamivudine Therapy by AcquiringMulti-Specificity," Journal of Medical Virology, 2004, vol. 74, pp. 425-433, 9 pages.
Kondo et al., "Hepatitis B Surface Antigen Could Contribute to the Immunopathogenesis of Hepatitis B Virus Infection," ISRN Gasteroenterology, 2013, Article ID 935295, 9 pages.

Kumar et al., "Hepatitis B Virus Regulatory HBx Protein Binds to Adaptor Protein IPS-1 and Inhibits the Activation of Beta Interferon," J Virol, 2011, 85:2, pp. 987-995, 9 pages.
Lagos-Quintana, M et al. "New microRNAs from mouse and human," RNA, 2003, vol. 9, pp. 175-179, 5 pages.
Langer, R, "New Methods of Drug Delivery," Science, 1990, vol. 249, issue 4976, pp. 1527-1533, 7 pages.
Lewis BP et al., "Conserved Seed Pairing, Often Flanked by Adenosines, Indicates that Thousands of Human Genes are MicroRNA Targets," Cell, 2005, vol. 120, pp. 15-20, 6 pages.
Liaw et al., "Hepatitis B virus infection," Lancet, 2009, 373, pp. 582-592, 11 pages.
Liaw et al., "Hepatitis B e Antigen Seroconversion: A Critical Event in Chronic Hepatitis B Virus Infection," Dig. Dis. Sci., 2010, 55, pp. 2727-2734, 8 pages.
Licitra, EJ et al., "A three-hybrid system for detecting small ligand-protein receptor interactions", Proc Natl Academy of Science USA, 1996, vol. 93, pp. 12817-12821, 5 pages.
Wang, et al., "Identification of acetyltransferase genes (HAT1 and KAT8) regulating HBV replication by RNAi screening," Cell Biosci (2015), 5:66, 9 pages.
PCT International Search Report for PCT International Patent Application No. PCT/EP2017/064981, dated Oct. 2, 2017.
Schulze A. et al., Hepatitis B virus infection initiates with a large surface protein-dependent binding to heparan sulfate proteoglycans, Hepatology, 2007, vol. 46(6), pp. 1759-1768.
U.S. Centers for Disease Control and Prevention ("CDC"), "Hepatitis B FAQs for the Public", retrieved Jan. 28, 2020, 7 pages.
World Health Organization ("WHO"), "Hepatitis B Fact sheet No. 204", Jul. 2014, retrieved Jan. 28, 2020, 4 pages.
MiRTasBase accession No. MIRT026642 [miRNA, hsa-miR-192-5p : PAPD5, target gene], downloaded Jun. 28, 2019, 4 pages.
MiRTasBase accession No. MIRT026248 [miRNA, hsa-miR-192-5p : PAPD7, target gene], downloaded Jun. 28, 2019, 4 pages.
Examination Report issued in EP Application No. 17732082.7 dated Aug. 5, 2020, 5 pages.
Notice of Allowance dated May 6, 2020, in related U.S. Appl. No. 16/162,279, 10 pages.
Non-Final Office Action dated Jul. 1, 2020, in related U.S. Appl. No. 16/310,789, 20 pages.
Fakhr: Precise and efficient siRNA design: a key point in competent gene silencing, Cancer Gene Therapy 23, 73-82 (2016), 10 pgs.
Doudna: CRISPR-Cas: A Laboratory Manual, 2016 ISBN 978-1-621821-31-1, book details, 1 pg.
Gennaro: The Science and Practice of Pharmacy, Philadelphia: Lippincott, Williams & Wilkins, 2000, book details, 1 pg.
Rowe: Handbook of Pharmaceutical Excipients, Chicago, Pharmaceutical Press, 2005, book details, 1 pg.
Boele: PAPD5-mediated 3' adenylation and subsequent degradation of miR-21 is disrupted in proliferative disease, PNAS, vol. 111, No. 31, Aug. 5, 2014, 6 pgs.
Afang: The Current status and research progress of clinical treatment of hepatitis B drugs, Anti Infect Pharm, 2019, 6 pgs. Abstract only.
Burroughs: Genome Research, vol. 20, pp. 1398-1419, 14 pgs.
Chan: Antisense Oligonucleotides: from design to therapeutic application, Clinical and Experimental Pharmacology and Physiology, 2006, pp. 533-540, 8 pgs.
Friend: High-yield Preparation of Isolated Rat Liver Parenchymal Cells: A Biochemical and Fine Structrual Study, J. Cell Biol., 1969, 15 pgs.
Hagedorn: Managing the sequence-specificity of antisense oligonucleotides in drug discovery, Nucleic Acids Research, 2017, 21 pgs.
Inan: Hepartitis B Virus: Biology and Life Cycle, Viral Hepatitis Journal, 2015, vol. 1, pp. 1-7, 7 pgs.
Iobst: Selective Sugar Binding to the Carbohydrate Recognition Domains of the Rat Hepatic and Macrophage Asialoglycoprotein Recptors, 1996, 8 pgs.
Laishram: Poly(A) polymerase (PAP) diversity in gene expression—Star-PAP vs canonical PAP, FEBS Letters, 2014, vol. 588(14) pp. 2185-2197, 30 pgs.

(56) References Cited

OTHER PUBLICATIONS

Paterna: Antioxidant and Cytoprotective Properties of Tagatose in Cultured Murine Hepatocytes, 1998, Toxiol. Appl. Pharmacol., 1998, 9 pgs.
Russian Office Action issued in 2020115761/10(025899), 12 pgs.
Zenkova: Imperfectly matched nucleic acid complexes and their biochemical manifestation, Russian Chemical Reviews, 1993, pp. 414-435, 21 pgs.
International Search Report and Written Opinion issued in PCT/EP2017/064980 dated Sep. 15, 2017, 14 pgs.
International Preliminary Report on Patentability issued in PCT/EP2017/064980, dated Dec. 18, 2018, 9 pgs.
International Search Report and Written Opinion issued in PCT/EP2018/078136 dated Dec. 18, 2018, 13 pgs.
International Preliminary Report on Patentability issued in PCT/EP2018/078136 dated Apr. 21, 2020, 8 pgs.
Ansel's Pharmaceutical Dosage Forms and Drug Delivery Systems, Philadelphia: Lippincott, Williams & Wilkins, 2004, 4 pgs.
Centers for Disease Control and Prevention, Hepatitis B FAQs for the Public, http://www.cdc.gOv/hepatitis/b/bfaq.htm, 7 pgs.
Database EMBL, Aug. 18, 2010, (Aug. 18, 2010) Sequence 593709 from Patent EP2213738., XP002787331, Yetrieved from EBI accession No. EM PAT: HD716993 Database accession No. HD716993 sequence, 1 pg.
Liaw: Hepatitis B virus infection, The Lancet, vol. 373, 2009, 11 pgs.
Georges: Coordinated Regulation of Cell Cycle Transcripts by p53-InduciblemicroRNAs, miR-192 and miR-215, Cancer Research vol. 68(24) pp. 10105-10112, 9 pgs.
Hepatitis B Fact sheet N°204, http://www.who.int/medicalcentre/factsheets/fs204/en/, Jul. 2014, Retrieved Nov. 4, 2014, 4 pgs.
Notice of Refusal issued in JP 2018-565394, dated Jul. 30, 2021, 5 pgs.
Notice of Refusal issued in JP 2018-565300, dated May 26, 2021, 5 pgs.

* cited by examiner

A

B

SEQUENCE LISTING

```
<160> NUMBER OF SEQ ID NOS: 20

<210> SEQ ID NO 1
<211> LENGTH: 698
<212> TYPE: PRT
<213> ORGANISM: Homo sapiens

<400> SEQUENCE: 1

Met Arg Pro Arg Pro Arg Ser Ala Pro Gly Lys Pro Arg Arg Arg Ser
1               5                   10                  15

Arg Ala Arg Leu Arg Ser Ser Arg Thr Pro Ser Gly Gly Ala Ser Gly
            20                  25                  30

Gly Gly Gly Ser Ser Ser Ser Ser Thr Ala Thr Gly Gly Ser Gly
            35                  40                  45

Ser Ser Thr Gly Ser Pro Gly Gly Ala Ala Ser Ala Pro Ala Pro Ala
    50                  55                  60

Pro Ala Gly Met Tyr Arg Ser Gly Glu Arg Leu Leu Gly Ser His Ala
65                  70                  75                  80

Leu Pro Ala Glu Gln Arg Asp Phe Leu Pro Leu Glu Thr Thr Asn Asn
                85                  90                  95

Asn Asn Asn His His Gln Pro Gly Ala Trp Ala Arg Arg Ala Gly Ser
            100                 105                 110

Ser Ala Ser Ser Pro Pro Ser Ala Ser Ser Ser Pro His Pro Ser Ala
        115                 120                 125

Ala Val Pro Ala Ala Asp Pro Ala Asp Ser Ala Ser Gly Ser Ser Asn
    130                 135                 140

Lys Arg Lys Arg Asp Asn Lys Ala Ser Thr Tyr Gly Leu Asn Tyr Ser
145                 150                 155                 160

Leu Leu Gln Pro Ser Gly Gly Arg Ala Ala Gly Gly Gly Arg Ala Asp
                165                 170                 175

Gly Gly Gly Val Val Tyr Ser Gly Thr Pro Trp Lys Arg Arg Asn Tyr
            180                 185                 190

Asn Gln Gly Val Val Gly Leu His Glu Glu Ile Ser Asp Phe Tyr Glu
        195                 200                 205

Tyr Met Ser Pro Arg Pro Glu Glu Glu Lys Met Arg Met Glu Val Val
    210                 215                 220

Asn Arg Ile Glu Ser Val Ile Lys Glu Leu Trp Pro Ser Ala Asp Val
```

```
           225                 230                 235                 240
       Gln Ile Phe Gly Ser Phe Lys Thr Gly Leu Tyr Leu Pro Thr Ser Asp
                       245                 250                 255
       Ile Asp Leu Val Val Phe Gly Lys Trp Glu Asn Leu Pro Leu Trp Thr
                       260                 265                 270
       Leu Glu Glu Ala Leu Arg Lys His Lys Val Ala Asp Glu Asp Ser Val
                       275                 280                 285
       Lys Val Leu Asp Lys Ala Thr Val Pro Ile Ile Lys Leu Thr Asp Ser
       290                 295                 300
       Phe Thr Glu Val Lys Val Asp Ile Ser Phe Asn Val Gln Asn Gly Val
       305                 310                 315                 320
       Arg Ala Ala Asp Leu Ile Lys Asp Phe Thr Lys Lys Tyr Pro Val Leu
                       325                 330                 335
       Pro Tyr Leu Val Leu Val Leu Lys Gln Phe Leu Leu Gln Arg Asp Leu
                       340                 345                 350
       Asn Glu Val Phe Thr Gly Gly Ile Gly Ser Tyr Ser Leu Phe Leu Met
                       355                 360                 365
       Ala Val Ser Phe Leu Gln Leu His Pro Arg Glu Asp Ala Cys Ile Pro
       370                 375                 380
       Asn Thr Asn Tyr Gly Val Leu Ile Glu Phe Phe Glu Leu Tyr Gly
       385                 390                 395                 400
       Arg His Phe Asn Tyr Leu Lys Thr Gly Ile Arg Ile Lys Asp Gly Gly
                       405                 410                 415
       Ser Tyr Val Ala Lys Asp Glu Val Gln Lys Asn Met Leu Asp Gly Tyr
                       420                 425                 430
       Arg Pro Ser Met Leu Tyr Ile Glu Asp Pro Leu Gln Pro Gly Asn Asp
                       435                 440                 445
       Val Gly Arg Ser Ser Tyr Gly Ala Met Gln Val Lys Gln Ala Phe Asp
                       450                 455                 460
       Tyr Ala Tyr Val Val Leu Ser His Ala Val Ser Pro Ile Ala Lys Tyr
       465                 470                 475                 480
       Tyr Pro Asn Asn Glu Thr Glu Ser Ile Leu Gly Arg Ile Ile Arg Val
                       485                 490                 495
       Thr Asp Glu Val Ala Thr Tyr Arg Asp Trp Ile Ser Lys Gln Trp Gly
                       500                 505                 510
       Leu Lys Asn Arg Pro Glu Pro Ser Cys Asn Gly Asn Gly Val Thr Leu
                       515                 520                 525
       Ile Val Asp Thr Gln Gln Leu Asp Lys Cys Asn Asn Asn Leu Ser Glu
       530                 535                 540
       Glu Asn Glu Ala Leu Gly Lys Cys Arg Ser Lys Thr Ser Glu Ser Leu
       545                 550                 555                 560
       Ser Lys His Ser Ser Asn Ser Ser Ser Gly Pro Val Ser Ser Ser Ser
                       565                 570                 575
       Ala Thr Gln Ser Ser Ser Ser Asp Val Asp Ser Asp Ala Thr Pro Cys
                       580                 585                 590
       Lys Thr Pro Lys Gln Leu Leu Cys Arg Pro Ser Thr Gly Asn Arg Val
                       595                 600                 605
       Gly Ser Gln Asp Val Ser Leu Glu Ser Ser Gln Ala Val Gly Lys Met
                       610                 615                 620
       Gln Ser Thr Gln Thr Thr Asn Thr Ser Asn Ser Thr Asn Lys Ser Gln
       625                 630                 635                 640
       His Gly Ser Ala Arg Leu Phe Arg Ser Ser Ser Lys Gly Phe Gln Gly
                       645                 650                 655
```

-continued

```
Thr Thr Gln Thr Ser His Gly Ser Leu Met Thr Asn Lys Gln His Gln
            660                 665                 670

Gly Lys Ser Asn Asn Gln Tyr Tyr His Gly Lys Lys Arg Lys His Lys
            675                 680                 685

Arg Asp Ala Pro Leu Ser Asp Leu Cys Arg
    690                 695

<210> SEQ ID NO 2
<211> LENGTH: 698
<212> TYPE: PRT
<213> ORGANISM: Homo sapiens

<400> SEQUENCE: 2

Met Arg Pro Arg Pro Arg Ser Ala Pro Gly Lys Pro Arg Arg Arg Ser
1               5                   10                  15

Arg Ala Arg Leu Arg Ser Ser Arg Thr Pro Ser Gly Gly Ala Ser Gly
                20                  25                  30

Gly Gly Gly Ser Ser Ser Ser Ser Thr Ala Thr Gly Gly Ser Gly
            35                  40                  45

Ser Ser Thr Gly Ser Pro Gly Gly Ala Ala Ser Ala Pro Ala Pro Ala
    50                  55                  60

Pro Ala Gly Met Tyr Arg Ser Gly Glu Arg Leu Leu Gly Ser His Ala
65                  70                  75                  80

Leu Pro Ala Glu Gln Arg Asp Phe Leu Pro Leu Glu Thr Thr Asn Asn
                85                  90                  95

Asn Asn Asn His His Gln Pro Gly Ala Trp Ala Arg Arg Ala Gly Ser
            100                 105                 110

Ser Ala Ser Ser Pro Pro Ser Ala Ser Ser Pro His Pro Ser Ala
            115                 120                 125

Ala Val Pro Ala Ala Asp Pro Ala Asp Ser Ala Ser Gly Ser Ser Asn
    130                 135                 140

Lys Arg Lys Arg Asp Asn Lys Ala Ser Thr Tyr Gly Leu Asn Tyr Ser
145                 150                 155                 160

Leu Leu Gln Pro Ser Gly Gly Arg Ala Ala Gly Gly Gly Arg Ala Asp
                165                 170                 175

Gly Gly Gly Val Val Tyr Ser Gly Thr Pro Trp Lys Arg Arg Asn Tyr
            180                 185                 190

Asn Gln Gly Val Val Gly Leu His Glu Glu Ile Ser Asp Phe Tyr Glu
            195                 200                 205

Tyr Met Ser Pro Arg Pro Glu Glu Lys Met Arg Met Glu Val Val
    210                 215                 220

Asn Arg Ile Glu Ser Val Ile Lys Glu Leu Trp Pro Ser Ala Asp Val
225                 230                 235                 240

Gln Ile Phe Gly Ser Phe Lys Thr Gly Leu Tyr Leu Pro Thr Ser Asp
                245                 250                 255

Ile Asp Leu Val Val Phe Gly Lys Trp Glu Asn Leu Pro Leu Trp Thr
            260                 265                 270

Leu Glu Glu Ala Leu Arg Lys His Lys Val Ala Asp Glu Asp Ser Val
            275                 280                 285

Lys Val Leu Asp Lys Ala Thr Val Pro Ile Ile Lys Leu Thr Asp Ser
    290                 295                 300

Phe Thr Glu Val Lys Val Asp Ile Ser Phe Asn Val Gln Asn Gly Val
305                 310                 315                 320

Arg Ala Ala Asp Leu Ile Lys Asp Phe Thr Lys Lys Tyr Pro Val Leu
```

```
                    325                 330                 335
        Pro Tyr Leu Val Leu Val Leu Lys Gln Phe Leu Leu Gln Arg Asp Leu
                        340                 345                 350
        Asn Glu Val Phe Thr Gly Gly Ile Gly Ser Tyr Ser Leu Phe Leu Met
                        355                 360                 365
        Ala Val Ser Phe Leu Gln Leu His Pro Arg Glu Asp Ala Cys Ile Pro
                        370                 375                 380
        Asn Thr Asn Tyr Gly Val Leu Leu Ile Glu Phe Phe Glu Leu Tyr Gly
        385                 390                 395                 400
        Arg His Phe Asn Tyr Leu Lys Thr Gly Ile Arg Ile Lys Asp Gly Gly
                        405                 410                 415
        Ser Tyr Val Ala Lys Asp Glu Val Gln Lys Asn Met Leu Asp Gly Tyr
                        420                 425                 430
        Arg Pro Ser Met Leu Tyr Ile Glu Asp Pro Leu Gln Pro Gly Asn Asp
                        435                 440                 445
        Val Gly Arg Ser Ser Tyr Gly Ala Met Gln Val Lys Gln Ala Phe Asp
        450                 455                 460
        Tyr Ala Tyr Val Val Leu Ser His Ala Val Ser Pro Ile Ala Lys Tyr
        465                 470                 475                 480
        Tyr Pro Asn Asn Glu Thr Glu Ser Ile Leu Gly Arg Ile Ile Arg Val
                        485                 490                 495
        Thr Asp Glu Val Ala Thr Tyr Arg Asp Trp Ile Ser Lys Gln Trp Gly
                        500                 505                 510
        Leu Lys Asn Arg Pro Glu Pro Ser Cys Asn Gly Asn Gly Val Thr Leu
                        515                 520                 525
        Ile Val Asp Thr Gln Gln Leu Asp Lys Cys Asn Asn Asn Leu Ser Glu
        530                 535                 540
        Glu Asn Glu Ala Leu Gly Lys Cys Arg Ser Lys Thr Ser Glu Ser Leu
        545                 550                 555                 560
        Ser Lys His Ser Ser Asn Ser Ser Gly Pro Val Ser Ser Ser Ser Ser
                        565                 570                 575
        Ala Thr Gln Ser Ser Ser Ser Asp Val Asp Ser Asp Ala Thr Pro Cys
                        580                 585                 590
        Lys Thr Pro Lys Gln Leu Leu Cys Arg Pro Ser Thr Gly Asn Arg Val
                        595                 600                 605
        Gly Ser Gln Asp Val Ser Leu Glu Ser Ser Gln Ala Val Gly Lys Met
                        610                 615                 620
        Gln Ser Thr Gln Thr Thr Asn Thr Ser Asn Ser Thr Asn Lys Ser Gln
        625                 630                 635                 640
        His Gly Ser Ala Arg Leu Phe Arg Ser Ser Lys Gly Phe Gln Gly
                        645                 650                 655
        Thr Thr Gln Thr Ser His Gly Ser Leu Met Thr Asn Lys Gln His Gln
                        660                 665                 670
        Gly Lys Ser Asn Asn Gln Tyr Tyr His Gly Lys Lys Arg Lys His Lys
                        675                 680                 685
        Arg Asp Ala Pro Leu Ser Asp Leu Cys Arg
        690                 695

<210> SEQ ID NO 3
<211> LENGTH: 792
<212> TYPE: PRT
<213> ORGANISM: Homo sapiens

<400> SEQUENCE: 3
```

```
Met Asp Pro Arg Val Ala Trp Ile Gln Pro Glu Gln Lys Gly Pro Ala
1               5                   10                  15
Asn Ala Leu Trp Met Gln Ile Trp Glu Thr Ser Gln Gly Val Gly Arg
            20                  25                  30
Gly Gly Ser Gly Phe Ala Ser Tyr Phe Cys Leu Asn Ser Pro Ala Leu
        35                  40                  45
Asp Thr Ala Ala Ala Ala Gly Ala Ala Gly Arg Gly Ser Gly Gly Leu
    50                  55                  60
Gly Pro Ala Leu Pro Ala Ser Pro Pro Pro Gly Pro Thr Ala
65              70                  75                  80
Pro Ala Ala Leu Pro Ala Leu Leu Thr Ala Leu Gly Pro Ala Ala
                85                  90                  95
Glu Gly Ala Arg Arg Leu His Lys Ser Pro Ser Leu Ser Ser Ser Ser
            100                 105                 110
Ser Ser Ser Ser Ser Asn Ala Glu Ser Gly Thr Glu Ser Pro Gly Cys
        115                 120                 125
Ser Ser Ser Ser Ser Ser Ala Ser Leu Gly Arg Pro Gly Gly Gly
        130                 135                 140
Arg Gly Gly Ala Phe Phe Asn Phe Ala Asp Gly Ala Pro Ser Ala Pro
145             150                 155                 160
Gly Thr Ala Asn Gly His Pro Gly Pro Arg Gly Pro Ala Pro Ala Gly
                165                 170                 175
Ser Pro Ser Gln His Gln Phe His Pro Gly Arg Arg Lys Arg Glu Asn
            180                 185                 190
Lys Ala Ser Thr Tyr Gly Leu Asn Tyr Leu Ser Gly Ser Arg Ala
            195                 200                 205
Ala Ala Leu Ser Gly Gly Gly Pro Gly Ala Gln Ala Pro Arg Pro
    210                 215                 220
Gly Thr Pro Trp Lys Ser Arg Ala Tyr Ser Pro Gly Ile Gln Gly Leu
225                 230                 235                 240
His Glu Glu Ile Ile Asp Phe Tyr Asn Phe Met Ser Pro Cys Pro Glu
                245                 250                 255
Glu Ala Ala Met Arg Arg Glu Val Val Lys Arg Ile Glu Thr Val Val
                260                 265                 270
Lys Asp Leu Trp Pro Thr Ala Asp Val Gln Ile Phe Gly Ser Phe Ser
            275                 280                 285
Thr Gly Leu Tyr Leu Pro Thr Ser Asp Ile Asp Leu Val Val Phe Gly
        290                 295                 300
Lys Trp Glu Arg Pro Pro Leu Gln Leu Leu Glu Gln Ala Leu Arg Lys
305                 310                 315                 320
His Asn Val Ala Glu Pro Cys Ser Ile Lys Val Leu Asp Lys Ala Thr
                325                 330                 335
Val Pro Ile Ile Lys Leu Thr Asp Gln Glu Thr Glu Val Lys Val Asp
                340                 345                 350
Ile Ser Phe Asn Met Glu Thr Gly Val Arg Ala Ala Glu Phe Ile Lys
            355                 360                 365
Asn Tyr Met Lys Lys Tyr Ser Leu Leu Pro Tyr Leu Ile Leu Val Leu
    370                 375                 380
Lys Gln Phe Leu Leu Gln Arg Asp Leu Asn Glu Val Phe Thr Gly Gly
385                 390                 395                 400
Ile Ser Ser Tyr Ser Leu Ile Leu Met Ala Ile Ser Phe Leu Gln Leu
        405                 410                 415
His Pro Arg Ile Asp Ala Arg Arg Ala Asp Glu Asn Leu Gly Met Leu
```

```
                  420               425               430
Leu Val Glu Phe Phe Glu Leu Tyr Gly Arg Asn Phe Asn Tyr Leu Lys
            435                 440                 445
Thr Gly Ile Arg Ile Lys Glu Gly Ala Tyr Ile Ala Lys Glu Glu
        450                 455                 460
Ile Met Lys Ala Met Thr Ser Gly Tyr Arg Pro Ser Met Leu Cys Ile
465                 470                 475                 480
Glu Asp Pro Leu Leu Pro Gly Asn Asp Val Gly Arg Ser Ser Tyr Gly
                485                 490                 495
Ala Met Gln Val Lys Gln Val Phe Asp Tyr Ala Tyr Ile Val Leu Ser
            500                 505                 510
His Ala Val Ser Pro Leu Ala Arg Ser Tyr Pro Asn Arg Asp Ala Glu
        515                 520                 525
Ser Thr Leu Gly Arg Ile Ile Lys Val Thr Gln Glu Val Ile Asp Tyr
        530                 535                 540
Arg Arg Trp Ile Lys Glu Lys Trp Gly Ser Lys Ala His Pro Ser Pro
545                 550                 555                 560
Gly Met Asp Ser Arg Ile Lys Ile Lys Glu Arg Ile Ala Thr Cys Asn
                565                 570                 575
Gly Glu Gln Thr Gln Asn Arg Glu Pro Glu Ser Pro Tyr Gly Gln Arg
            580                 585                 590
Leu Thr Leu Ser Leu Ser Ser Pro Gln Leu Leu Ser Ser Gly Ser Ser
        595                 600                 605
Ala Ser Ser Val Ser Ser Leu Ser Gly Ser Asp Val Asp Ser Asp Thr
        610                 615                 620
Pro Pro Cys Thr Thr Pro Ser Val Tyr Gln Phe Ser Leu Gln Ala Pro
625                 630                 635                 640
Ala Pro Leu Met Ala Gly Leu Pro Thr Ala Leu Pro Met Pro Ser Gly
                645                 650                 655
Lys Pro Gln Pro Thr Thr Ser Arg Thr Leu Ile Met Thr Thr Asn Asn
            660                 665                 670
Gln Thr Arg Phe Thr Ile Pro Pro Pro Thr Leu Gly Val Ala Pro Val
        675                 680                 685
Pro Cys Arg Gln Ala Gly Val Glu Gly Thr Ala Ser Leu Lys Ala Val
        690                 695                 700
His His Met Ser Ser Pro Ala Ile Pro Ser Ala Ser Pro Asn Pro Leu
705                 710                 715                 720
Ser Ser Pro His Leu Tyr His Lys Gln His Asn Gly Met Lys Leu Ser
                725                 730                 735
Met Lys Gly Ser His Gly His Thr Gln Gly Gly Tyr Ser Ser Val
            740                 745                 750
Gly Ser Gly Gly Val Arg Pro Pro Val Gly Asn Arg Gly His His Gln
        755                 760                 765
Tyr Asn Arg Thr Gly Trp Arg Arg Lys His Thr His Thr Arg Asp
        770                 775                 780
Ser Leu Pro Val Ser Leu Ser Arg
785                 790

<210> SEQ ID NO 4
<211> LENGTH: 8114
<212> TYPE: DNA
<213> ORGANISM: Homo sapiens

<400> SEQUENCE: 4
```

```
acaacgcgct ccctgcgggg cgggcggcaa cctccatgcg gcctcgtcca cgctcagcac      60
cggggaagcc gaggcggaga agccgcgcgc gcctcagaag ctcccggacg cccagcggcg     120
gcgcgagcgg cggcggcggc agcagcagca gcagcagcac ggccaccggc gggagcggca     180
gcagcaccgg cagccccggc ggcgcggcct cggcccggc cccggccccg gccggcatgt      240
atcgctccgg ggagcgcctg ctgggcagcc acgcgctgcc cgcggagcag cgggacttcc     300
tgcccctaga cgaccaac aacaacaaca accaccacca gcccggggcc tgggcccgcc       360
gggcgggctc ctcggcgtcc tcgcctccct cggcgtcctc gtccccgcac ccttcggccg     420
ccgtccccgc cgccgatcca gccgattcgg cctcgggcag cagcaacaag aggaagcgcg     480
acaacaaggc cagcacgtat ggactcaact acagcctgct gcagcccagc ggagggcggg     540
ccgcgggggg cggccgagca gacggcggcg gggtcgtgta cagcgggacc ccgtggaaac     600
ggaggaacta caaccaggga gtcgtgggtc tgcatgaaga aatcagtgat ttttatgaat     660
acatgtctcc aagacctgag gaggagaaga tgcggatgga ggtggtgaac aggatcgaga     720
gtgtaattaa ggagctctgg cccagcgctg acgtccagat atttgaagt tttaaaactg      780 gactttattt acctactagt gacatcgacc tagtggtgtt tgggaagtgg gagaacctac     840
ccctctggac tctggaagaa gctcttcgga acacaaagt cgcagatgag gattcggtga      900 aagtttaga caaagcaact gtacctatta ttaaattaac agattctttt actgaagtga     960
aagttgatat cagctttaat gtacagaatg gcgtgagagc agctgacctc atcaaagatt   1020
ttaccaagaa atatcctgta ttgccatact ggttttagt attgaaacaa ttcctattgc    1080
agagggacct taatgaagta tttacaggtg gaattggttc ttatagtctc tttttaatgg    1140
cagtcagttt ccttcagtta catcccaggg aagatgcttg catccccaat acaaactatg   1200
gtgttctctt aatagaattt tttgaattat atggacgaca cttcaattat ttaaagactg   1260
gcatccggat aaaggatggt ggttcatatg tggccaaaga tgaagtacag aaaaatatgc   1320
tagatggcta caggccatca atgctttata tcgaagatcc tttacaacca ggtaacgatg   1380
ttggaaggag ttcatatggg gccatgcaag tgaagcaggc ctttgattat gcctacgttg   1440
ttttgagtca tgctgtatca ccaatagcaa agtactatcc caacaatgaa acagaaagca   1500
tactaggtag aataattaga gtaacagatg aagttgccac atatagagat tggatatcaa   1560
agcagtgggg cttgaagaat agacctgagc cttcatgcaa tggaaatggt gttaccttga   1620
tagtagatac tcagcagtta gataaatgta ataataatct atctgaagaa aatgaagccc   1680
ttggaaaatg tagaagtaaa acctcggaat ctcttagtaa acactcttca aactcttcat   1740
caggtccagt gtcgtcctct tctgccacac agtccagctc tagtgatgta gattccgatg   1800
caacaccatg caaacccccg aaacagctgc tttgccgtcc gtccactggg aaccgagtag   1860
ggtcgcaaga tgtatccttg gagtcctctc aggcagttgg gaaaatgcaa agcacccaaa   1920
ccactaacac atccaacagc accaacaaat ctcagcatgg atcagcaagg ctctttcgtt   1980
cttccagcaa aggcttccaa ggtacaactc aaacaagcca tggttccttg atgacaaaca   2040
aacaacatca aggcaaatcc aataatcagt attaccatgg caaaaagagg aaacacaaga   2100
gggacgcgcc cctctcagac ctctgtagat agtcagcgct gcgcggtgga ctgtcttctc   2160
tgtgcaatga tctcatgctc aggacagttg cgcagggact cctgggagat attcaggagc   2220
ctcacactgt tcagacgttg acttagcaac tgcgtttttt cccagctcgc cacagaatgg   2280
atcatgaaga ctgacaactg caaaaaaaac aaaacaaaac aaaaaaaaaa gcaagcaaaa   2340
aagagggaaa aaaaaggctg cttatttgat aagtcatatg ctacaacagg gtcattttaa   2400
```

```
gatttaaagc ttgaatgtaa aataaatata tttctcattg gctttatgca gagttatagg   2460
gaatagtatt cagtgttggt agggtgatag aaacaaaaaa cagtatcaga ggatgaggtg   2520
gggaaggaaa acaaaggtat ctgataggaa gtccagattc caaagggaa agtgatctgt    2580 gcatgttttt ttttttaaata ttttttgcata tatttaccat tttattgtgt gtatatatag 2640
aagaccatat aggagattga tatttgtaat agtggatttg ttaataatac ttttttacata 2700 acattactgt ttaaattgta aacagattt ttctcaggat tagtttgaaa aataatctaa   2760
attgtcatct taacatccat atataggaa gtgattagtt ctattactca atttgttttt  2820
ctcagcattg aaatgactta atagaaccct tgtgtcctgc tgcaaaaatt tttcctctct  2880
aaagaaaagg tttatggtgg caaatgatgt ttattttatt ttgtaaaaaa aaaaaaatgt  2940
actatgtact tttgtgtaaa cactgaaaaa tctctggtca tctccgagaa ttaacttgca  3000
actgttttct atagtgctgt cgtcttgggc aatgggcaat tacatgactt tgtgtttgct  3060
tcctttgcag tctttttttt ttccccccat ttcttcctaa taggaaaaaa aaaaaaaaaa  3120
aggtcaccca tgtctggtct cattcctgtt gcagtgaaac ttcgagttcc acagactttg  3180
catgctggct tctctaaccc tgtgtgctgc gtgtgcctgt ttctcatctc ttattctttt  3240
taaaattcat gcttaactac tgtgggagaa taactgtaaa cagctttaat taaatcatac  3300
ttataaaaaa ctattttctt atattccact ctatgctttt ggtattgttg atctttacaa  3360
attaaatggt ctttgataat ggatctattt tgtattgcct tattaagacc aaatacttct  3420
tgtcatccca ttctttatcc tcttctttca tggaattgtt atcgttaatt aaaacttttt  3480
taaacattgg cttgtttcaa tcatactgta aattttggtt gtagtcagct ttgagtgcaa  3540
tgagatgtat aattctgtta tcattacctg ttgagtttga aactcagttg ggaatattta  3600
atataataga atgtaagtga catttctgaa aatgcttttct ttcagggtga aagctcttat  3660
gtttagcatc aatgtgtatg gctctgttaa atgcagccat ttctgagacg agattctttt  3720
atatatatat acatataaag tactattggc ttttaggagt ttcttttata tacatttatg  3780
aaatactgaa gaccaatcag accattaatg gacacttagt gtaacttttt ataaagaaaa  3840
taatgctaaa gtaagaccaa aactgatgtc atcactgaaa ttaacaattt tcaatatgtt  3900 catatttttaa ttcacaatgg aaaaatgtgt tccaaaactg gaaactcata gtactcgtgt  3960
aaactgtgga agatttcaaa tgtgatgtta ttttgacaat gttttaaatt ttagagtcac  4020
attttattct gatcagaatt tttattgaga tgttgagctt ttgttttttga aactagtttg  4080 tcataacatt gtgcataatc acagtattta ttttctagga caattgtgaa tgtgtagact  4140
tatgtttact gctaagggaa caattattta taaaataata ttaaatccag tattagctgc  4200
ctatttcaga cacttaatac ttgcagagat ctatgttaca tttaccacac tgaagttttt  4260
tttgttgttt tttgtttgtt tttaaagaat caccctcatt gttgaaagta aatgtactct  4320
tagggtgcga atattagtgt tccaataagc atgtgattat attaaggtgg tggtagcggg  4380
aagataattc tgattccatt gggaatctta ggttttcgta aatttattgg gaaaatagtt  4440 ttcctgtac tgctgaagtt tctttttggt aaacagtatc tttctaaaag aaaaaagcat   4500
gaaggagaaa ttgaggtgtg tatacatttc ctcaaatgac cagcattgta ttcgtgaata  4560
ctgtgtatct tgcagtgaac agtgtggaag ctgttcattt ttcaatctga agtaaaatac  4620
tttcaagaac ttttagtttg cctgctcatt tgttttatac atttcatcta tttgactcct  4680
atcttatttc ttttttgagt tttaatactt cctatatttt gtgaatatat cagaaatgtg  4740
```

```
tcatttatat attagagtcc attcatatcc atgaatcata accttccttt gctaatactt    4800
gttgaatggg attttacaaa ttctccctca ctctggtgac atttctcagg cagtcatgta    4860
tgtgtacctg gccattagaa atattaatat ttaaagactg ttttttagag gagctgatgg    4920
gttggtgagg tgtcagcaca aaatcttact ggttatgttt tgatgataaa agtatatcca    4980
ttttttccct ccagctttaa ggtgactgtg aaggtgcctg gttttgaatg tctttgtttg    5040
gtttggagat gtcgcactca gttttcaaat ctagcttgga tctgtaggac ctatgttttt    5100
tacaagtaat tgccctccag tcttcaacag ttgattctgt tttatttta tcctgttttg    5160 agtgtacttt acctttactt gcattttgag cctcattaat atttaggtta tttgatttgg    5220
ctccagatat tcctagatct gcacagggca aaacatgggc tataggtgtga gcattttaa    5280 ttgtcttttt ctgctggaac cttatatctc tccatgtgtt ttctgctcct tccctccccc    5340
atgaaatggt aagtgtgact tgtgtttgcc tgaacctgtg gactagtgtt tgggggtttct   5400 ggaaacacta gagggtcaga aaagagtaat gaccaccgtg acgtgcagga ttctcttgct    5460
gtgacatgtt cattgcaaag ccctctccag tgactaggag gtgtagttat taaggttgat    5520
ctgttagaaa tcaccattat taggtattag tggtagatgt tgctgatact tttattggtc    5580
atgactacat ctcagtttta ctttaatatt gatctatagt ttgatcagtt ccttgaattc    5640
taatatgttg atttctcagt gtttctgtca ctaaccaaga atgtttctag gcagttggtt    5700
gcttcacagt caaaactaaa tggtaaacta tcaaaaatac attcccaatt ttgctgtgat    5760
aaatattgaa atgttaaaat taatgaacag aagaatttat tcttacccat ctattcttgt    5820
tctcctagtt cattaaactt tcagttattg gaaaggcaca ttctcaaagt attttatgag    5880
caaaatattc tataaatgcg tctaacaaac ctaattgaat ataaaagtta tatttagtag    5940
ttactgttga tagtaatttt catcagggtc atagttcatc tagtaaaata tttagagaat    6000
gatgttaaca ttccagcatt aaagtgggaa caaagattta tatgaaaat tccttaaaag    6060 agttcatctt gccttggttt ctgaccctca agactctagc tacctgccat cttgtcaaaa    6120
catttgtggg tagaataagt gttaaagatc aaatttaat atgcttctcg atatttaaca    6180
tagctaagaa gccagatttt actgtagaag ttatttacat gatttgaaaa cttgacctaa    6240
ctggaagcct tttctcagt catcttgttc taagccatct tgacttcaca cccttagcga    6300
cttttctttt ttttttggtc aaagataatg agctaaatat atatagacgt tgaatgttga    6360
caaaattatt aaccagaaaa attgcttata aaggctgctg atctatttga tacctagaat    6420
taaatatttg aggacagttt ttagttaata aactgctaat gttatttta ctgtctctca    6480 ggttttttggt ttttttaaaa aaaatgtgtt tggcctttac attttctact taagtgtgta    6540
ctttattgag tttaaccttg tctgtagcct agtagcctga aagaaaagga gacagaacca    6600
gagagatgga tgtagtgcat tccctttggt tattacacat ttgtggtagc tcctggattt    6660
actgagagat attttagcta tgtcaataag aacagctaat gatgtggaaa tcaggtgttc    6720
tcttgtgtat ttcagtgaac atttttatta gtagttgcat atcatctcta gttccacatt    6780
ttaacttaac gtctttgtgg cttcaccact gagctacctt tcactacacc agcttctgtg    6840
tggcctggta acatggaagg tctctcctaa ggacagtctg gacgtatttt ggggaatgt     6900 tatttatctt aaagatgcct agaaacaaaa cgcatatagt accagtgaga aactatgaag    6960
taaacaagtt gctcaggccg ggcatggtgg ctcacgcctg taatcccagc actttgggag    7020
gccgaagcgg gaggatggct tgaggctggg agtttgagac cttcatctct aaaaaaaaca    7080
aacaaaaacc tgaatggtga ggtgtggtgg aattgggtag gggagggaaa ggaggacttg    7140
```

```
gaaaagcatt ctccaaagcc agcaacttgg tgaagttcag tacttgcctc ttagaggtta      7200
ggccatgcct ttcaaagaga gtgaaatgat gggttatcag ccacattctt ggagttaata      7260
tttttcttca tctttcagtt tgggttctgt gctattcata gttcttccct aagaccattt      7320
cattattacc ttttatattt agttgcaatt tattataata tgttgttttg tccctgaact      7380
taatctccta attttaagat cctctctgat ttttgcatat tgaaacttac agaagtcact      7440
ttaaaaaagt cttttgaaag tcctacaatc ctaaaataaa tcacaagctt gtttgttaga      7500
cgtgtcaaga gtctccagtc tttactacta aaaagcagca ctgccttaac acacattgtt      7560
atgggtgaaa agtgagggac gaccagtgta gtttctggat ataaagtgtg aaggactgtt      7620
gagttaaaca tttttagtgg aatatacata gataacgtgt atttagaaac tttggtgaag      7680
ccagtatttg ttttttagtaa cctttttatg tatttccttc tttgattagc attgtcttca      7740
gtgttaagaa atgtggactc ctgtgaggtg ctggaggttt gaatcatctt gaaaactttc      7800
caatcttgtc tagttaccac tgcagagaca ctaaggaatt taccagaaaa agatatttga      7860
tacaagtgat ttaagaaatc tcaacatttc ctgaggccgt atcactgggc aaccagtgat      7920
gaaaactatg aatgaattgc acacctggaa gattttttaa gctaatgaca gtttcttcaa      7980
agatgtcaat tatttgcctt ggaaatttta taaattgcat ttctatgcac atcggcctct      8040
agtgcttacc actcggttta ttattcataa tctgcaattc aataaaggct ttgtgttttc      8100
atttatcttc aaaa                                                       8114

<210> SEQ ID NO 5
<211> LENGTH: 7973
<212> TYPE: DNA
<213> ORGANISM: Homo sapiens

<400> SEQUENCE: 5
acaacgcgct ccctgcgggg cgggcggcaa cctccatgcg gcctcgtcca cgctcagcac        60
cggggaagcc gaggcggaga agccgcgcgc gcctcagaag ctcccggacg cccagcggcg       120
gcgcgagcgg cggcggcggc agcagcagca gcagcagcac ggccaccggc gggagcggca       180
gcagcaccgg cagccccggc ggcgcggcct cggcccggc cccggccccg gccggcatgt       240
atcgctccgg ggagcgcctg ctgggcagcc acgcgctgcc cgcggagcag cgggacttcc       300
tgcccctaga gacgaccaac aacaacaaca accaccacca gcccggggcc tgggcccgcc       360
gggcgggctc ctcggcgtcc tcgcctcct cggcgtcctc gtccccgcac ccttcggccg       420
ccgtccccgc cgccgatcca gccgattcgg cctcgggcag cagcaacaag aggaagcgcg       480
acaacaaggc cagcacgtat ggactcaact acagcctgct gcagcccagc ggagggcggg       540 ccgcggggg cggccgagca gacggcggcg gggtcgtgta cagcgggacc ccgtggaaac       600
ggaggaacta caaccaggga gtcgtgggtc tgcatgaaga aatcagtgat tttatgaat        660 acatgtctcc aagacctgag gaggagaaga tgccggatgg ggtggtgaac aggatcgaga       720
gtgtaattaa ggagctctgg cccagcgctg acgtccagat atttggaagt tttaaaactg       780
gactttattt acctactagt gacatcgacc tagtggtgtt tgggaagtgg gagaacctac       840
ccctctggac tctggaagaa gctcttcgga acacaaagt cgcagatgag gattcggtga       900 aagtttaga caaagcaact gtacctatta ttaaattaac agattctttt actgaagtga       960
aagttgatat cagctttaat gtacagaatg gcgtgagagc agctgacctc atcaaagatt      1020
ttaccaagaa atatcctgta ttgccatact tggtttagt attgaaacaa ttcctattgc      1080
```

```
agagggacct taatgaagta tttacaggtg gaattggttc ttatagtctc tttttaatgg    1140
cagtcagttt ccttcagtta catcccaggg aagatgcttg catccccaat acaaactatg    1200
gtgttctctt aatagaattt tttgaattat atggacgaca cttcaattat ttaaagactg    1260
gcatccggat aaaggatggt ggttcatatg tggccaaaga tgaagtacag aaaaatatgc    1320
tagatggcta caggccatca atgctttata tcgaagatcc tttacaacca ggtaacgatg    1380
ttggaaggag ttcatatggg gccatgcaag tgaagcaggc ctttgattat gcctacgttg    1440
ttttgagtca tgctgtatca ccaatagcaa agtactatcc caacaatgaa acagaaagca    1500
tactaggtag aataattaga gtaacagatg aagttgccac atatagagat tggatatcaa    1560
agcagtgggg cttgaagaat agacctgagc cttcatgcaa tggtccagtg tcgtcctctt    1620
ctgccacaca gtccagctct agtgatgtag attccgatgc aacaccatgc aaaaccccga    1680
aacagctgct ttgccgtccg tccactggga accgagtagg gtcgcaagat gtatccttgg    1740
agtcctctca ggcagttggg aaaatgcaaa gcacccaaac cactaacaca tccaacagca    1800
ccaacaaatc tcagcatgga tcagcaaggc tctttcgttc ttccagcaaa ggcttccaag    1860
gtacaactca aacaagccat ggttccttga tgacaaacaa acaacatcaa ggcaaatcca    1920
ataatcagta ttaccatggc aaaaagagga acacaagag ggacgcgccc ctctcagacc    1980
tctgtagata gtcagcgctg cgcggtggac tgtcttctct gtgcaatgat ctcatgctca    2040
ggacagttgc gcagggactc ctgggagata ttcaggagcc tcacactgtt cagacgttga    2100
cttagcaact gcgttttttc ccagctcgcc acagaatgga tcatgaagac tgacaactgc    2160
aaaaaaaaca aaacaaaaca aaaaaaaaag caagcaaaaa agagggaaaa aaaaggctgc    2220
ttatttgata agtcatatgc tacaacaggg tcattttaag atttaaagct tgaatgtaaa    2280
ataaatatat ttctcattgg ctttatgcag agttataggg aatagtattc agtgttggta    2340
gggtgataga aacaaaaaac agtatcagag gatgaggtgg ggaaggaaaa caaaggtatc    2400
tgataggaag tccagattcc aaaggggaaa gtgatctgtg catgtttttt ttttaaatat    2460
ttttgcatat atttaccatt ttattgtgtg tatatataga agaccatata ggagattgat    2520
atttgtaata gtggatttgt taataatact ttttacataa cattactgtt taaattgtaa    2580
acagattttt tctcaggatt agtttgaaaa ataatctaaa ttgtcatctt aacatccata    2640
tatagggaag tgattagttc tattactcaa tttgttttc tcagcattga aatgacttaa    2700
tagaacccct gtgtcctgct gcaaaaattt ttcctctcta aagaaaaggt ttatggtggc    2760
aaatgatgtt tatttatttt tgtaaaaaaa aaaaatgta ctatgtactt ttgtgtaaac    2820
actgaaaaat ctctggtcat ctccgagaat taacttgcaa ctgtttctta tagtgctgtc    2880
gtcttgggca atgggcaatt acatgacttt gtgtttgctt cctttgcagt ctttttttt    2940 tccccccatt tcttcctaat aggaaaaaaa aaaaaaaaaa ggtcacccat gtctggtctc    3000
attcctgttg cagtgaaact tcgagttcca cagactttgc atgctggctt ctctaaccct    3060
gtgtgctgcg tgtgcctgtt tctcatctct tattcttttt aaaattcatg cttaactact    3120
gtgggagaat aactgtaaac agctttaatt aaatcatact tataaaaaac tattttctta    3180
tattccactc tatgcttttg gtattgttga tcttacaaa ttaaatggtc tttgataatg    3240
gatctatttt gtattgcctt attaagacca aatacttctt gtcatcccat tctttatcct    3300
cttctttcat ggaattgtta tcgttaatta aaacttttt aaacattggc ttgtttcaat    3360
catactgtaa attttggttg tagtcagctt tgagtgcaat gagatgtata attctgttat    3420
cattacctgt tgagtttgaa actcagttgg gaatatttaa tataatagaa tgtaagtgac    3480
```

```
atttctgaaa atgctttctt tcagggtgaa agctcttatg tttagcatca atgtgtatgg   3540
ctctgttaaa tgcagccatt tctgagacga gattctttta tatatatata catataaagt   3600
actattggct tttaggagtt tcttttatat acatttatga aatactgaag accaatcaga   3660
ccattaatgg acactagtg taactttta taaagaaaat aatgctaaag taagaccaaa     3720
actgatgtca tcactgaaat taacaatttt caatatgttc atattttaat tcacaatgga   3780
aaaatgtgtt ccaaaactgg aaactcatag tactcgtgta aactgtggaa gatttcaaat   3840
gtgatgttat tttgacaatg ttttaaattt tagagtcaca ttttattctg atcagaattt   3900
ttattgagat gttgagcttt tgtttttgaa actagtttgt cataacattg tgcataatca   3960
cagtatttat tttctaggac aattgtgaat gtgtagactt atgttactg ctaagggaac    4020 aattatttat aaaataatat taaatccagt attagctgcc tatttcagac acttaatact   4080
tgcagagatc tatgttacat ttaccacact gaagtttttt ttgttgtttt ttgtttgttt   4140
ttaaagaatc accctcattg ttgaaagtaa atgtactctt agggtgcgaa tattagtgtt   4200
ccaataagca tgtgattata ttaaggtggt ggtagcggga agataattct gattccattg   4260
ggaatcttag gttttcgtaa atttattggg aaaatagttt ttcctgtact gctgaagttt   4320 cttttttggta aacagtatct ttctaaaaga aaaagcatg aaggagaaat tgaggtgtgt    4380
atacatttcc tcaaatgacc agcattgtat tcgtgaatac tgtgtatctt gcagtgaaca   4440
gtgtggaagc tgttcatttt tcaatctgaa gtaaaatact ttcaagaact tttagtttgc   4500
ctgctcattt gttttataca tttcatctat ttgactccta tcttatttct tttttgagtt   4560
ttaatacttc ctatattttg tgaatatatc agaaatgtgt catttatata ttagagtcca   4620
ttcatatcca tgaatcataa ccttcctttg ctaatacttg ttgaatggga ttttacaaat   4680
tctccctcac tctggtgaca tttctcaggc agtcatgtat gtgtacctgg ccattagaaa   4740
tattaatatt taaagactgt ttttagagg agctgatggg ttggtgaggt gtcagcacaa    4800
aatcttactg gttatgtttt gatgataaaa gtatatccat tttttccctc cagctttaag   4860
gtgactgtga aggtgcctgg ttttgaatgt ctttgtttgg tttggagatg tcgcactcag   4920
ttttcaaatc tagcttggat ctgtaggacc tatgttttt acaagtaatt gccctccagt     4980
cttcaacagt tgattctgtt ttatttttat cctgttttga gtgtacttta cctttacttg   5040
cattttgagc ctcattaata tttaggttat ttgatttggc tccagatatt cctagatctg   5100
cacagggcaa acatgggct atagggtgag catttttaat tgtcttttc tgctggaacc      5160 ttatatctct ccatgtgttt tctgctcctt ccctccccca tgaaatggta agtgtgactt   5220
gtgtttgcct gaacctgtgg actagtgttt ggggtttctg gaaacactag agggtcagaa   5280
aagagtaatg accaccgtga cgtgcaggat tctcttgctg tgcatgttc attgcaaagc    5340 cctctccagt gactaggagg tgtagttatt aaggttgatc tgttagaaat caccattatt   5400
aggtattagt ggtagatgtt gctgatactt ttattggtca tgactacatc tcagttttac   5460
tttaatattg atctatagtt tgatcagttc cttgaattct aatatgttga tttctcagtg   5520
tttctgtcac taaccaagaa tgtttctagg cagttggttg cttcacagtc aaaactaaat   5580
ggtaaactat caaaaataca ttcccaattt tgctgtgata aatattgaaa tgttaaaatt   5640
aatgaacaga agaatttatt cttacccatc tattcttgtt ctcctagttc attaaacttt   5700
cagttattgg aaaggcacat tctcaaagta ttttatgagc aaaatattct ataaatgcgt   5760
ctaacaaacc taattgaata taaaagttat atttagtagt tactgttgat agtaattttc   5820
```

| | | | | | |
|---|---|---|---|---|---|
| atcagggtca | tagttcatct | agtaaaatat | ttagagaatg | atgttaacat | tccagcatta | 5880 |
| aagtgggaac | aaagatttat | atatgaaatt | ccttaaaaga | gttcatcttg | ccttggtttc | 5940 |
| tgaccctcaa | gactctagct | acctgccatc | ttgtcaaaac | atttgtgggt | agaataagtg | 6000 |
| ttaaagatca | aattttaata | tgcttctcga | tatttaacat | agctaagaag | ccagatttta | 6060 |
| ctgtagaagt | tatttacatg | atttgaaaac | ttgacctaac | tggaagcctt | tttctcagtc | 6120 |
| atcttgttct | aagccatctt | gacttcacac | ccttagcgac | ttttcttttt | ttttggtca | 6180 |
| aagataatga | gctaaatata | tatagacgtt | gaatgttgac | aaaattatta | accagaaaaa | 6240 |
| ttgcttataa | aggctgctga | tctatttgat | acctagaatt | aaatatttga | ggacagtttt | 6300 |
| tagttaataa | actgctaatg | tttatttttac | tgtctctcag | gttttggtt | tttttaaaaa | 6360 |
| aaatgtgttt | ggcctttaca | ttttctactt | aagtgtgtac | tttattgagt | ttaaccttgt | 6420 |
| ctgtagccta | gtagcctgaa | agaaaaggag | acagaaccag | agagatggat | gtagtgcatt | 6480 |
| ccctttggtt | attacacatt | tgtggtagct | cctggattta | ctgagagata | ttttagctat | 6540 |
| gtcaataaga | acagctaatg | atgtggaaat | caggtgttct | cttgtgtatt | tcagtgaaca | 6600 |
| ttttttattag | tagttgcata | tcatctctag | ttccacattt | taacttaacg | tctttgtggc | 6660 |
| ttcaccactg | agctaccttt | cactacacca | gcttctgtgt | ggcctggtaa | catggaaggt | 6720 |
| ctctcctaag | gacagtctgg | acgtatttg | ggggaatgtt | atttatctta | aagatgccta | 6780 |
| gaaacaaaac | gcatatagta | ccagtgagaa | actatgaagt | aaacaagttg | ctcaggccgg | 6840 |
| gcatggtggc | tcacgcctgt | aatcccagca | ctttgggagg | ccgaagcggg | aggatggctt | 6900 |
| gaggctggga | gtttgagacc | ttcatctctt | aaaaaaacaa | acaaaaacct | gaatggtgag | 6960 |
| gtgtggtgga | attgggtagg | ggagggaaag | gaggacttgg | aaaagcattc | tccaaagcca | 7020 |
| gcaacttggt | gaagttcagt | acttgcctct | tagaggttag | gccatgcctt | tcaaagagag | 7080 |
| tgaaatgatg | ggttatcagc | cacattcttg | gagttaatat | ttttcttcat | ctttcagttt | 7140 |
| gggttctgtg | ctattcatag | ttcttcccta | agaccatttc | attattacct | tttatattta | 7200 |
| gttgcaattt | attataatat | gttgttttgt | ccctgaactt | aatctcctaa | ttttaagatc | 7260 |
| ctctctgatt | tttgcatatt | gaaacttaca | gaagtcactt | taaaaaagtc | ttttgaaagt | 7320 |
| cctacaatcc | taaaataaat | cacaagcttg | tttgttagac | gtgtcaagag | tctccagtct | 7380 |
| ttactactaa | aaagcagcac | tgccttaaca | cacattgtta | tgggtgaaaa | gtgagggacg | 7440 |
| accagtgtag | tttctggata | taaagtgtga | aggactgttg | agttaaacat | ttttagtgga | 7500 |
| atatacatag | ataacgtgta | tttagaaact | ttggtgaagc | cagtatttgt | ttttagtaac | 7560 |
| cttttatgt | atttccttct | ttgattagca | ttgtcttcag | tgttaagaaa | tgtggactcc | 7620 |
| tgtgaggtgc | tggaggtttg | aatcatcttg | aaaactttcc | aatcttgtct | agttaccact | 7680 |
| gcagagacac | taaggaattt | accagaaaaa | gatatttgat | acaagtgatt | taagaaatct | 7740 |
| caacatttcc | tgaggccgta | tcactgggca | accagtgatg | aaaactatga | atgaattgca | 7800 |
| cacctggaag | atttttaag | ctaatgacag | tttcttcaaa | gatgtcaatt | atttgccttg | 7860 |
| gaaattttat | aaattgcatt | tctatgcaca | tcggcctcta | gtgcttacca | ctcggtttat | 7920 |
| tattcataat | ctgcaattca | ataaaggctt | tgtgttttca | tttatcttca | aaa | 7973 |

<210> SEQ ID NO 6
<211> LENGTH: 4511
<212> TYPE: DNA
<213> ORGANISM: Homo sapiens

<400> SEQUENCE: 6

-continued

```
gggcgcgcgg gccccgcggg ggcggcgcgt ggatggatcc gcgcgtggcc tggatccagc    60
ccgagcagaa ggggccggcc aatgccctgt ggatgcagat ctgggagacc tcgcagggcg   120
tgggccgcgg cggctcgggc ttcgcgtcct atttctgcct caactcgccg gcgctggaca   180
cggcggccgc ggcgggggcg gccgggcggg gcagtggcgg cctgggcccc cgcgctgcccg   240 ccgcgtcgcc cccgccgccc ggccccaccg cgcccgccgc gctgcccccc gcgctgctga   300
cggcgctggg gcccgcggcc gagggcgcgc ggcgcttgca caagtcgccg tcgctgtcgt   360
cctcgtcgtc gtcctcctcg tccaacgcgg agtcgggcac cgagagcccc ggctgctcgt   420
cgtcgtcctc cagcagcgcc tcgctgggcc ggccgggcgg cggccgcggc ggcgccttct   480
tcaacttcgc cgacggcgcg cccagcgccc ctggcacagc caacgggcac cccgggccgc   540
gcggccccgc gcccgccggc tccccgtcgc agcaccagtt ccacccgggt cgccggaaac   600
gcgagaacaa ggccagcacc tacggcctca actacctgct gtccggcagc cgcgcggccg   660
ctctcagcgg aggggcggc cccggggccc aggcgccgcg gcccgcaccc cgtggaaga    720 gccgcgcgta cagcccgggc atccagggac tacatgagga aataattgac ttttataact   780
tcatgtcccc ttgtcctgaa gaagcagcta tgagaagaga ggtggtgaaa cggatcgaaa   840
ctgtggtgaa agacctttgg ccgacggctg atgtacagat atttggcagc tttagtacag   900
gtctttatct tccaactagc gacatagacc tggtggtctt cgggaaatgg gagcgtcctc   960
ctttacagct gctggagcaa gccctgcgga agcacaacgt ggctgagccg tgttccatca  1020
aagtccttga caaggctacg gtaccaataa taaagctcac agatcaggag actgaagtga  1080
aagttgacat cagctttaac atggagacgg gcgtccgggc agcggagttc atcaagaatt  1140
acatgaagaa atattcattg ctgccttact tgattttagt attgaaacag ttccttctgc  1200
agagggacct gaatgaagtt tttacaggtg gaattagctc atacagccta attttaatgg  1260
ccattagctt tctacagttg catccaagaa ttgatgcccg gagagctgat gaaaaccttg  1320
gaatgcttct tgtagaattt tttgaactct atgggagaaa ttttaattac ttgaaaaccg  1380
gtattagaat caaagaagga ggtgcctata tcgccaaaga ggagatcatg aaagccatga  1440
ccagcgggta cagaccgtcg atgctgtgca ttgaggaccc cctgctgcca gggaatgacg  1500
ttggccggag ctcctatggc gccatgcagg tgaagcaggt cttcgattat gcctacatag  1560
tgctcagcca tgctgtgtca ccgctggcca ggtcctatcc aaacagagac gccgaaagta  1620
ctttaggaag aatcatcaaa gtaactcagg aggtgattga ctaccggagg tggatcaaag  1680
agaagtgggg cagcaaagcc cacccgtcgc aggcatggac agcaggatc aagatcaaag  1740 agcgaatagc cacatgcaat ggggagcaga cgcagaaccg agagcccgag tctccctatg  1800
gccagcgctt gactttgtcg ctgtccagcc cccagctcct gtcttcaggc cctcggcct   1860 cttctgtgtc ttcactttct gggagtgacg ttgattcaga cacaccgccc tgcacaacgc  1920
ccagtgttta ccagttcagt ctgcaagcgc agctcctct catggccggc ttacccaccg   1980
ccttgccaat gcccagtggc aaacctcagc ccaccacttc cagaacactg atcatgacaa  2040
ccaacaatca gaccaggttt actatacctc caccgaccct aggggttgct cctgttcctt  2100
gcagacaagc tggtgtagaa ggaactgcgt cttttgaaagc cgtccaccac atgtcttccc  2160
cggccattcc ctcagcgtcc cccaacccgc tctcgagccc tcatctgtat cataagcagc  2220
acaacggcat gaaactgtcc atgaagggct ctcacgccca cacccaaggc ggcggctaca  2280
gctctgtggg tagcggaggt gtgcggcccc ctgtgggcaa caggggacac caccagtata  2340
```

-continued

| | |
|---|---|
| accgcaccgg ctggaggagg aaaaaacaca cacacacacg ggacagtctg cccgtgagcc | 2400 |
| tcagcagata atggctcctg gctgcgtcag cctcccccac ccctctgcag actgccccgc | 2460 |
| ggcctcggcc accggcaggg gaaccgagac cagcaccccg cacgtcagcc gggctcgcgg | 2520 |
| cacgcccgcc gctgatcact ctgcatgttt cttcgtgtgg tggtcgcgtc catcttcaag | 2580 |
| aacagctcgt tgtgctcatc tgtgaagcct tattaaacgt ggacgttgtt ttctgccttc | 2640 |
| ccaggattct tccttcagtg ctgaggcagg tcgggctcag gaactgcagg gacgtgaaca | 2700 |
| tgcgcttgcg gtttgaggta gccgtgtctg ttccttcgcg gtttgctatt ttcatttcct | 2760 |
| gttcgtcaaa gcagcagagg agatcaaacc ccgttcgtgt gtctttcctc cacggataag | 2820 |
| cttgggaggt cattgtttta ctgccctcac attttgtttg aaatttcaga actgttttttc | 2880 |
| tatgtaaata ttgaaaactt atgatttgtg caataactca gatattttttt atttaatttc | 2940 |
| ctattttcac ataagttata tttaagggag gagggaattt tttttaaaca agcttaggtc | 3000 |
| cttttcccgag ctgcattttc taagttgggt catcgtgtcg gctggttgtc tgacgagcat | 3060 |
| cgttacaaac accatgatga gggggtttggg gttttatttt gatgtctttt cttttggtcg | 3120 |
| gaagtgagtg aaggagccag gtcgccctga aggttttcca aagggcttgg ctccagagcc | 3180 |
| acctggcaga ctgcccgtgg ccctgctgtc gggcccccagg ccgttgtcct gctctgacca | 3240 |
| cagagtttta atgttttggt tttcacttct tttaaactgg acaacaaatc cagcatttca | 3300 |
| agtgccagaa gtataacttt ctaaggagag aagggttgtc acattataaa atctttagga | 3360 |
| aaatgtgaac tggaaaacgc ttcggtcagt tttagtgaca tagcctgtga tgatgggtct | 3420 |
| ggtgactatt attgcggacc gtggtaccca gttttaggaa tgtggagaaa ggaattctgt | 3480 |
| tgattccgtt gaggaatctg tagcgtatgc attcgttctg ttaagagcaa atctaggaga | 3540 |
| agtgcttcag ctgcccagtg cgccgtgggg agtgttttaa cggatcgtgt cgcaggagag | 3600 |
| cacagcccag cgttggggcc gggaccgctg gcgcccgacg tcggaagcat acaggtatac | 3660 |
| tatgcaagtg tattctgcca caacaaccac tgtctttgtt accttttttt gaacaagaat | 3720 |
| atatccatcc tgcctaaccc tgagtttttg gagcaccaca gttgtcctgg gagttggttg | 3780 |
| catcttgtag gccatctgac ttcctgtttt taaaacgggg gtctggtctt gctaaacact | 3840 |
| acaggtaggt tggtctttga agtccactag tggagaatgt caagacaaga tacttattac | 3900 |
| catgacatct gatgcatgtg cagcagtggg gagttctaga ttgatctctg aatgtgatcg | 3960 |
| acgcccagca aggacaagct ttaaaatgtc tgcggtctgc ccttttgaag caggactggc | 4020 |
| tcactctgtc attgggagct gtcagctgcg actgcaggtt ctctaggagg cattccagaa | 4080 |
| tagagtagca cactgtgtct gcagttctcg atgaccgaaa gttatcaaaa atatttaaaa | 4140 |
| tatttaaatt gtgaacctat tgataaagaa tattttataaa aactgatctg taggcctgta | 4200 |
| ctaatctcta cgcattagca atattgactg taaacccaca ttaaggaaac cactacgggt | 4260 |
| ctggcagtgc gtgtcccgtg gggtgtgcat tttaaaactc gattcataga cacaggtacc | 4320 |
| atgttccatt tccgtcatgg tgaagcaaat gaattggcct ggctaccact gtggtcgcgt | 4380 |
| gctacaggtt tgacaaaaag atatcatgtt tcgattttttt tgtgtgtgga caacaatatg | 4440 |
| gaagctaaaa ttgacatatt tttatgtaaa gttttctat tctttgattt ttaataaact | 4500 |
| ttggaaacca g | 4511 |

<210> SEQ ID NO 7
<211> LENGTH: 474
<212> TYPE: PRT
<213> ORGANISM: Homo sapiens

<400> SEQUENCE: 7

Thr Tyr Gly Leu Asn Tyr Ser Leu Leu Gln Pro Ser Gly Gly Arg Ala
1               5                   10                  15

Ala Gly Gly Arg Ala Asp Gly Gly Val Val Tyr Ser Gly Thr
            20                  25                  30

Pro Trp Lys Arg Arg Asn Tyr Asn Gln Gly Val Val Gly Leu His Glu
            35                  40                  45

Glu Ile Ser Asp Phe Tyr Glu Tyr Met Ser Pro Arg Pro Glu Glu Glu
        50                  55                  60

Lys Met Arg Met Glu Val Val Asn Arg Ile Glu Ser Val Ile Lys Glu
65                  70                  75                  80

Leu Trp Pro Ser Ala Asp Val Gln Ile Phe Gly Ser Phe Lys Thr Gly
                85                  90                  95

Leu Tyr Leu Pro Thr Ser Asp Ile Asp Leu Val Val Phe Gly Lys Trp
                100                 105                 110

Glu Asn Leu Pro Leu Trp Thr Leu Glu Glu Ala Leu Arg Lys His Lys
            115                 120                 125

Val Ala Asp Glu Asp Ser Val Lys Val Leu Asp Lys Ala Thr Val Pro
130                 135                 140

Ile Ile Lys Leu Thr Asp Ser Phe Thr Glu Val Lys Val Asp Ile Ser
145                 150                 155                 160

Phe Asn Val Gln Asn Gly Val Arg Ala Ala Asp Leu Ile Lys Asp Phe
                165                 170                 175

Thr Lys Lys Tyr Pro Val Leu Pro Tyr Leu Val Leu Val Leu Lys Gln
            180                 185                 190

Phe Leu Leu Gln Arg Asp Leu Asn Glu Val Phe Thr Gly Gly Ile Gly
            195                 200                 205

Ser Tyr Ser Leu Phe Leu Met Ala Val Ser Phe Leu Gln Leu His Pro
        210                 215                 220

Arg Glu Asp Ala Cys Ile Pro Asn Thr Asn Tyr Gly Val Leu Leu Ile
225                 230                 235                 240

Glu Phe Phe Glu Leu Tyr Gly Arg His Phe Asn Tyr Leu Lys Thr Gly
                245                 250                 255

Ile Arg Ile Lys Asp Gly Gly Ser Tyr Val Ala Lys Asp Glu Val Gln
            260                 265                 270

Lys Asn Met Leu Asp Gly Tyr Arg Pro Ser Met Leu Tyr Ile Glu Asp
            275                 280                 285

Pro Leu Gln Pro Gly Asn Asp Val Gly Arg Ser Ser Tyr Gly Ala Met
        290                 295                 300

Gln Val Lys Gln Ala Phe Asp Tyr Ala Tyr Val Val Leu Ser His Ala
305                 310                 315                 320

Val Ser Pro Ile Ala Lys Tyr Tyr Pro Asn Asn Glu Thr Glu Ser Ile
                325                 330                 335

Leu Gly Arg Ile Ile Arg Val Thr Asp Glu Val Ala Thr Tyr Arg Asp
            340                 345                 350

Trp Ile Ser Lys Gln Trp Gly Leu Lys Asn Arg Pro Glu Pro Ser Cys
            355                 360                 365

Asn Gly Asn Gly Val Thr Leu Ile Val Asp Thr Gln Gln Leu Asp Lys
        370                 375                 380

Cys Asn Asn Asn Leu Ser Glu Glu Asn Glu Ala Leu Gly Lys Cys Arg
385                 390                 395                 400

Ser Lys Thr Ser Glu Ser Leu Ser Lys His Ser Ser Asn Ser Ser Ser

```
                    405                 410                 415
Gly Pro Val Ser Ser Ser Ala Thr Gln Ser Ser Ser Asp Val
            420                 425                 430

Asp Ser Asp Ala Thr Pro Cys Lys Thr Pro Lys Gln Leu Leu Cys Arg
            435                 440                 445

Pro Ser Thr Gly Asn Arg Val Gly Ser Gln Asp Val Ser Leu Glu Ser
450                 455                 460

Ser Gln Ala Val Gly Lys Met Gln Ser Thr
465                 470

<210> SEQ ID NO 8
<211> LENGTH: 419
<212> TYPE: PRT
<213> ORGANISM: Homo sapiens

<400> SEQUENCE: 8

Leu Leu Gln Pro Ser Gly Gly Arg Ala Ala Gly Gly Arg Ala Asp
1               5                   10                  15

Gly Gly Gly Val Val Tyr Ser Gly Thr Pro Trp Lys Arg Arg Asn Tyr
            20                  25                  30

Asn Gln Gly Val Val Gly Leu His Glu Glu Ile Ser Asp Phe Tyr Glu
        35                  40                  45

Tyr Met Ser Pro Arg Pro Glu Glu Lys Met Arg Met Glu Val Val
50                  55                  60

Asn Arg Ile Glu Ser Val Ile Lys Glu Leu Trp Pro Ser Ala Asp Val
65                  70                  75                  80

Gln Ile Phe Gly Ser Phe Lys Thr Gly Leu Tyr Leu Pro Thr Ser Asp
                85                  90                  95

Ile Asp Leu Val Val Phe Gly Lys Trp Glu Asn Leu Pro Leu Trp Thr
                100                 105                 110

Leu Glu Glu Ala Leu Arg Lys His Lys Val Ala Asp Glu Asp Ser Val
            115                 120                 125

Lys Val Leu Asp Lys Ala Thr Val Pro Ile Ile Lys Leu Thr Asp Ser
130                 135                 140

Phe Thr Glu Val Lys Val Asp Ile Ser Phe Asn Val Gln Asn Gly Val
145                 150                 155                 160

Arg Ala Ala Asp Leu Ile Lys Asp Phe Thr Lys Lys Tyr Pro Val Leu
                165                 170                 175

Pro Tyr Leu Val Leu Val Leu Lys Gln Phe Leu Leu Gln Arg Asp Leu
                180                 185                 190

Asn Glu Val Phe Thr Gly Gly Ile Gly Ser Tyr Ser Leu Phe Leu Met
            195                 200                 205

Ala Val Ser Phe Leu Gln Leu His Pro Arg Glu Asp Ala Cys Ile Pro
210                 215                 220

Asn Thr Asn Tyr Gly Val Leu Leu Ile Glu Phe Phe Glu Leu Tyr Gly
225                 230                 235                 240

Arg His Phe Asn Tyr Leu Lys Thr Gly Ile Arg Ile Lys Asp Gly Gly
                245                 250                 255

Ser Tyr Val Ala Lys Asp Glu Val Gln Lys Asn Met Leu Asp Gly Tyr
            260                 265                 270

Arg Pro Ser Met Leu Tyr Ile Glu Asp Pro Leu Gln Pro Gly Asn Asp
        275                 280                 285

Val Gly Arg Ser Ser Tyr Gly Ala Met Gln Val Lys Gln Ala Phe Asp
290                 295                 300
```

```
Tyr Ala Tyr Val Val Leu Ser His Ala Val Ser Pro Ile Ala Lys Tyr
305                 310                 315                 320

Tyr Pro Asn Asn Glu Thr Glu Ser Ile Leu Gly Arg Ile Ile Arg Val
            325                 330                 335

Thr Asp Glu Val Ala Thr Tyr Arg Asp Trp Ile Ser Lys Gln Trp Gly
        340                 345                 350

Leu Lys Asn Arg Pro Glu Pro Ser Cys Asn Gly Pro Val Ser Ser Ser
    355                 360                 365

Ser Ala Thr Gln Ser Ser Ser Asp Val Asp Ser Asp Ala Thr Pro
370                 375                 380

Cys Lys Thr Pro Lys Gln Leu Leu Cys Arg Pro Ser Thr Gly Asn Arg
385                 390                 395                 400

Val Gly Ser Gln Asp Val Ser Leu Glu Ser Ser Gln Ala Val Gly Lys
                405                 410                 415

Met Gln Ser

<210> SEQ ID NO 9
<211> LENGTH: 320
<212> TYPE: PRT
<213> ORGANISM: Homo sapiens

<400> SEQUENCE: 9

Tyr Ser Pro Gly Ile Gln Gly Leu His Glu Ile Ile Asp Phe Tyr
1               5                   10                  15

Asn Phe Met Ser Pro Cys Pro Glu Glu Ala Met Arg Arg Glu Val
                20                  25                  30

Val Lys Arg Ile Glu Thr Val Val Lys Asp Leu Trp Pro Thr Ala Asp
            35                  40                  45

Val Gln Ile Phe Gly Ser Phe Ser Thr Gly Leu Tyr Leu Pro Thr Ser
        50                  55                  60

Asp Ile Asp Leu Val Val Phe Gly Lys Trp Glu Arg Pro Pro Leu Gln
65                  70                  75                  80

Leu Leu Glu Gln Ala Leu Arg Lys His Asn Val Ala Glu Pro Cys Ser
                85                  90                  95

Ile Lys Val Leu Asp Lys Ala Thr Val Pro Ile Ile Lys Leu Thr Asp
            100                 105                 110

Gln Glu Thr Glu Val Lys Val Asp Ile Ser Phe Asn Met Glu Thr Gly
        115                 120                 125

Val Arg Ala Ala Glu Phe Ile Lys Asn Tyr Met Lys Lys Tyr Ser Leu
130                 135                 140

Leu Pro Tyr Leu Ile Leu Val Leu Lys Gln Phe Leu Leu Gln Arg Asp
145                 150                 155                 160

Leu Asn Glu Val Phe Thr Gly Gly Ile Ser Ser Tyr Ser Leu Ile Leu
                165                 170                 175

Met Ala Ile Ser Phe Leu Gln Leu His Pro Arg Ile Asp Ala Arg Arg
            180                 185                 190

Ala Asp Glu Asn Leu Gly Met Leu Leu Val Glu Phe Phe Glu Leu Tyr
        195                 200                 205

Gly Arg Asn Phe Asn Tyr Leu Lys Thr Gly Ile Arg Ile Lys Glu Gly
210                 215                 220

Gly Ala Tyr Ile Ala Lys Glu Glu Ile Met Lys Ala Met Thr Ser Gly
225                 230                 235                 240

Tyr Arg Pro Ser Met Leu Cys Ile Glu Asp Pro Leu Leu Pro Gly Asn
                245                 250                 255
```

```
Asp Val Gly Arg Ser Ser Tyr Gly Ala Met Gln Val Lys Gln Val Phe
        260                 265                 270

Asp Tyr Ala Tyr Ile Val Leu Ser His Ala Val Ser Pro Leu Ala Arg
        275                 280                 285

Ser Tyr Pro Asn Arg Asp Ala Glu Ser Thr Leu Gly Arg Ile Ile Lys
        290                 295                 300

Val Thr Gln Glu Val Ile Asp Tyr Arg Arg Trp Ile Lys Glu Lys Trp
305                 310                 315                 320

<210> SEQ ID NO 10
<211> LENGTH: 19
<212> TYPE: RNA
<213> ORGANISM: artificial
<220> FEATURE:
<223> OTHER INFORMATION: Human PAPD5 target RNA

<400> SEQUENCE: 10
caucaaugcu uuauaucga                                                    19

<210> SEQ ID NO 11
<211> LENGTH: 19
<212> TYPE: RNA
<213> ORGANISM: artificial
<220> FEATURE:
<223> OTHER INFORMATION: Human PAPD5 target RNA

<400> SEQUENCE: 11
ggacgacacu ucaauuauu                                                    19

<210> SEQ ID NO 12
<211> LENGTH: 19
<212> TYPE: RNA
<213> ORGANISM: artificial
<220> FEATURE:
<223> OTHER INFORMATION: Human PAPD5 RNA target sequence

<400> SEQUENCE: 12
gauaaaggau ggugguuca                                                    19

<210> SEQ ID NO 13
<211> LENGTH: 19
<212> TYPE: RNA
<213> ORGANISM: artificial
<220> FEATURE:
<223> OTHER INFORMATION: human PAPD5 Target mRNA sequence

<400> SEQUENCE: 13
gaauagaccu gagccuuca                                                    19

<210> SEQ ID NO 14
<211> LENGTH: 19
<212> TYPE: RNA
<213> ORGANISM: artificial
<220> FEATURE:
<223> OTHER INFORMATION: human PAPD7 target mRNA sequence

<400> SEQUENCE: 14
ggagugacgu ugauucaga                                                    19

<210> SEQ ID NO 15
<211> LENGTH: 19
<212> TYPE: RNA
<213> ORGANISM: artificial
<220> FEATURE:
<223> OTHER INFORMATION: human PAPD7 target mRNA sequence
```

```
<400> SEQUENCE: 15
cggaguucau caagaauua                                                19

<210> SEQ ID NO 16
<211> LENGTH: 19
<212> TYPE: RNA
<213> ORGANISM: artificial
<220> FEATURE:
<223> OTHER INFORMATION: human PAPD7 target RNA sequence

<400> SEQUENCE: 16
cggaguucau caagaauua                                                19

<210> SEQ ID NO 17
<211> LENGTH: 19
<212> TYPE: RNA
<213> ORGANISM: artificial
<220> FEATURE:
<223> OTHER INFORMATION: human PAPD7 target mRNA sequence

<400> SEQUENCE: 17
gcgaauagcc acaugcaau                                                19

<210> SEQ ID NO 18
<211> LENGTH: 19
<212> TYPE: DNA
<213> ORGANISM: artificial
<220> FEATURE:
<223> OTHER INFORMATION: Primer

<400> SEQUENCE: 18
ctgtgccttg ggtggcttt                                                19

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
aaggaaagaa gtcagaaggc aaaa                                          24

<210> SEQ ID NO 20
<211> LENGTH: 25
<212> TYPE: DNA
<213> ORGANISM: artificial
<220> FEATURE:
<223> OTHER INFORMATION: probe

<400> SEQUENCE: 20
ttctttataa gggtcgatgt ccatg                                         25
```

PAPD5 AND PAPD7 INHIBITORS FOR TREATING A HEPATITIS B INFECTION

The present application claims the benefit of priority from PCT/EP2017/064981, filed 19 Jun. 2017, which in turn claims priority to EP 16175045.0, entitled "NUCLEIC ACID MOLECULE FOR REDUCTION OF PAPD5 AND PAPD7 mRNA FOR TREATING HEPATITIS B INFECTION," filed on 17 Jun. 2016, the contents of which are incorporated herein by reference.

FIELD OF THE INVENTION

The present invention relates to a method for identifying a compound that prevents, ameliorates and/or inhibits a hepatitis B virus (HBV) infection, wherein a compound that (i) reduces the expression and/or activity of PAP associated domain containing 5 (PAPD5) and/or PAP associated domain containing 7 (PAPD7); and/or (ii) binds to PAPD5 and/or PAPD7 and inhibits propagation of HBV; is identified as a compound that prevents, ameliorates and/or inhibits a HBV infection. The invention also provides for an inhibitor of PAPD5 and/or PAPD7 for use in treating and/or preventing a HBV infection; as well as a combined preparation comprising an inhibitor of PAPD5 and an inhibitor of PAPD7 for simultaneous or sequential use in the treatment or prevention of a HBV infection. Also comprised in the present invention is a pharmaceutical composition for use in the treatment and/or prevention of a HBV infection, and a method for monitoring the therapeutic success during the treatment of a HBV infection.

BACKGROUND

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, Hepatology, 46, (2007), 1759-68) and via the specific binding of HBV surface antigens (HBsAg) to the hepatocyte sodium-taurocholate cotransporting polypeptide (NTCP) receptor (Yan, J Virol, 87, (2013), 7977-91). The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the HBV infection remains a major health problem worldwide which concerns an estimated 350 million chronic carriers who have a higher risk of liver cirrhosis and hepatocellular carcinoma.

The secretion of antiviral cytokines in response to a HBV infection by the hepatocytes and/or the intra-hepatic immune cells plays a central role in the viral clearance of the infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) are thought to participate to the maintenance of the immunological tolerant state observed in chronically infected patients (CHB). The persistent exposure to HBsAg and other viral antigens can lead to HBV-specific T-cell deletion or to progressive functional impairment (Kondo, Journal of Immunology (1993), 150, 4659-4671; Kondo, Journal of Medical Virology (2004), 74, 425-433; Fisicaro, Gastroenterology, (2010), 138, 682-93;). Moreover HBsAg has been reported to suppress the function of immune cells such as monocytes, dendritic cells (DCs) and natural killer (NK) cells by direct interaction (Op den Brouw, Immunology, (2009b), 126, 280-9; Woltman, PLoS One, (2011), 6, e15324; Shi, J Viral Hepat. (2012), 19, e26-33; Kondo, ISRN Gasteroenterology, (2013), Article ID 935295).

HBsAg quantification is a significant biomarker for prognosis and treatment response in chronic hepatitis B. However the achievement of HBsAg loss and seroconversion is rarely observed in chronically infected patients but remains one of the ultimate goals of therapy. Current therapy such as Nucleos(t)ide analogues are molecules that inhibit HBV DNA synthesis but are not directed at reducing HBsAg level. Nucleos(t)ide analogs, even with prolonged therapy, only show weak HBsAg clearance comparable to those observed naturally (between −1%-2%) (Janssen, Lancet, (2005), 365, 123-9; Marcellin, N. Engl. J. Med., (2004), 351, 1206-17; Buster, Hepatology, (2007), 46, 388-94).

Hepatitis B e-antigen (also called HBV envelope antigen or HBeAg) is a viral protein that is secreted by hepatitis B infected cells. HBeAg is associated with chronic hepatitis B infections and is used as a marker of active viral disease and a patient's degree of infectiousness.

The function of the hepatitis B virus precore or HBeAg is not completely known. However HBeAg is well known to play a key role in viral persistence. HBeAg is thought to promote HBV chronicity by functioning as an immunoregulatory protein. In particular, the HBeAg is a secreted accessory protein, which appears to attenuate the host immune response to the intracellular nucleocapsid protein (Walsh, Virology, 2011, 411(1):132-141). The HBeAg acts as an immune tolerogen contributing to HBV persistence, and possibly functions in utero considering that soluble HBeAg traverses the placenta (Walsh, Virology, 2011, 411(1):132-141). Furthermore, HBeAg downregulates: i) cellular genes controlling intracellular signaling; and ii) the Toll-like receptor 2 (TLR-2) to dampen the innate immune response to viral infection (Walsh, Virology, 2011, 411(1):132-141). In the absence of HBeAg, HBV replication is associated with upregulation of the TLR2 pathway (Walsh, Virology, 2011, 411(1):132-141). Accordingly, HBeAg has a significant role in modulating virus/host interactions to influence the host immune response (Walsh, Virology, 2011, 411(1): 132-141). Thus, reducing HBeAg in HBeAg positive patient population may lead to reversal of HBV specific immune-dysfunction (Milich, 1997, J. Viral. Hep. 4: 48-59; Milich, 1998, J. Immunol. 160: 2013-2021). In addition, the secreted HBeAg is significantly more efficient than the intracellular hepatitis core antigen (HBcAg) at eliciting T-cell tolerance, and the split T-cell tolerance between the HBeAg and the HBcAg and the clonal heterogeneity of HBc/HBeAg-specific T-cell tolerance may have significant implications for natural HBV infection and especially for precore-negative chronic hepatitis (Chen, 2005, Journal of Virology, 79: 3016-3027).

Accordingly, reducing secretion of HBeAg in addition to secretion of HBsAg would lead to an improved inhibition of development of a chronic HBV infection as compared to the inhibition of secretion of HBsAg alone. In addition, the highest rates of transmission of an acute infection to chronic (>80%) have been reported in cases of materno-fetal and neonatal HBV transmission from HBeAg-positive mothers (Liaw, Lancet, 2009, 373: 582-592; Liaw, Dig. Dis. Sci., 2010, 55: 2727-2734; and Hadziyannis, 2011, Journal of hepatology, 55: 183-191). Therefore, reducing HBeAg in an expected mother may not only reduce the patient's degree of infectiousness, but may also inhibit the development of a chronic HBV infection of her child.

Therefore, in the therapy of HBV there is an unmet medical need to inhibit viral expression, particularly to inhibit secretion of HBsAg and HBeAg (Wieland, S. F. & F. V. Chisari. J Virol, (2005), 79, 9369-80; Kumar et al. J Virol, (2011), 85, 987-95; Woltman et al. PLoS One, (2011), 6, e15324; Op den Brouw et al. Immunology, (2009b), 126, 280-9).

WO 03/022987 discloses for example in Table 7A 1298 genes that are upregulated in hepatitis C-positive tissue. One of the mentioned genes is topoisomerase-related function protein 4 (TRF4, AF089897). AF089897 is also called TRF4-2, which is quite similar to position 880 to 2340 of SEQ ID NO: 4 herein. The observation that a fragment of PAPD5 is upregulated slightly in hepatitis C positive cells does not provide any indication that inhibiting PAPD5 represents an effective therapy. WO 03/022987A2 does not disclose any hint that fragments of PAPD5 plays any critical role during hepatitis C infection at all. In addition, HCV and HBV are two completely different viruses leading to two completely different diseases with different etiologies, different progression and different medication. This is in line with the observation of the present inventors that the PAPD5 and PAPD7 inhibitors DHQ and THP are inactive against hepatitis C virus (HCV) or other viruses beside HBV (data not shown).

In WO 2010/040571 PAPD5 has been suggested in a long list of other genes as having a potential role in cell proliferation in metabolic and tumorous disease without the provision of any actual evidence.

In W02013/166264 PAPD5 has been suggested in a long list of other genes as having a potential role in increasing viral replication without the provision of any actual evidence.

In WO 2017/066712 down regulation of PAPD5 in relation to the treatment and diagnosis of telomere diseases has been described. Five shRNA structures for this purpose have been described.

To our knowledge the expression of PAPD5 or PAPD7 has never been associated with HBV infection.

Objective of the Invention

Thus, the technical problem underlying the present invention is the identification and provision of ameliorated means and methods for treating and/or preventing a HBV infection.

The technical problem is solved by the provision of the embodiments described herein and characterized in the claims.

SUMMARY OF INVENTION

One aspect of the present invention relates to a screening method, particularly to a method for identifying a compound that prevents, ameliorates and/or inhibits a HBV infection, comprising:
(a) contacting a test compound with
(a1) PAPD5 polypeptide and/or PAPD7 polypeptide; or
(a2) a cell expressing PAPD5 and/or PAPD7;
(b) measuring the expression and/or activity of PAPD5 and/or PAPD7 in the presence and absence of said test compound; and
(c) identifying a compound that reduces the expression and/or activity of PAPD5 and/or PAPD7 as a compound that prevents, ameliorates and/or inhibits a HBV infection.

A further aspect of the invention is a method for identifying a compound that prevents, ameliorates and/or inhibits a HBV infection, comprising:
(a) contacting a test compound with
  (i) PAPD5 and/or PAPD7 polypeptide; or
  (ii) a cell expressing PAPD5 and/or PAPD7;
(b) measuring whether the test compound binds to the PAPD5 and/or to PAPD7 polypeptide;
(c) measuring whether the test compound inhibits propagation of HBV; and
(d) identifying a compound that binds to PAPD5 and/or PAPD7 polypeptide and inhibits propagation of HBV as a compound that prevents, ameliorates and/or inhibits a HBV infection.

A further aspect of the present invention is an inhibitor of PAPD5 and/or PAPD7 for use in treating and/or preventing a HBV infection, wherein said inhibitor is
(a) a small molecule that binds to PAPD5 and/or PAPD7; or
(b) an antibody that specifically binds to PAPD5 and/or PAPD7.

The inhibitor for the use in treating or preventing HBV can be selected from compounds of Formula (I) or (II). In particular the inhibitors of Formula (III) and (IV) are usedul in the invention.

DETAILED DESCRIPTION OF THE INVENTION

Figure 1:
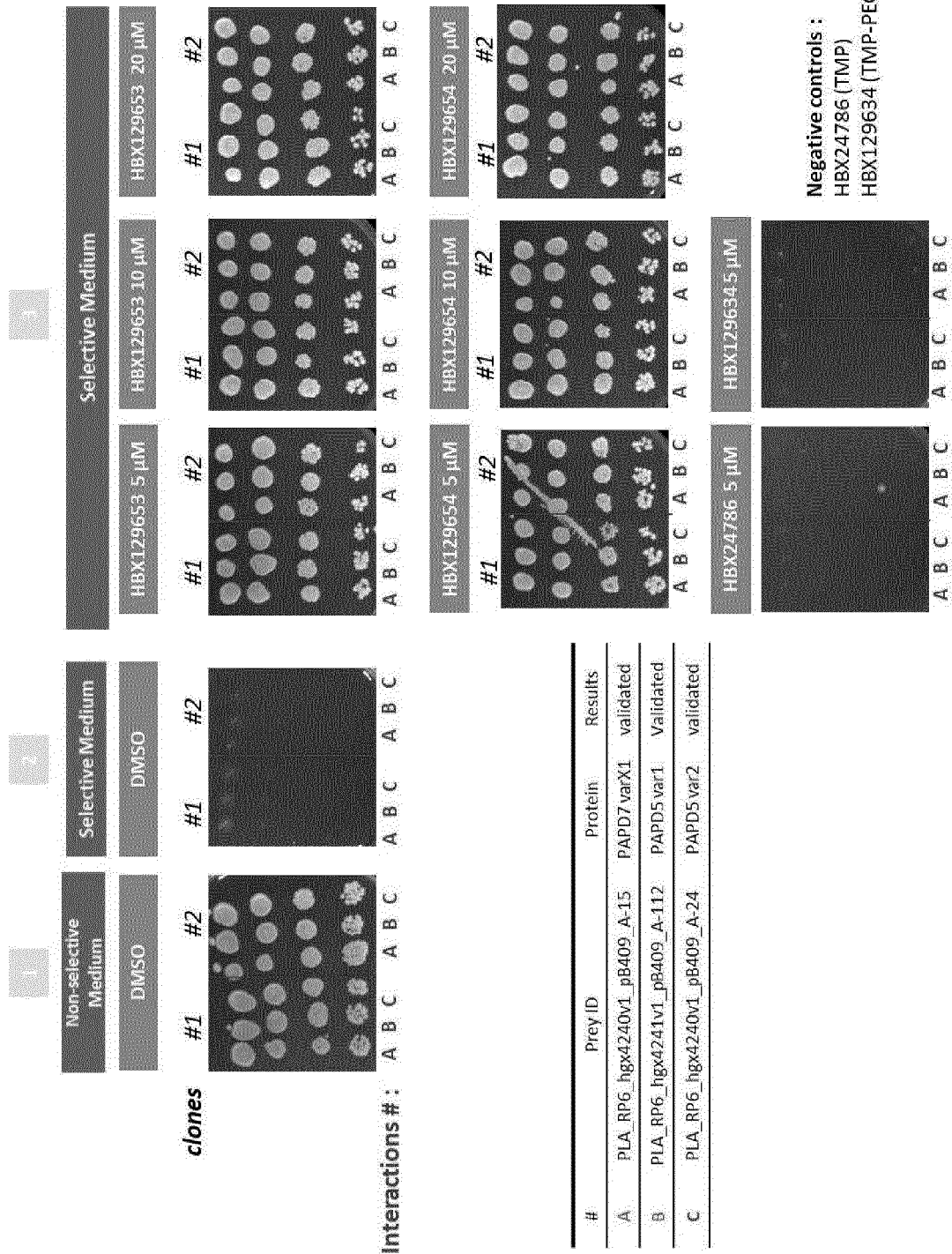
FIG. 1: Pictures from 1-by-1 experiment with HBX129653/HBX129654 chemical probes and the 3 prey fragments.

PAPD5 and PAPD7 are non-canonical poly(A)-polymerases that belong to the superfamily of polymerase β-like nucleotidyl transferases. In context of the present invention it has surprisingly been shown that a compound that is useful for the therapeutic intervention of a HBV infection can successfully be identified by analyzing whether a test compound inhibits PAPD5 and/or PAPD7. Or, in other words, inhibition of PAPD5 and/or PAPD7 was identified in the appended examples as being an indicator for the efficacy of a compound to inhibit a HBV infection. The appended examples demonstrate that a dihydroquinolizinone compound having the formula (III) as shown herein below (herein called DHQ) and a tetrahydropyridopyrimidine compound having the formula (IV) as shown herein below (herein called THP) bind to PAPD5 and PAPD7 polypeptides. These compounds have the capacity to inhibit production of HBV surface antigen (HBsAg) and the expression of HBV RNA during HBV infection (WO 2015/113990 A1 and WO2016/177655). In addition, the appended examples show that inhibition of PAPD5 and/or PAPD7 by using siRNA leads to an inhibition of viral expression, particularly of the secretion of HBsAg and HBeAg as well as of the production of intracellular HBV mRNA. These results directly indicate that by reducing the amount and/or activity (e.g. the amount) of PAPD5 and/or PAPD7 an HBV infection (e.g. a chronic HBV infection) can be prevented or treated (i.e. ameliorated and/or inhibited). Thus, the present invention relates to a screening method, wherein a compound that reduces the expression and/or activity (e.g. the expression) of PAPD5 and/or PAPD7 (e.g. of PAPD5 and PAPD7) is identified as a compound that prevents and/or treats (i.e. ameliorates and/or inhibits) a HBV infection.

It has been found in context of the present invention that a compound antagonizes (i.e. inhibits) PAPD5 and/or PAPD7 leads to inhibition of HBV gene expression and replication; and thus, prevents, ameliorates and/or inhibits a HBV infection. Such a compound may lead to a reduction of the PAPD5 and/or PAPD7 expression and/or activity of 10-100%, preferably of 20-100%, more preferably of 30-100%, even more preferably of 40-100%, even more preferable of 50-100%, even more preferably of 60-100%, even more preferably of 70-100%, even more preferably of 80-100%, and most preferably of 90-100%.

In the herein provided screening method it is envisaged that the expression of PAPD5 and/or PAPD7 is measured (i.e. analyzed/determined) by using in step (a) a cell expressing PAPD5 and/or PAPD7, i.e. (ai). The activity of PAPD5 and/or PAPD7 may be measured (i.e. analyzed/determined) by using in step (a) either (ai) PAPD5 and/or PAPD7 polypeptide, e.g. in a cell-free preparation; or (aii) a cell expressing PAPD5 and/or PAPD7.

In one aspect of the invention, a compound that reduces the expression of PAPD5 and/or PAPD7 (e.g. of PAPD5, preferably of PAPD5 and PAPD7) is identified as a compound that prevents, ameliorates and/or inhibits (i.e. treats) HBV infection. In another aspect of the invention a compound that reduces the activity of PAPD5 and/or PAPD7 (e.g. of PAPD5, preferably of PAPD5 and PAPD7) is identified as a compound that prevents, ameliorates and/or inhibits (i.e. treats) a HBV infection. It is prioritized that a compound that reduces the expression and/or activity of PAPD5 or of both molecules, PAPD5 and PAPD7, is identified as a compound that prevents, ameliorates and/or inhibits a HBV infection. Most preferably, a compound that reduces the expression and/or activity of both molecules, PAPD5 and PAPD7, is identified as a compound that prevents, ameliorates and/or inhibits a HBV infection.

In accordance with the present invention a compound that prevents and/or treats (i.e. ameliorates and/or inhibits) a HBV infection can be identified (i.e. selected) by performing a first pre-selection step in order to identify a compound that binds to PAPD5 and/or PAPD7. Subsequently, in a second step, it may be evaluated whether a compound that has been identified as binding to PAPD5 and/or PAPD7 inhibits propagation of HBV. Thus, the present invention relates to a further screening method, wherein a compound that binds to PAPD5 and/or PAPD7 (e.g. to PAPD5 and PAPD7) and inhibits propagation of HBV is identified as a compound that prevents, ameliorates and/or inhibits (i.e. treats) a HBV infection.

Thus, the invention relates to a method for identifying a compound that prevents, ameliorates and/or inhibits a HBV infection, comprising:
(a) contacting a test compound with
(ai) PAPD5 polypeptide and/or PAPD7 polypeptide; or
(aii) a cell expressing PAPD5 and/or PAPD7;
(b) measuring whether the test compound binds to PAPD5 and/or to PAPD7;
(c) measuring whether the test compound inhibits propagation of HBV; and
(d) identifying a compound that binds to PAPD5 and/or PAPD7 and inhibits propagation of HBV as a compound that prevents, ameliorates and/or inhibits a HBV infection.

Thus, in accordance with the present invention a compound that binds to PAPD5 and/or PAPD7 (e.g. to PAPD5, preferably to PAPD5 and PAPD7) and inhibits propagation of HBV is identified as a compound that prevents, ameliorates and/or inhibits (i.e. treats) a HBV infection. It is prioritized that a compound that (i) binds to PAPD5, or that binds to both molecules, PAPD5 and PAPD7; and (ii) inhibits propagation of HBV, is identified as a compound that prevents, ameliorates and/or inhibits a HBV infection. Most preferably, a compound that binds to both molecules, PAPD5 and PAPD7, and inhibits propagation of HBV, is identified as a compound that prevents, ameliorates and/or inhibits a HBV infection.

The above described screening methods lead to the identification of a compound that prevents, ameliorates and/or inhibits a HBV infection. It is prioritized that said compounds ameliorates and/or inhibits (i.e. treats) a HBV infection. Thus, the herein provided screening methods are useful in the identification of a compound that treats a HBV infection.

In the context of the present invention, PAPD5 may be the PAPD5 polypeptide or the PAPD5 mRNA. It is prioritized in context of the screening methods provided herein that PAPD5 is the PAPD5 polypeptide. One aspect of the present invention relates to the herein provided screening methods, wherein the PAPD5 polypeptide is a polypeptide comprising or consisting of
(a) the amino acid sequence of SEQ ID NO: 1 or 2;
(b) an amino acid sequence having at least 80%, preferably at least 90%, more preferably at least 95%, even more preferably at least 98%, and even more preferably at least 99% identity to an amino acid sequence of (a), wherein the polypeptide has poly-A polymerase function;
(c) the amino acid sequence of an enzymatically active fragment of SEQ ID NO: 1 or 2; or
(d) an amino acid sequence having at least 80%, preferably at least 90%, more preferably at least 95%, even more preferably at least 98%, and even more preferably at least 99% identity to an amino acid sequence of (d), wherein the polypeptide has poly-A polymerase function.

Examples for enzymatically active fragments of SEQ ID NO: 1 or 2 (i.e. of PAPD5) are the nucleotidyltransferase domain at positions 145-256 of SEQ ID NO: 1 or 2, or the Cid1 poly A polymerase at positions 308-368 of SEQ ID NO: 1 or 2.

Another aspect of the present invention relates to the herein provided screening methods, wherein the cells expressing PAPD5 contain PAPD5 mRNA, a polynucleotide comprising or consisting of
(i) the nucleotide sequence encoding the amino acid sequence of SEQ ID NO: 1 or 2;
(ii) a nucleotide sequence encoding an amino acid sequence having at least 80%, preferably at least 90%, more preferably at least 95%, even more preferably at least 98%, and even more preferably at least 99% identity to SEQ ID NO: 1 or 2, wherein the polynucleotide encodes a polypeptide that has poly-A polymerase function;
(iii) the nucleotide sequence encoding an enzymatically active fragment of SEQ ID NO: 1 or 2;
(iv) a nucleotide sequence encoding an amino acid sequence having at least 80%, preferably at least 90%, more preferably at least 95%, even more preferably at least 98%, and even more preferably at least 99% identity to an amino acid sequence of an enzymatically active fragment of SEQ ID NO: 1 or 2, wherein the polynucleotide encodes a polypeptide that has poly-A polymerase function;
(v) a nucleotide sequence comprising or consisting of SEQ ID NO: 4 or 5; or
(vi) a nucleotide sequence having at least 80%, preferably at least 90%, more preferably at least 95%, even more preferably at least 98%, and even more preferably at least 99% identity to SEQ ID NO: 4 or 5, wherein the polypeptide expressed from the sequence has poly-A polymerase function; or
(vii) a pre-mRNA that whe processed (i.e. spliced) leads to a polynucleotide of (v) or (vi).

In preferred embodiments, the PAPD5 mRNA may be a polynucleotide comprising or consisting of the nucleotide sequence of SEQ ID NO: 4 or 5. However, the PAPD5 mRNA may also be a polynucleotide comprising or consisting of a nucleotide sequence having at least 80%, preferably at least 90%, more preferably at least 95%, even more preferably at least 98%, and even more preferably at least 99% identity to SEQ ID NO: 4 or 5, wherein the polynucleotide encodes a polypeptide that has poly-A polymerase function.

In context of the present invention PAPD7 may be the PAPD7 polypeptide or the PAPD7 mRNA. It is prioritized in context of the screening methods provided herein that PAPD7 is the PAPD7 polypeptide. One aspect of the present invention relates to the herein provided screening methods, wherein the PAPD7 polypeptide is a polypeptide comprising or consisting of
(a) the amino acid sequence of SEQ ID NO: 3;
(b) an amino acid sequence having at least 80%, preferably at least 90%, more preferably at least 95%, even more preferably at least 98%, and even more preferably at least 99% identity to an amino acid sequence of (a), wherein the polypeptide has poly-A polymerase function;
(c) the amino acid sequence of an enzymatically active fragment of SEQ ID NO: 3; or
(d) an amino acid sequence having at least 80%, preferably at least 90%, more preferably at least 95%, even more preferably at least 98%, and even more preferably at least 99% identity to an amino acid sequence of (c), wherein the polypeptide has poly-A polymerase function.

Examples for enzymatically active fragments of SEQ ID NO: 3 (i.e. of PAPD7) are the nucleotidyltransferase domain at positions 15-125 of SEQ ID NO: 3; or the Cid1 family poly A polymerase at positions 178-238 of SEQ ID NO: 3.

Another aspect of the present invention relates to the herein provided screening methods, wherein the cells expressing PAPD7 contain PAPD7 mRNA, a polynucleotide comprising or consisting of
(i) the nucleotide sequence encoding the amino acid sequence of SEQ ID NO: 3;
(ii) a nucleotide sequence encoding an amino acid sequence having at least 80%, preferably at least 90%, more preferably at least 95%, even more preferably at least 98%, and even more preferably at least 99% identity to SEQ ID NO: 3, wherein the polynucleotide encodes a polypeptide that has poly-A polymerase function;
(iii) the nucleotide sequence encoding an enzymatically active fragment of SEQ ID NO: 3; or
(iv) a nucleotide sequence encoding an amino acid sequence having at least 80%, preferably at least 90%, more preferably at least 95%, even more preferably at least 98%, and even more preferably at least 99% identity to an amino acid sequence of an enzymatically active fragment of SEQ ID NO: 3, wherein the polynucleotide encodes a polypeptide that has poly-A polymerase function; or
(v) a nucleotide sequence comprising or consisting of SEQ ID NO: 6; or
(vi) a nucleotide sequence having at least 80%, preferably at least 90%, more preferably at least 95%, even more preferably at least 98%, and even more preferably at least 99% identity to SEQ ID NO: 6, wherein the polypeptide expressed from the sequence has poly-A polymerase function; or
(vii) a pre-mRNA that whe processed (i.e. spliced) leads to a polynucleotide of (v) or (vi).

In preferred embodiments, the PAPD7 mRNA may be a polynucleotide comprising or consisting of the nucleotide sequence of SEQ ID NO: 6. However, the PAPD7 mRNA may also be a polynucleotide comprising or consisting of a nucleotide sequence having at least 80%, preferably at least 90%, more preferably at least 95%, even more preferably at least 98%, and even more preferably at least 99% identity to SEQ ID NO: 6, wherein the polynucleotide encodes a polypeptide that has poly-A polymerase function.

In context of the present invention said cell may be a eukaryotic cell. For example, said cell may be a yeast cell or a vertebrate cell. Vertebrate cells include fish, avian, reptilian, amphibian, marsupial, and mammalian cells. Preferably, the cell is a mammalian cell, most preferably, a human cell. Mammalian cells also include feline, canine, bovine, equine, caprine, ovine, porcine murine, such as mice and rat, and rabbit cells. In the herein provided screening methods, the "cell" may endogenously express PAPD5 and/or PAPD7 or overexpress PAPD5 and/or PAPD7. For overexpressing PAPD5 and/or PAPD7 the cell may comprise the nucleotide sequence encoding the PAPD5 polypeptide and/or the PAPD7 polypeptide within an expression vector. In preferred embodiments the cell comprise a nucleotide sequence encoding the PAPD5 polypeptide and a nucleotide sequence encoding the PAPD7 polypeptide. The cell of the herein provided screening methods may be comprised in a non-human animal, e.g. a mouse, rat, rabbit or ferret.

In the above described screening method wherein the binding to PAPD5 and/or PAPD7 is measured, a compound may be identified as a compound that binds to PAPD5 polypeptide and/or PAPD7 polypeptide if it has a particular binding affinity to PAPD5 and/or PAPD7. For example, the compound that binds to PAPD5 and/or PAPD7 may have a dissociation constant (Kd) in the micromolar range; or, preferably, in the range of 100 nM to 1 pM.

In context of the present invention it may be measured (i.e. analyzed) whether the test compound specifically binds to PAPD5 polypeptide and/or PAPD7 polypeptide, i.e. whether the test compound exclusively or predominately binds to PAPAD5 and/or PAPD7. For example, it may be measured whether the test compound specifically binds to PAPD7. Preferably, it is measured whether the test compound specifically binds to PAPD5. More preferably it is measured whether the test compound binds to both, PAPD5 and PAPD7. For example, it may be measured whether the test compound specifically binds to PAPD5 and PAPD7.

For example, in the herein provided screening methods, binding of the test compound to PAPD5 and/or PAPD7 may be measured by conducting a yeast 3 hybrid screen. The Y3H system is a modified version of the yeast two-hybrid (Y2H) system adapted for the detection of drug-protein interactions. It requires coupling of the drug of interest with a ligand that can be anchored to a DNA-binding protein inside yeast cells. The interaction of the anchored drug with a target protein is then detected by linking their association to the transcriptional activation of a reporter gene; see, e.g. Johnsson, Nature Chem Bio, 2011, 7: 375-383; and Licitra, Proc Natl Acad Sci USA, 1996, 12; 93(23):12817-21. In such a yeast 3 hybrid screen an inactive free compound may be used for competition against the labeled test compound.

Binding of a test compound to PAPD5 and/or PAPD7 may also be measured by using Biacore, ChemoProteomics, or Microscale Thermophoresis.

A compound that inhibits the propagation of HBV may be a compound that reduces the expression of viral RNA, that reduces the production of viral DNA (HBV DNA) deriving from viral RNA (HBV RNA), that reduces the production of new viral particles (HBV particles), and/or that produces production and/or secretion of HBsAg and/or HBeAg. Thus, one aspect of the present invention relates to the herein provided screening methods, wherein the compound that inhibits propagation of HBV inhibits secretion of HBsAg, inhibits secretion of HBeAg, and/or inhibits production of intracellular HBV mRNA or HBV DNA. Preferably, a compound that inhibits the propagation of HBV is a compound that inhibits secretion of HBsAg, secretion of HBeAg and production of intracellular HBV mRNA.

For example, a compound that inhibits propagation of HBV may reduce the expression of viral RNA (HBV RNA), the production of viral DNA (HBV DNA) deriving from viral RNA, the production of new viral particles (HBV particles), the production and/or secretion of HBsAg and/or HBeAg by 10-100%, preferably by 20-100%, more preferably by 30-100%, even more preferably by 40-100%, even more preferable by 50-100%, even more preferably by 60-100%, even more preferably by 70-100%, even more preferably by 80-100%, and most preferably by 90-100%, when compared the untreated cells or animals or cell or animal treated with an appropriate control.

The herein provided screening methods may additionally comprise the step of comparing the test compound to a control. Said control may be an inactive test compound, wherein said inactive test compound is a compound that:
(i) does not reduce the expression and/or activity of PAPD5 and/or PAPD7; and/or
(ii) does not bind to PAPD5 and/or PAPD7 and does not inhibit propagation of HBV.

This inactive test compound has no activity against HBV, e.g. it does not lead to inhibition of secretion of HBsAg and HBeAg and to inhibition of production of intracellular HBV mRNA. For example, the inactive test compound may have an $IC_{50}$ value in the inhibition of HBsAg of more than 3 µM. In the herein provided screening method, the inactive test compound may be the compound "DHQ compound—inactive" or the compound "THP compound—inactive" as defined in the appended examples. In the screening method wherein expression and/or activity of PAPD5 and/or PAPD7 is measured, the test compound as defined above in (i) may be used. Alternatively, in the screening method wherein binding to PAPD5 and/or PAPD7 is measured, the test compound as defined above in (ii) may be used. An inactive compound can be designed from an active one, e.g., by chemical modification and/or chiral separation.

In the herein provided screening methods, the activity of PAPD5 and/or PAPD7 in the presence and absence of the test compound may be measured, e.g. by monitoring the in vitro polyadenylation of mRNA, e.g., as described in Rammelt, RNA, 2011, 17:1737-1746. In brief, a ribo-oligonucleotide $A_{15}$ may be incubated with recombinant PAPD5 protein expressed in *Escherichia coli* in the presence of ATP(A), CTP (C), GTP(G), UTP(U), or a mixture of all four dNTPs, respectively.

The expression of PAPD5 and/or PAPD7 in the presence and absence of the test compound may be measured, e.g. by using (q)PCR, western blot, or MassSpec.

Inhibition of propagation of HBV may be measured, e.g., by measuring whether the test compound has the activity to inhibit secretion of HBsAg and/or of HBeAg, and/or to inhibit production of intracellular HBV mRNA. Inhibition of secretion of HBsAg and/or HBeAg may be measured by ELISA, e.g. by using the CLIA ELISA Kit (Autobio Diagnostic) according to the manufacturers' instructions. Inhibition of production of intracellular HBV mRNA may be measured by real-time PCR, e.g. as described in the appended examples. Further methods for evaluating whether a test compound inhibits propagation of HBV are measuring secretion of HBV DNA by RT-qPCR e.g. as described in WO 2015/173208; Northern Blot; in-situ hybridization, or immuno-fluorescence.

For performing the herein provided screening methods publicly or commercially available molecule libraries may be used. Thus, in context of the invention the said test compound may be
(i) a small molecule of a screening library; or
(ii) a peptide of a phage display library, of an antibody fragment library, or derived from a cDNA library.

For example, the cDHA Human Liver (HLV) library or the cDNA Human Placenta (PLA) library of Hybrigenics Services SAS may be used.

In the herein provided screening method wherein the activity of PAPD5 polypeptide and/or PAPD7 polypeptide is measured, said activity of PAPD5 and PAPD7 is preferably the poly-A polymerase function (i.e. the poly-A polymerase activity). The poly-A polymerase function/activity of a polypeptide (e.g. of PAPD5 or PAPD7) may be measured, e.g. by monitoring the in vitro polyadenylation of mRNA, e.g. as described in Rammelt, RNA, 2011, 17:1737-1746. This method can also be used to measure the poly-A polymerase function of PAPD5 and/or PAPD7 in the presence and absence of a test compound.

The appended examples demonstrate that by inhibiting PAPD5 and/or PDPD7 polypeptide, the secretion of HBsAg and HBeAg as well as production of intracellular HBV mRNA can effectively be inhibited. These data demonstrate that an inhibitor of PAPD5 and/or PAPD7 can be used to prevent and/or treat a HBV infection.

Several compounds that have a certain efficacy in the treatment of a HBV infection have been described in the art (see, e.g. WO 2015/113990 A1 and WO 2016/177655). However, in context of the present invention it has surprisingly been found that anti-HBV agents that are completely different in structure (e.g. DHQ and THP) surprisingly and specifically bind to PAPD5 and PAPD7. In addition, the prior art also encompass agents less active in the inhibition of HBsAg production. Such agents have been shown in the appended examples to have less binding affinity to PAPD5 and PAPD7 (see, e.g., "DHQ—inactive"). Indeed, the appended examples demonstrate a clear correlation between activity of the compound against a HBV infection and binding affinity towards PAPD5 and PAPD7. Thus, selectively using an anti-HBV agent that binds to PAPD5 and/or PAPD7 leads to particularly high anti-HBV efficacy. Furthermore, the present invention shows for the first time that a compound that inhibits PAPD5, PAPD7, or particularly PAPD5 and PAPD7 has an extraordinary high activity in terms of inhibition of secretion of HBsAg and HBeAg as well as of production of intracellular HBV mRNA. Reduction of secretion of HBsAg and HBeAg inhibits development of chronic HBV infection more effectively as compared to the reduction of secretion of HBsAg alone. In addition, inhibition of secresion of HBsAg and HBeAg reduces the infectiousness of a HBV infected person. Furthermore, reducing HBeAg in an expected mother may also inhibit the development of a chronic HBV infection of her child. Thus, the present invention unexpectedly demonstrates that selectively using compounds that inhibit PAPD5 and/or PAPD7 leads to an improved therapeutic success in the treatment of a HBV infection in terms of a considerably more effective reduction of HBsAg and HBeAg.

Accordingly, an aspect of the present invention is use of an inhibitor of PAPD5 and/or PAPD7 in the treatment of HBV infection, in particular a chronic HBV infection. In a further embodiment the invention relates to the use of an inhibitor of a PAPD5 and/or PAPD7 in reduction of the viral antigens HBsAg and HBeAg.

Thus, the present invention relates to an inhibitor of PAPD5 and/or PAPD7 for use in treating and/or preventing a HBV infection, wherein said inhibitor is
(i) a small molecule that binds to PAPD5 and/or PAPD7;
(ii) a RNA interference (RNAi) molecule against PAPD5 and/or PAPD7;
(iii) an antibody that specifically binds to PAPD5 and/or PAPD7; or
(iv) a genome editing machinery, comprising:
(a) a site-specific DNA nuclease or a polynucleotide encoding a site-specific DNA nuclease; and
(b) a guide RNA or a polynucleotide encoding a guide RNA.

The inhibitor of the present invention may also be a PAPD5 and/or PAPD7 specific locked nucleic acid (LNA) molecule.

It is envisaged that the inhibitor of the invention is used for treating (e.g. ameliorating) a HBV infection.

The inhibitor may be a molecule that specifically inhibits PAPD7. Preferably, the inhibitor is a molecule that specifically inhibits PAPD5. More preferably, the inhibitor inhibits both, PAPD5 and PAPD7. Thus, it is prioritized that the inhibitor of the present invention either inhibits PAPD5 or both, PAPD5 and PAPD7. Most preferably, the inhibitor of the present invention inhibits PAPD5 and PAPD7. In one aspect of the invention the inhibitor of the present invention inhibits both, PAPD5 and PAPD7 and leads to a reduction of secretion of HBsAg and/or HBeAg of at least 50% as compared to the no drug control (i.e. compared to cells or subjects to which no drug has been administrated).

The inhibitor of the present invention may have an $IC_{50}$ value in the inhibition of HBsAg and HBeAg of below 3 µM, preferably of below 2 µM, more preferably below 1 µM, more preferably below 0.1 µM, and most preferably below 0.01 µM.

Genome editing by using a site-specific DNA nuclease (such as Cas9 or Cpf1) and a guide RNA is commonly known in the art and described, e.g., in "CRISPR-Cas: A Laboratory Manual", 2016, edited by Jennifer Doudna, ISBN 978-1-621821-31-1.

For example, if said site-specific DNA nuclease is a Cas9 nuclease, then the genome editing machinery preferably further comprises:
(i) at least one guide RNA consisting of at least one target sequence specific CRISPR RNA (crRNA) molecule and at least one trans-activating crRNA (tracrRNA) molecule;
(ii) a polynucleotide encoding the RNA molecules of (i);
(iii) at least one guide RNA, which is a chimeric RNA molecule comprising at least one target sequence specific crRNA and at least one tracrRNA; or
(iv) a polynucleotide encoding the chimeric RNA of (iii).

In an alternative example the site-specific DNA nuclease is a Cpf1 nuclease, and the genome editing machinery preferably further comprises:
(i) at least one guide RNA comprising a target sequence specific CRISPR RNA (crRNA) molecule; or
(ii) a polynucleotide encoding the RNA molecules of (i).

The herein provided inhibitor of PAPD5 and/or PAPD7 may also be a genome editing machinery that comprises at least one pre-assembled Cas9 protein-guide RNA ribonucleoprotein complex (RNP).

Herein, the guide RNA is designed to target the genomic PAPD5 or PAPD7 DNA. Alternatively, several guide RNAs are used, so that the genomic DNA of PAPD5 and of PAPD7 can be targeted. Inhibition of PAPD5 and/or PAPD7 may be achieved by introducing frame-shift knockout mutations into the genomic PAPD5 and/or PAPD7 DNA through non-homologous end-joining (NHEJ), or by modifying the genomic PAPD5 and/or PAPD7 DNA through homology-directed repair (HDR). How these mechanisms can be induced is commonly known in the art and described, e.g., in Heidenreich, 2016, Nat Rev Neurosci 17 36-44.

The inhibitor of the present invention may be a naturally occurring molecule, e.g. a naturally occurring antibody or a naturally occurring RNAi molecule. However, the inhibitor of the present invention may also be a non-naturally occurring molecule. For example, the inhibitor of the invention may be an antibody having an amino acid sequence that is not identical to naturally occurring antibodies or may be an antibody comprising at least one non-naturally occurring amino acid residue such as synthetic amino acids providing similar side chain functionality. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-pbiphenylalanine D-or L-p-methoxybiphenylalanine, D- or L-2-indole(alkyl)alanines, and D- or Lalkylalanines wherein the alkyl group is selected from the group consisting of substituted or unsubstituted methyl, ethyl, propyl, hexyl, butyl, pentyl, isopropyl, iso-butyl, and iso-pentyl. Non-carboxylate amino acids can be made to possess a negative charge, as provided by phosphono-orsulfated amino acids, which are to be considered as non-limiting examples. Further non-natural amino acids are alkylated amino acids, made by combining an alkyl group with any natural amino acid. Basic natural amino acids such as lysine and arginine may be substituted with alkyl groups at the amine ($NH_2$) functionality. Yet other substitutions on non-natural amino acids include nitrile derivatives (e.g., containing a CN-moiety in place of the $CONH_2$ functionality) of asparagine or glutamine, and sulfoxide derivative of methionine.

Analogously, the inhibitor of the invention may be a RNAi molecule having a nucleotide sequence that is not identical to naturally occurring RNAi molecules or may be a RNAi molecule comprising at least one non-naturally occurring nucleotides, such as a oligonucleotide thiophosphate, a substituted ribo-oligonucleotide, a LNA molecule, a PNA molecule, a GNA (glycol nucleic acid) molecule, a TNA (threose nucleic acid) molecule, a morpholino polynucleotide, or a nucleic acid with a modified backbone such as polysiloxane, 2'-O-(2-methoxy) ethyl-phosphorothioate, or a nucleic acid with a substituent, such as methyl-, thio-, sulphate, benzoyl-, phenyl-, amino-, propyl-, chloro-, and methanocarbanucleoside, or a reporter molecule to facilitate its detection. The inhibitor of the invention may also be naturally occurring or a non-naturally occurring small molecule or genome editing machinery.

In context of the present invention, the herein provided inhibitor may
(i) bind to PAPD5 and/or PAPD7 polypeptide; and/or
(ii) inhibit expression and/or activity of PAPD5 and/or PAPD7.

For example, the inhibitor of the present invention may bind to PAPD5 polypeptide and inhibit activity of PAPD5 polypeptide. In another example, the inhibitor of the present invention binds to PAPD7 polypeptide and inhibits activity of PAPD7 polypeptide. It is prioritized herein that the inhibitor binds to both, PAPD5 and PAPD7 polypeptide and inhibits the activity of both, PAPD5 and PAPD7 polypeptide. The inhibitor of the present invention may inhibit the expression of PAPD5 or PAPD7; or may inhibit the expression of both, PAPD5 and PAPD7.

As described above, in context of the present invention it has been shown that a compound that inhibits PAPD5 and/or PAPD7 has a high activity in terms of inhibition of secretion of HBsAg and HBeAg as well as of production of intracellular HBV mRNA. Therefore, the inhibitor of the present invention reduces secretion of HBsAg and HBeAg. Due to the reduction of HBsAg secretion the inhibitor of the present invention inhibits development of chronic HBV infection. In particular, due to inhibition of HBeAg secretion, the inhibitor of the present invention more efficiently inhibits development of a chronic HBV infection as compared to a compound that only reduces secretion of HBsAg. In addition, reducing HBeAg in an expected mother may also inhibit the development of a chronic HBV infection of her child. Thus, due to the reduction of HBeAg secretion the inhibitor of the present invention inhibits development of a chronic HBV infection (such as development of a chronic HBV infection in the offspring of an HBV infected mother) and reduces the infectiousness of a HBV infected person. Accordingly, one aspect of the present invention related to the herein provided inhibitor, wherein the inhibitor reduces secretion of HBsAg and HBeAg. In line with this, a further aspect of the invention relates to the herein provided inhibitor, wherein the inhibitor inhibits development of chronic HBV infection and reduces the infectiousness of a HBV infected person. In a particular aspect of the invention, the herein provided inhibitor inhibits development of a chronic HBV infection in the offspring of a HBV infected mother. This mother is preferably HBeAg positive.

The subject to be treated with the inhibitor of the invention (or which prophylactically receives the inhibitor of the present invention) is preferably a human, more preferably a human patient who is HBsAg positive and/or HBeAg positive, even more preferably a human patient that is HBsAg positive and HBeAg positive. Said human patient may be an expected mother, e.g. an expected mother who is HBeAg positive and/or HBsAg positive, more preferably an expected mother who is HBeAg positive and HBsAg positive.

Compounds of the Invention

As described above, the inhibitor of the present invention may be a small molecule. For example, the inhibitor of the invention may be the compound of formula (I) or (II):

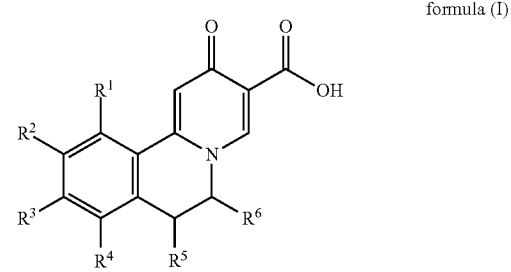

formula (I)

wherein
$R^1$ is hydrogen, halogen, $C_{1-6}$alkyl, $C_{1-6}$alkylamino or $C_{1-6}$alkoxy;
$R^2$ is hydrogen; halogen; $C_{1-6}$alkyl, which is unsubstituted or once, twice or three times substituted by fluoro; $C_{1-6}$alkoxy, which is unsubstituted or once, twice or three times substituted by fluoro; cyano; $C_{3-7}$cycloalkyl; hydroxy or phenyl-$C_xH_{2x}$—O—;
$R^3$ is hydrogen; halogen;
$C_{1-6}$alkyl, which is unsubstituted or once, twice or three times substituted by fluoro; cyano; pyrrolidinyl; amino; phenyl-$C_xH_{2x}$—N/$C_{1-6}$alkyl)-; $C_{1-6}$alkoxycarbonylpiperazinyl;
or $R^7$—O—, wherein $R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-8}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; cyano$C_{1-6}$alkyl; $C_{3-7}$cycloalkyl$C_{1-6}$alkyl; cyano$C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; di$C_{1-6}$alkylamino$C_{1-6}$alkoxy$C_{1-6}$alkyl; carboxy$C_{1-6}$alkyl; or $C_{1-6}$alkoxycarbonylamino$C_{1-8}$alkyl; heteroaryl$C_{1-6}$alkyl, wherein heteroaryl is N-containing monocyclic heteroaryl; or heterocycloalkyl$C_{1-6}$alkyl, wherein heterocycloalkyl is monocyclic heterocycloalkyl;

$R^4$ is hydrogen, halogen, $C_{1-6}$alkyl, cyano or $C_{1-6}$alkoxy; provided that $R^1$, $R^2$, $R^3$ and $R^4$ are not hydrogen simultaneously;

$R^5$ is hydrogen or $C_{1-6}$alkyl;

$R^6$ is hydrogen; $C_{1-6}$alkyl, which is unsubstituted or once, twice or three times substituted by fluoro; $C_{3-7}$cycloalkyl, which is unsubstituted or once, twice or three times substituted by fluoro or $C_{1-6}$alkyl; or phenyl-$C_xH_{2x}$—;

x is 1-6;

or a pharmaceutically acceptable salt, or an enantiomer thereof, or a diastereomer thereof;

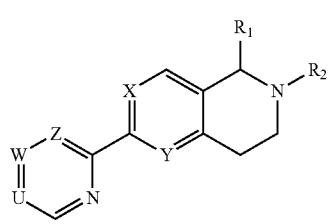

formula (II)

wherein $R^1$ is $C_{1-6}$alkyl, $C_{3-7}$cycloalkyl, halo$C_{1-6}$alkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl, di($C_{1-6}$alkoxycarbonyl)methylenyl, cyano$C_{1-6}$alkyl, $C_{3-7}$cycloalkyl$C_{1-6}$alkyl, phenyl$C_{1-6}$alkyl, $C_{1-6}$alkylsulfanyl$C_{1-6}$alkyl, $C_{1-6}$alkylsufonyl$C_{1-6}$alkyl, amino$C_{1-6}$alkyl, $C_{1-6}$alkylcarbonylamino$C_{1-6}$alkyl, $C_{1-6}$alkylsufonylamino$C_{1-6}$alkyl, $C_{1-6}$alkoxycarbonyl amino$C_{1-6}$alkyl, aminocarbonyl$C_{1-6}$alkyl, di$C_{1-6}$alkylamino- carbonyl$C_{1-6}$alkyl, monocyclic heterocycloalkyl$C_{1-6}$alkyl or imidazolyl$C_{1-6}$alkyl;

$R^2$ is aryl or heteroaryl, said aryl or heteroaryl being unsubstituted, or substituted by one, two, three or four substituents independently selected from $C_{1-6}$alkyl, $C_{3-7}$cycloalkyl, halogen, halo$C_{1-6}$alkyl, cyano, nitro, hydroxy, halo$C_{1-6}$alkoxy, —O—$C_xH_{2x}$—$R^3$, —O—$C_yH_{2y}$—$NHR^6$, —$NR^9R^{10}$, —$SO_2$—$R^{11}$, —$SO_2$—$NR^{12}R^{13}$, carboxy, $C_{1-6}$alkoxycarbonyl, —C(=O)—$NR^{12}R^{13}$, aryl, heteroaryl, monocyclic heterocycloalkyl and —O-monocyclic heterocycloalkyl; wherein monocyclic heterocycloalkyl is unsubstituted or substituted by $C_{1-6}$alkyl, $C_{3-7}$cycloalkyl, $C_{1-6}$alkylcarbonyl, $C_{1-6}$alkylsufonyl or $C_{1-6}$alkoxycarbonyl;

$R^3$ is hydrogen; $C_{3-7}$cycloalkyl; halo$C_{3-7}$cycloalkyl; hydroxy; hydroxy$C_{1-6}$alkyl$C_{3-7}$cycloalkyl; $C_{1-6}$alkoxy; monocyclic heterocycloalkyl; monocyclic heterocycloalkyl substituted by $C_{1-6}$alkyl, $C_{1-6}$alkylcarbonyl, $C_{1-6}$alkylsufonyl, $C_{3-7}$cycloalkyl or $C_{1-6}$alkoxycarbonyl; —C(=O)—$R^4$; $C_{1-6}$alkylsulfinyl; —$SO_2$—$R^5$; —C($NHR^7$)—C(=O)—$R^8$; carboxy$C_{1-6}$alkoxy or aminocarbonyl$C_{1-6}$alkoxy; wherein $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;

$R^5$ is $C_{1-6}$alkyl, $C_{3-7}$cycloalkyl, hydroxy, amino, $C_{1-6}$alkylamino or di$C_{1-6}$alkylamino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;

$R^9$ and $R^{10}$ are independently selected from hydrogen, $C_{1-6}$alkyl, $C_{3-7}$cycloalkyl, $C_{1-6}$alkylcarbonyl, $C_{1-6}$alkylsulfonyl, $C_{3-7}$cycloalkylcarbonyl and $C_{3-7}$cycloalkylsulfonyl; or $R^9$ and $R^{10}$ together with the nitrogen to which they are attached form monocyclic heterocycloalkyl;

$R^{11}$ is $C_{1-6}$alkyl, halo$C_{1-6}$alkyl, $C_{3-7}$cycloalkyl, halo$C_{3-7}$cycloalkyl, hydroxy$C_{1-6}$alkyl, $C_{1-6}$alkoxy$C_{1-6}$alkyl, halo$C_{1-6}$ alkoxy$C_{1-6}$alkyl, $C_{3-7}$cycloalkyl$C_{1-6}$alkyl, amino$C_{1-6}$alkyl, $C_{1-6}$alkylamino$C_{1-6}$alkyl, di$C_{1-6}$alkylamino$C_{1-6}$ alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, $C_{1-6}$alkylsulfenyl$C_{1-6}$alkyl, $C_{1-6}$alkylsulfanyl$C_{1-6}$alkyl or $C_{1-6}$alkylsulfonyl$C_{1-6}$alkyl;

$R^{12}$ and $R^{13}$ are independently selected from hydrogen, $C_{1-6}$alkyl, $C_{1-6}$alkoxy$C_{1-6}$alkyl, halo$C_{1-6}$alkyl, $C_{3-7}$cycloalkyl and halo$C_{3-7}$cycloalkyl; or $R^{12}$ and $R^{13}$ together with the nitrogen to which they are attached form monocyclic heterocycloalkyl;

x is 1, 2, 3, 4, 5, 6, 7 or 8;

y is 1, 2, 3, 4, 5, 6, 7 or 8;

U, W and Z are independently selected from CH and N;

one of X and Y is N, and the other one is CH or N;

or a pharmaceutically acceptable salt, or an enantiomer, or a diastereomer thereof.

In one aspect of the invention 6-methyl-2-oxo-9-pyrrolidin-1-yl-6,7-dihydrobenzo[a]quinolizine-3-carboxylic acid, 9-fluoro-6-methyl-2-oxo-6,7-dihydrobenzo[a]quinolizine-3-carboxylic acid, and 9,10-difluoro-6-methyl-2-oxo-6,7-dihydrobenzo[a]quinolizine-3-carboxylic acid are excluded from the compound of formula (I).

In one particular embodiment of the present invention the compounds of formulae (I) and (II) are excluded from the inhibitor of the present invention. Thus, one embodiment of the present invention relates to the inhibitor of the present invention, wherein said inhibitor is not a compound according to formula (I) or (II).

As described above, the appended examples demonstrate that the anti-HBV agents DHQ (i.e. a compound of formula (III)) and THP (i.e. a compound of formula (IV)) effectively bind to PAPD5 and PAPD7. Thus, it is prioritized in context of the invention that the inhibitor of the invention is the compound of formula (III) or (IV):

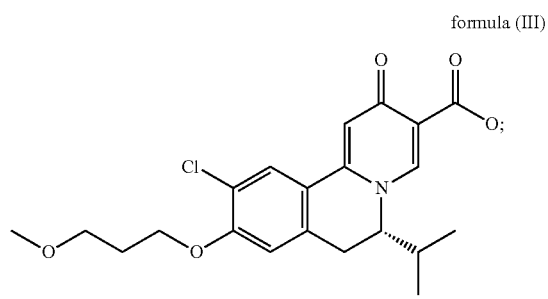

formula (III)

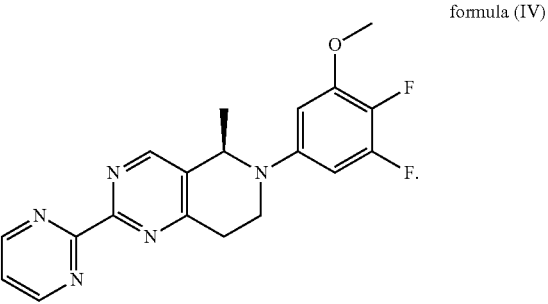

formula (IV)

In the appended examples also derivatives of the compounds of formulae (III) and (IV) having a linker and anchor ligand have been shown to have binding affinity to PAPD5 and PAPD7. These derivatives are shown below as formulae (V) and (VI), respectively. Thus, in one aspect of the present invention the inhibitor of the invention is the compound of formula (V) or (VI):

hydroxy-difluoropropyl-O—, hydroxybutyl-O—, hydroxypentyl-O—, hydroxyhexyl-O—, aminoethyl-O-propyl-O—, ethylamino-ethyl-O-propyl-O—, imidazolylethyl-O—, pyrazolylpropyl-O—, triazolylpropyl—, morpholinylethyl-O—, morpholinylpropyl-O—, (2-oxo-pyrrolidinyl)ethyl-O—, (2-oxo-pyrrolidinyl)propyl-O—, phenylmethyl-O—, phenylethyl-O—, pyrrolidinylethyl-

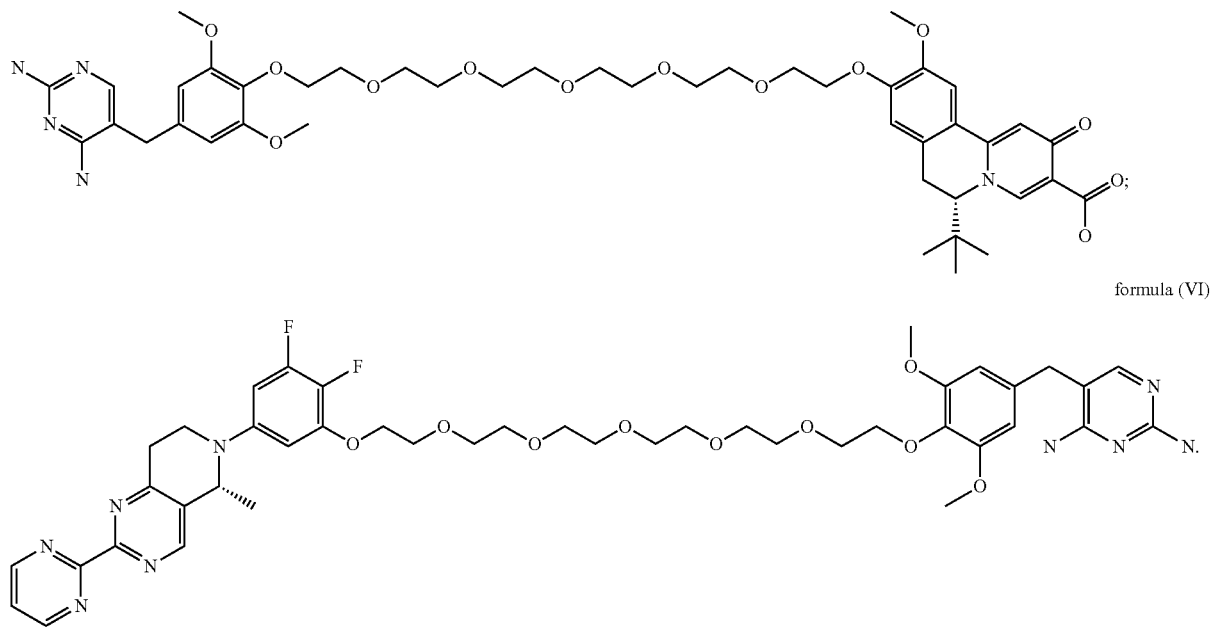

formula (V)

formula (VI)

In context of the present invention the inhibitor of the invention may be the compound according to formula (I), wherein the inhibitor is any one of the compounds as defined in items (1)-(19), below:

1. A compound according to formula (I), wherein
$R^1$ is hydrogen, fluoro, chloro, bromo, methyl, methylamino, methoxy or ethoxy;
$R^2$ is hydrogen, fluoro, chloro, bromo, methyl, ethyl, trifluoromethyl, methoxy, ethoxy, propoxy, trifluoromethoxy, cyano, cyclopropyl, hydroxy or phenylmethyl—O—;
$R^3$ is hydrogen, bromo, methyl, propyl, trifluoromethyl, cyano, phenylmethyl-N(methyl)-, tert-butoxycarbonylpiperazinyl, hydroxy, methoxy, ethoxy, propoxy, isopropoxy, butoxy, isobutoxy, difluoromethylmethyl-O—, difluoromethylethyl-O—, trifluoromethoxy, trifluoromethylmethyl-O—, trifluoromethylethyl-O—, ethyldifluoromethyl-O—, vinyldifluoromethyl-O—, propargyl-O—, hydroxymethylpropargyl-O—, methoxyethyl-O—, methoxypropyl-O—, methoxybutyl-O—, ethoxyethyl-O—, methoxyethyl-O-ethyl-O—, aminoethyl-O—, aminopentyl-O—, aminohexyl-O—, aminooctyl-O—, tert-butoxycarbonylaminopentyl-O—, tert-butoxycarbonylaminohexyl-O—, tert-butoxycarbonylaminooctyl-O—, methylcarbonylaminoethyl-O—, methylcarbonylaminopentyl-O—, methylsulfonylaminoethyl-O—, methylsulfonylaminopentyl-O—, methylsulfonylethyl-O—, methylsulfonylpropyl-O—, methylsulfanylpropyl-O—, cyanopropyl-O—, cyanocyclopropylmethyl-O—, cyclopropylmethyl-O—, cyclohexylethyl-O—, hydroxyethyl-O—, hydroxypropyl-O—, hydroxy-dimethylpropyl-O—, O—, pyrrolidinylpropyl-O—, pyrrolidinylcarbonylmethyl-O—, tetrahydropyranylmethyl-O— or carboxypropyl-O—;
$R^4$ is hydrogen, fluoro, chloro, bromo, methyl or cyano; provided that $R^1$, $R^2$, $R^3$ and $R^4$ are not hydrogen simultaneously;
$R^5$ is hydrogen or methyl;
$R^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl; or a pharmaceutically acceptable salt, or an enantiomer, or a diastereomer thereof.

2. A compound according to formula (I), wherein
$R^1$ is hydrogen, halogen, $C_{1-6}$alkylamino or $C_{1-6}$alkoxy;
$R^2$ is hydrogen, halogen, $C_{1-6}$alkyl, $C_{1-6}$alkoxy, $C_{3-7}$cycloalkyl, hydroxy or phenyl-$C_xH_{2x}$—O—;
$R^3$ is hydrogen; halogen; $C_{1-6}$alkyl; cyano; phenyl-$C_xH_{2x}$—N($C_{1-6}$alkyl)-; $C_{1-6}$alkoxycarbonylpiperazinyl; or $R^7$—O—, wherein $R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-8}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; cyano$C_{1-6}$alkyl; $C_{3-7}$cycloalkyl$C_{1-6}$alkyl; cyano$C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; carboxy$C_{1-6}$alkyl; $C_{1-6}$alkoxycarbonylaminoC$_{1-8}$alkyl; heteroarylC$_{1-6}$alkyl, wherein heteroaryl is N-containing monocyclic heteroaryl; or heterocycloalkylC$_{1-6}$alkyl, wherein heterocycloalkyl is monocyclic heterocycloalkyl;

R$^4$ is hydrogen, halogen, C$_{1-6}$alkyl or cyano; provided that R$^1$, R$^2$, R$^3$ and R$^4$ are not hydrogen simultaneously;

R$^5$ is hydrogen or C$_{1-6}$alkyl;

R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;

x is 1-6;

or a pharmaceutically acceptable salt, or enantiomer, or a diastereomer thereof.

3. A compound according to formula (I) or according to item 1 or 2, wherein

R$^1$ is hydrogen, fluoro, chloro, bromo, methylamino, methoxy or ethoxy;

R$^2$ is hydrogen, fluoro, chloro, methyl, ethyl, methoxy, ethoxy, propoxy, cyclopropyl, hydroxy or phenylmethyl-O—;

R$^3$ is hydrogen, bromo, methyl, propyl, cyano, phenylmethyl-N(methyl)-, tert-butoxycarbonylpiperazinyl, hydroxy, methoxy, ethoxy, propoxy, isopropoxy, butoxy, isobutoxy, difluoromethylmethyl-O—, difluoromethylethyl-O—, trifluoromethylmethyl-O—, ethyldifluoromethyl—O—, vinyldifluoromethyl-O—, propargyl-O—, hydroxymethylpropargyl-O—, methoxyethyl-O—, methoxypropyl-O—, methoxybutyl-O—, ethoxyethyl-O—, methoxyethyl-O-ethyl-O—, aminoethyl-O—, aminopentyl-O—, aminohexyl-O—, aminooctyl-O—, tert-butoxycarbonylaminopentyl-O—, tert-butoxycarbonylaminohexyl-O—, tert-butoxycarbonylaminooctyl-O—, methylcarbonylaminoethyl-O—, methylcarbonylaminopentyl-O—, methylsulfonylaminoethyl-O—, methylsulfonylaminopentyl-O—, methylsulfonylethyl-O—, methylsulfonylpropyl-O—, methylsulfanylpropyl-O—, cyanopropyl-O—, cyanocyclopropylmethyl-O—, cyclopropylmethyl-O—, cyclohexylethyl-O—, hydroxyethyl-O—, hydroxypropyl-O—, hydroxy-dimethylpropyl-O—, hydroxy-difluoropropyl-O—, hydroxybutyl-O—, hydroxypentyl-O—, hydroxyhexyl-O—, aminoethyl-O-propyl-O—, ethylamino-ethyl-O-propyl-O—, imidazolylethyl-O—, pyrazolylpropyl-O—, triazolylpropyl-O—, morpholinylethyl-O—, morpholinylpropyl-O—, (2-oxo-pyrrolidinyl)ethyl-O—, (2-oxo-pyrrolidinyl)propyl-O—, phenylmethyl-O—, phenylethyl-O—, pyrrolidinylethyl-O—, pyrrolidinylpropyl-O—, pyrrolidinylcarbonylmethyl-O—, tetrahydropyranylmethyl-O— or carboxypropyl-O—;

R$^4$ is hydrogen, chloro, bromo, methyl or cyano; provided that R$^1$, R$^2$, R$^3$ and R$^4$ are not hydrogen simultaneously;

R$^5$ is hydrogen or methyl;

R$^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl; or a pharmaceutically acceptable salt, or enantiomer, or a diastereomer thereof.

4. A compound according to formula (I) or item 2, wherein the compound is the compound of formula (IA):

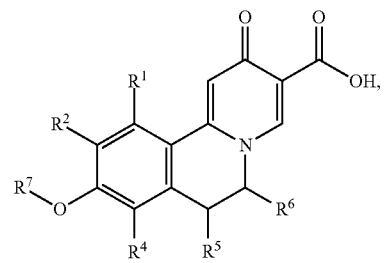

formula (IA)

wherein

R$^1$ is hydrogen, halogen or C$_{1-6}$alkoxy;

R$^2$ is hydrogen, halogen, C$_{1-6}$alkyl, C$_{1-6}$alkoxy, C$_{3-7}$cycloalkyl, hydroxy or phenyl-C$_x$H$_{2x}$—O—;

R$^4$ is hydrogen or halogen;

R$^5$ is hydrogen or C$_{1-6}$alkyl;

R$^6$ is hydrogen; C$_{1-6}$alkyl, which is unsubstituted or once, twice or three times substituted by fluoro; C$_{3-7}$cycloalkyl; C$_{1-6}$alkylC$_{3-7}$cycloalkyl; or phenyl-C$_x$H$_{2x}$—;

R$^7$ is hydrogen; C$_{1-6}$alkyl, which is unsubstituted or substituted with one to three substituents independently selected from fluoro, hydroxy and ethenyl; C$_{1-6}$alkoxyC$_{1-6}$alkyl; C$_{1-6}$alkoxyC$_{1-6}$alkoxyC$_{1-6}$alkyl; aminoC$_{1-8}$alkyl; C$_{1-6}$alkylcarbonylaminoC$_{1-8}$alkyl; C$_{1-6}$alkylsulfonylaminoC$_{1-8}$alkyl; C$_{1-6}$alkylsulfanylC$_{1-6}$alkyl; C$_{1-6}$alkylsulfonylC$_{1-6}$alkyl; cyanoC$_{1-6}$alkyl; C$_{3-7}$cycloalkylC$_{1-6}$alkyl; cyanoC$_{3-7}$cycloalkylC$_{1-6}$alkyl; phenylC$_{1-6}$alkyl; pyrrolidinylcarbonylC$_{1-6}$alkyl; C$_{2-6}$alkynyl; hydroxyC$_{1-6}$alkylC$_{2-6}$alkynyl; aminoC$_{1-6}$alkoxyC$_{1-6}$alkyl; C$_{1-6}$alkylaminoC$_{1-6}$alkoxyC$_{1-6}$alkyl; carboxyC$_{1-6}$alkyl; C$_{1-6}$alkoxycarbonylaminoC$_{1-8}$alkyl; heteroarylC$_{1-6}$alkyl, wherein heteroaryl is N-containing monocyclic heteroaryl; or heterocycloalkylC$_{1-6}$alkyl, wherein heterocycloalkyl is monocyclic heterocycloalkyl;

x is 1-6;

or a pharmaceutically acceptable salt, or enantiomer, or a diastereomer thereof.

5. A compound according to item 4, wherein

R$^1$ is hydrogen, fluoro, chloro or methoxy;

R$^2$ is hydrogen, fluoro, chloro, methyl, ethyl, methoxy, ethoxy, propoxy, cyclopropyl, hydroxy or phenylmethyl-O—;

R$^4$ is hydrogen or chloro;

R$^5$ is hydrogen or methyl;

R$^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl;

R$^7$ is hydrogen, methyl, ethyl, propyl, isopropyl, butyl, isobutyl, difluoromethylmethyl, difluoromethylethyl, trifluoromethylmethyl, ethyldifluoromethyl, vinyldifluoromethyl, propargyl, hydroxymethylpropargyl, methoxyethyl, methoxypropyl, methoxybutyl, ethoxyethyl, methoxyethyl-O-ethyl, aminoethyl, aminopentyl, aminohexyl, aminooctyl, tert-butoxycarbonylaminopentyl, tert-butoxycarbonylaminohexyl, tert-butoxycarbonylaminooctyl, methylcarbonylaminoethyl, methylcarbonylaminopentyl, methylsulfonylaminoethyl, methylsulfonylaminopentyl, methylsulfonylethyl, methylsulfonylpropyl, methylsulfanylpropyl, cyanopropyl, cyanocyclopropylmethyl, cyclopropylmethyl, cyclohexylethyl, hydroxyethyl, hydroxypropyl, hydroxy-dimethylpropyl, hydroxy-difluoropropyl, hydroxybutyl, hydroxypentyl, hydroxyhexyl, aminoethyl-O-propyl, ethylamino-ethyl-O-propyl-, imidazolylethyl, pyrazolylpropyl, triazolylpropyl, morpholinylethyl, morpholinylpropyl, (2-oxo-pyrrolidinyl)ethyl, (2-oxo-pyrrolidinyl)propyl, phenylmethyl, phenylethyl, pyrrolidinylethyl, pyrrolidinylpropyl, pyrrolidinylcarbonylmethyl, tetrahydropyranylmethyl or carboxypropyl; or a pharmaceutically acceptable salt, or enantiomer, or a diastereomer thereof.

6. A compound according to item 4, wherein
$R^1$ is hydrogen or halogen;
$R^2$ is $C_{1-6}$alkyl, halogen or $C_{3-7}$cycloalkyl;
$R^4$ is hydrogen;
$R^5$ is hydrogen or $C_{1-6}$alkyl;
$R^6$ is $C_{1-6}$alkyl or $C_{1-6}$alkyl$C_{3-7}$cycloalkyl;
$R^7$ is $C_{1-6}$alkyl, $C_{1-6}$alkoxy$C_{1-6}$alkyl; or phenyl$C_{1-6}$alkyl; or a pharmaceutically acceptable salt, or enantiomer, or a diastereomer thereof.

7. A compound according to item 6, wherein
$R^1$ is hydrogen, fluoro or chloro;
$R^2$ is methyl, ethyl, fluoro, chloro or cyclopropyl;
$R^4$ is hydrogen;
$R^5$ is hydrogen or methyl;
$R^6$ is methyl, ethyl, isopropyl, isobutyl, tert-butyl or methylcyclopropyl;
$R^7$ is methyl, ethyl, methoxyethyl, methoxypropyl or phenylmethyl; or a pharmaceutically acceptable salt, or enantiomer, or a diastereomer thereof.

8. A compound according to item 4, wherein
$R^1$ is hydrogen;
$R^2$ is $C_{1-6}$alkoxy;
$R^4$ is hydrogen or halogen;
$R^5$ is hydrogen or $C_{1-6}$alkyl;
$R^6$ is hydrogen; $C_{1-6}$alkyl, which is unsubstituted or once, twice or three times substituted by fluoro; $C_{3-7}$cycloalkyl; $C_{1-6}$alkyl$C_{3-7}$cycloalkyl; or phenyl-$C_xH_{2x}$—;
$R^7$ is hydrogen; $C_{1-6}$alkyl, which is unsubstituted or substituted with one to three substituents independently selected from fluoro, hydroxy and $C_{2-6}$alkenyl; $C_{1-6}$alkoxy$C_{1-6}$alkyl; $C_{1-6}$alkoxy$C_{1-6}$alkoxy$C_{1-6}$alkyl; amino$C_{1-8}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; cyano$C_{1-6}$alkyl; cyano$C_{3-7}$cycloalkyl$C_{1-6}$alkyl; $C_{3-7}$cycloalkyl$C_{1-6}$alkyl; phenyl$C_{1-6}$alkyl; pyrrolidinylcarbonyl$C_{1-6}$alkyl; $C_{2-6}$alkynyl; hydroxy$C_{1-6}$alkyl$C_{2-6}$alkynyl; amino$C_{1-6}$alkoxy$C_{1-6}$alkyl; $C_{1-6}$alkylamino$C_{1-6}$alkoxy$C_{1-6}$alkyl; carboxy$C_{1-6}$alkyl; $C_{1-6}$alkoxycarbonylamino$C_{1-8}$alkyl; imidazolyl$C_{1-6}$alkyl; pyrazolyl$C_{1-6}$alkyl; triazolyl$C_{1-6}$alkyl; morpholinyl$C_{1-6}$alkyl; (2-oxo-pyrrolidinyl)$C_{1-6}$alkyl; pyrrolidinyl$C_{1-6}$alkyl; or tetrahydropyranyl$C_{1-6}$alkyl;
x is 1-6;
or a pharmaceutically acceptable salt, or enantiomer, or a diastereomer thereof.

9. A compound according to item 8, wherein
$R^1$ is hydrogen;
$R^2$ is methoxy, ethoxy or propoxy;
$R^4$ is hydrogen or chloro;
$R^5$ is hydrogen or methyl;
$R^6$ is hydrogen, methyl, ethyl, propyl, isopropyl, isobutyl, tert-butyl, trifluoromethyl, trifluoromethylmethyl, cyclopropyl, cyclobutyl, methylcyclopropyl or phenylmethyl;
$R^7$ is hydrogen, methyl, ethyl, propyl, isopropyl, butyl, isobutyl, difluoromethylmethyl, difluoromethylethyl, trifluoromethylmethyl, ethyldifluoromethyl, vinyldifluoromethyl, propargyl, hydroxymethylpropargyl, methoxyethyl, methoxypropyl, methoxybutyl, ethoxyethyl, methoxyethyl-O-ethyl, aminoethyl, aminohexyl, aminooctyl, tert-butoxycarbonylaminopentyl, tert-butoxycarbonylaminohexyl, tert-butoxycarbonylaminooctyl, methylcarbonylaminoethyl, methylcarbonylaminopentyl, methylsulfonylaminoethyl, methylsulfonylaminopentyl, methylsulfonylethyl, methylsulfonylpropyl, methylsulfanylpropyl, cyanopropyl, cyanocyclopropylmethyl, cyclopropylmethyl, cyclohexylethyl, hydroxyethyl, hydroxypropyl, hydroxy-dimethylpropyl, hydroxy-difluoropropyl, hydroxybutyl, hydroxypentyl, hydroxyhexyl, aminoethyl-O-propyl, ethylamino-ethyl-O-propyl-, imidazolylethyl, pyrazolylpropyl, triazolylpropyl, morpholinylethyl, morpholinylpropyl, (2-oxo-pyrrolidinyl)ethyl, (2-oxo-pyrrolidinyl)propyl, phenylmethyl, phenylethyl, pyrrolidinylethyl, pyrrolidinylpropyl, pyrrolidinylcarbonylmethyl, tetrahydropyranylmethyl or carboxypropyl; or a pharmaceutically acceptable salt, or enantiomer, or a diastereomer thereof.

10. A compound according to item 4, wherein
$R^1$ is hydrogen or halogen;
$R^2$ is halogen, $C_{1-6}$alkyl, $C_{1-6}$alkoxy or $C_{3-7}$cycloalkyl;
$R^4$ is hydrogen;
$R^5$ is hydrogen or $C_{1-6}$alkyl;
$R^6$ is $C_{1-6}$alkyl, which is unsubstituted or once, twice or three times substituted by fluoro; $C_{3-7}$cycloalkyl or $C_{1-6}$alkyl$C_{3-7}$cycloalkyl;
$R^7$ is $C_{1-6}$alkyl, which is unsubstituted or substituted with one to three substituents independently selected from fluoro and hydroxy; $C_{1-6}$alkoxy$C_{1-6}$alkyl; amino$C_{1-8}$alkyl; $C_{1-6}$alkylcarbonylamino$C_{1-8}$alkyl; $C_{1-6}$alkylsulfonylamino$C_{1-8}$alkyl; $C_{1-6}$alkylsulfanyl$C_{1-6}$alkyl; $C_{1-6}$alkylsulfonyl$C_{1-6}$alkyl; $C_{3-7}$cycloalkyl$C_{1-6}$alkyl; phenyl$C_{1-6}$ alkyl; $C_{1-6}$alkylamino$C_{1-6}$alkoxy$C_{1-6}$alkyl; $C_{1-6}$alkoxycarbonylamino$C_{1-8}$alkyl; morpholinyl$C_{1-6}$alkyl or tetrahydropyranyl$C_{1-6}$alkyl; or a pharmaceutically acceptable salt, or enantiomer, or a diastereomer thereof.

11. A compound according to item 10, wherein
$R^1$ is hydrogen, fluoro, or chloro;
$R^2$ is fluoro, chloro, methyl, ethyl, methoxy, ethoxy or cyclopropyl;
$R^4$ is hydrogen;
$R^5$ is hydrogen or methyl;
$R^6$ is methyl, ethyl, isopropyl, isobutyl, tert-butyl, trifluoromethylmethyl, cyclobutyl or methylcyclopropyl;
$R^7$ is methyl, ethyl, propyl, butyl, isobutyl, cyclopropylmethyl, difluoromethylmethyl, difluoroethylmethyl, difluoromethylethyl, trifluoromethylmethyl, ethyldifluoromethyl, methoxyethyl, methoxypropyl, ethoxyethyl, aminohexyl, aminooctyl, tert-butoxycarbonylaminopentyl, tert-butoxycarbonylaminooctyl, methylcarbonylaminopentyl, methylsulfonylaminopentyl, methylsulfonylpropyl, methylsulfanylpropyl, hydroxypropyl, hydroxy-dimethylpropyl, hydroxy-difluoropropyl, hydroxybutyl, hydroxypentyl, hydroxyhexyl, ethylamino-ethyl-O-propyl-, morpholinylethyl, morpholinylpropyl, phenylmethyl or tetrahydropyranylmethyl; or a pharmaceutically acceptable salt, or enantiomer, or a diastereomer thereof.

12. A compound according to formula (I), item 1 or item 2, or a pharmaceutically acceptable salt, or enantiomer thereof, wherein $R^1$ is hydrogen.

13. A compound according to formula (I), item 1 or item 2, or a pharmaceutically acceptable salt, or enantiomer thereof, wherein $R^2$ is halogen or $C_{1-6}$alkoxy.

14. A compound according to formula (I), item 1 or item 2, or a pharmaceutically acceptable salt, or enantiomer thereof, wherein $R^2$ is chloro or methoxy.

15. A compound according to formula (I), item 1 or item 2, or a pharmaceutically acceptable salt, or enantiomer thereof, wherein $R^5$ is hydrogen.

16. A compound according to formula (I), item 1 or item 2, or a pharmaceutically acceptable salt, or enantiomer thereof, wherein $R^6$ is $C_{1-6}$alkyl or $C_{1-6}$alkyl$C_{3-7}$cycloalkyl.

17. A compound according to formula (I), item 1 or item 2, or a pharmaceutically acceptable salt, or enantiomer thereof, wherein $R^6$ is ethyl, isopropyl, tert-butyl or methylcyclopropyl.

18. A compound according to formula (I), item 1 or item 2, or a pharmaceutically acceptable salt, or enantiomer thereof, wherein $R^7$ is $C_{1-6}$alkoxy$C_{1-6}$alkyl, hydroxy$C_{1-6}$alkyl or amino$C_{1-6}$alkyl.

19. A compound according to formula (I), item 1 or item 2, or a pharmaceutically acceptable salt, or enantiomer thereof, wherein $R^7$ is methoxyethyl, methoxypropyl, hydroxydimethylpropyl, hydroxybutyl, hydroxypentyl, hydroxyhexyl, aminobutyl, aminopentyl or aminohexyl.

In context of the present invention the inhibitor of the invention may also be the compound according to formula (II), wherein the inhibitor is any one of the compounds as defined in items (1)-(20), below:

1. A compound according to formula (II), wherein
   $R^1$ is $C_{1-6}$alkyl, $C_{3-7}$cycloalkyl, hydroxy$C_{1-6}$alkyl, $C_{1-6}$alkoxycarbonyl$C_{1-6}$alkyl or carboxy$C_{1-6}$alkyl;
   $R^2$ is phenyl substituted by one, two, three or four groups independently selected from $C_{1-6}$alkyl, $C_{3-7}$cycloalkyl, halogen, halo$C_{1-6}$alkyl, cyano, nitro, hydroxy, halo$C_{1-6}$alkoxy, tetrahydrofuranyloxy, —O—$C_xH_{2x}$—$R^3$, —O—$C_yH_{2y}$—$NHR^6$, —$SO_2$—$R^{11}$, —$SO_2$—$NR^{12}R^{13}$, carboxy, $C_{1-6}$alkoxycarbonyl and —C(=O)—$NR^{12}R^{13}$; pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$; or pyrimidinyl substituted by $C_{1-6}$alkyl and di$C_{1-6}$alkylamino; wherein $R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, oxetanyl, tetrahydrofuranyl, tetrahydropyranyl, thietanyl, 1,1-dioxothietanyl, 1,1-dioxothiolanyl, morpholinyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$, —C(NHR$^7$)—C(=O)—$R^8$, carboxy$C_{1-6}$alkoxy or aminocarbonyl$C_{1-6}$alkoxy; wherein
   $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;
   $R^5$ is $C_{1-6}$alkyl, hydroxy or amino;
   $R^7$ is hydrogen or $C_{1-6}$alkoxycarbonyl;
   $R^8$ is hydroxy or $C_{1-6}$alkoxy;
   $R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
   $R^9$ and $R^{10}$ are independently selected from hydrogen, $C_{1-6}$alkyl and $C_{1-6}$alkylsulfonyl; or $R^9$ and $R^{10}$ together with the nitrogen to which they are attached form pyrrolidinyl, morpholinyl, piperidinyl, piperazinyl and oxopiperazinyl;
   $R^{11}$ is $C_{1-6}$alkyl or $C_{1-6}$alkoxy$C_{1-6}$alkyl;
   $R^{12}$ and $R^{13}$ are independently selected from hydrogen, $C_{1-6}$alkyl and $C_{1-6}$alkoxy$C_{1-6}$alkyl;
   x is 1, 2, 3, 4, 5, 6,7 or 8;
   y is 1, 2, 3, 4, 5, 6,7 or 8;
   U is CH;
   W is CH;
   Z is CH or N;
   X is N;
   Y is N;
   or a pharmaceutically acceptable salt, or an enantiomer, or a diastereomer thereof.

2. A compound according to formula (II) or item 1, wherein
   $R^1$ is $C_{1-6}$alkyl;
   $R^2$ is phenyl substituted by one, two, three or four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, —O—$C_xH_{2x}$—$R^3$, —O—$C_yH_{2y}$—$NHR^6$, —$SO_2$—$R^{11}$, —$SO_2$—$NR^{12}R^{13}$, carboxy, $C_{1-6}$alkoxycarbonyl and —C(=O)—$NR^{12}R^{13}$; pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$; or pyrimidinyl substituted by $C_{1-6}$alkyl and di$C_{1-6}$alkylamino; wherein $R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$, —C(NHR$^7$)—C(=O)—$R^8$, carboxy$C_{1-6}$alkoxy or aminocarbonyl$C_{1-6}$alkoxy; wherein
   $R^4$ is hydroxy, $C_{1-6}$alkoxy, amino, $C_{1-6}$alkylamino, tetrahydrofuranylamino, or morpholinyl;
   $R^5$ is $C_{1-6}$alkyl, hydroxy or amino;
   $R^7$ is hydrogen or $C_{1-6}$alkoxycarbonyl;
   $R^8$ is hydroxy or $C_{1-6}$alkoxy;
   $R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;
   $R^9$ and $R^{10}$ are independently selected from hydrogen, $C_{1-6}$alkyl and $C_{1-6}$alkylsulfonyl; or $R^9$ and $R^{10}$ together with the nitrogen to which they are attached form pyrrolidinyl, morpholinyl, piperazinyl and oxopiperazinyl;
   $R^{11}$ is $C_{1-6}$alkoxy$C_{1-6}$alkyl;
   $R^{12}$ and $R^{13}$ are independently selected from hydrogen, $C_{1-6}$alkyl and $C_{1-6}$alkoxy$C_{1-6}$alkyl;
   x is 1, 2, 3, 4, 5, 6,7 or 8;
   y is 1, 2, 3, 4, 5, 6,7 or 8;
   U is CH;
   W is CH;
   Z is N;
   X is N;
   Y is N;
   or a pharmaceutically acceptable salt, or an enantiomer, or a diastereomer thereof.

3. A compound according to formula (II), item 1 or item 2, or a pharmaceutically acceptable salt, or enantiomer, or diastereomer thereof, wherein $R^1$ is methyl.

4. A compound according to formula (II), item 1 or item 2, wherein
   $R^1$ is $C_{1-6}$alkyl;
   $R^2$ is phenyl substituted by one, two, three or four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, —O—$C_xH_{2x}$—$R^3$, —O—$C_yH_{2y}$—$NHR^6$, —$SO_2$—$R^{11}$, —$SO_2$—$NR^{12}R^{13}$, carboxy, $C_{1-6}$alkoxycarbonyl and —C(=O)—$NR^{12}R^{13}$;

R³ is hydrogen, C₃₋₇cycloalkyl, haloC₃₋₇cycloalkyl, hydroxyC₁₋₆alkylC₃₋₇cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, C₁₋₆alkoxycarbonyloxopiperazinyl, oxoimidazolidinyl, C₁₋₆alkylpiperazinyl, C₁₋₆alkylcarbonylpiperazinyl, C₁₋₆alkylsulfonylpiperazinyl, C₁₋₆alkoxycarbonylpiperazinyl, azetidinyl, C₁₋₆alkylcarbonylazetidinyl, C₁₋₆alkylsulfonylazetidinyl, C₁₋₆alkoxycarbonylazetidinyl, —C(=O)—R⁴, C₁₋₆alkylsulfinyl, —SO₂—R⁵ or —C(NHR⁷)—C(=O)—R⁸; wherein R⁴ is hydroxy, C₁₋₆alkoxy, amino, C₁₋₆alkylamino, tetrahydrofuranylamino, or morpholinyl;

R⁵ is C₁₋₆alkyl, hydroxy or amino;

R⁷ is hydrogen or C₁₋₆alkoxycarbonyl;

R⁸ is hydroxy or C₁₋₆alkoxy;

R⁶ is hydrogen, C₁₋₆alkylcarbonyl, haloC₁₋₆alkylcarbonyl, C₁₋₆alkoxycarbonyl, C₃₋₇cycloalkylsulfonyl or C₁₋₆alkoxyC₁₋₆alkylsulfonyl;

R¹¹ is C₁₋₆alkoxyC₁₋₆alkyl;

R¹² and R¹³ are independently selected from hydrogen, C₁₋₆alkyl and C₁₋₆alkoxyC₁₋₆alkyl;

x is 1, 2, 3, 4, 5 or 6;

y is 1, 2, 3, 4, 5, 6, 7 or 8;

U is CH;

W is CH;

Z is N;

X is N;

Y is N;

or a pharmaceutically acceptable salt, or an enantiomer, or a diastereomer thereof.

5. A compound according to formula (II), or any one of items 1 to 4, wherein

R¹ is methyl;

R² is phenyl substituted by one, two, three or four groups independently selected from methyl, cyclopropyl, fluoro, chloro, iodo, trifluoromethyl, cyano, hydroxy, methoxy, difluoroethoxy, difluoromethoxy, trifluoroethoxy, trifluoromethoxy, cyclopropylmethoxy, difluorocyclopropylmethoxy, hydroxymethylcyclopropylmethoxy, oxetanylethoxy, oxetanylmethoxy, tetrahydrofuranylethoxy, tetrahydrofuranylmethoxy, tetrahydropyranylmethoxy, thietanylmethoxy, (1,1-dioxothietanyl)methoxy, (1,1-dioxothiolanyl)methoxy, oxopyrrolidinylpropoxy, oxomorpholinylpropoxy, oxopiperazinylpropoxy, (tert-butoxycarbonyloxopiperazinyl)propoxy, oxoimidazolidinylpropoxy, methylpiperazinylpropoxy, acetylpiperazinylpropoxy, methylsulfonylpiperazinylpropoxy, (tert-butoxycarbonylpiperazinyl)propoxy, azetidinylethoxy, acetylazetidinylethoxy, methylsulfonylazetidinylethoxy, (tert-butoxycarbonylazetidinyl)ethoxy, (tert-butoxycarbonylazetidinyl)methoxy, carboxybutoxy, carboxyethoxy, carboxyhexyloxy, carboxymethoxy, carboxypropoxy, methoxycarbonylbutoxy, ethoxycarbonylhexyloxy, aminocarbonylbutoxy, aminocarbonylhexyloxy, aminocarbonylmethoxy, aminocarbonylpropoxy, methylaminocarbonylpropoxy, tetrahydrofuranylaminocarbonylmethoxy, morpholinylcarbonylmethoxy, methylsulfinylpropoxy, methylsulfonylpropoxy, sulfopropoxy, aminosulfonylpropoxy, amino-carboxy-propoxy, (tert-butoxycarbonylamino)-carboxy-propoxy, (tert-butoxycarbonylamino)-(methoxycarbonyl)-propoxy, aminopropoxy, aminopentoxy, aminohexyloxy, aminooctyloxy, methylcarbonylaminopropoxy, chloropropylcarbonylaminopropoxy, (tert-butoxycarbonylamino)hexyloxy, (tert-butoxycarbonylamino)octyloxy, (tert-butoxycarbonylamino)pentoxy, (tert-butoxycarbonylamino)propoxy, cyclopropylsulfonylaminopropoxy, methoxyethylsulfonylaminopropoxy, methoxypropylsulfonyl, methoxypropylaminosulfonyl, N-methoxypropyl-N-methyl-aminosulfonyl, carboxy, methoxycarbonyl, methoxypropylaminocarbonyl, N-methoxypropyl-N-methyl-aminocarbonyl and tetrahydrofuranyloxy;

U is CH;

W is CH;

Z is N;

X is N;

Y is N;

or a pharmaceutically acceptable salt, or an enantiomer, or a diastereomer thereof.

6. A compound according to formula (II) or any one of items 1 to 4, or a pharmaceutically acceptable salt, or enantiomer, or diastereomer thereof, wherein R² is phenyl substituted by one, two or three groups independently selected from halogen, C₁₋₆alkoxy, haloC₁₋₆alkoxy, C₃₋₇cycloalkylC₁₋₆alkoxy and haloC₃₋₇cycloalkylC₁₋₆alkoxy.

7. A compound according to formula (II), or any one of items 1 to 6, or a pharmaceutically acceptable salt, or enantiomer, or diastereomer thereof, wherein R² is phenyl substituted by one, two or three groups independently selected from fluoro, chloro, methoxy, difluoroethoxy, trifluoroethoxy, cyclopropylmethoxy and difluorocyclopropylmethoxy.

8. A compound according to formula (II), or any one of items 1, 2 and 4, wherein R¹ is C₁₋₆alkyl;

R² is phenyl substituted by two or three groups independently selected from halogen, cyano, haloC₁₋₆alkoxy, —O—C$_x$H$_{2x}$—R³ and —O—C$_y$H$_{2y}$—NHR⁶;

R³ is hydrogen, C₃₋₇cycloalkyl, haloC₃₋₇cycloalkyl, oxetanyl, tetrahydrofuranyl, tetrahydropyranyl, C₁₋₆alkylsulfonylazetidinyl, aminocarbonyl or C₁₋₆alkylsulfonyl;

R⁶ is hydrogen or C₁₋₆alkoxycarbonyl;

x is 1, 2, 3, 4, 5 or 6;

y is 1, 2, 3, 4, 5 or 6;

U is CH;

W is CH;

Z is N;

X is N;

Y is N;

or a pharmaceutically acceptable salt, or an enantiomer, or a diastereomer thereof.

9. A compound according to formula (II), or any one of items 1 to 5 and 8, wherein R¹ is methyl;

R² is phenyl substituted by two or three groups independently selected from fluoro, chloro, cyano, methoxy, difluoroethoxy, trifluoroethoxy, cyclopropylmethoxy, difluorocyclopropylmethoxy, methylsulfonylpropoxy, aminocarbonylmethoxy, oxetanylmethoxy, oxetanylethoxy, tetrahydrofuranylmethoxy, tetrahydropyranylmethoxy, methylsulfonylazetidinylethoxy, aminohexyloxy and (tert-butoxycarbonylamino)propoxy;

U is CH;

W is CH;

Z is N;

X is N;

Y is N;

or a pharmaceutically acceptable salt, or an enantiomer, or a diastereomer thereof.

10. A compound according to formula (II), or item 1 or item 2, wherein
$R^1$ is $C_{1-6}$alkyl;
$R^2$ is pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$;
$R^3$ is hydrogen, $C_{3-7}$cycloalkyl, thietanyl, tetrahydrofuranyl, tetrahydropyranyl, oxomorpholinyl, 1,1-dioxo-thietanyl, $C_{1-6}$alkylcarbonylazetidinyl, $C_{1-6}$alkylsulfonylazetidinyl, —C(=O)—$R^4$, carboxy$C_{1-6}$alkoxy or aminocarbonyl$C_{1-6}$ alkoxy; wherein
$R^4$ is hydroxy, $C_{1-6}$alkoxy or amino;
$R^9$ and $R^{10}$ are independently selected from hydrogen, $C_{1-6}$alkyl and $C_{1-6}$alkylsulfonyl; or
$R^9$ and $R^{10}$ together with the nitrogen to which they are attached form pyrrolidinyl, morpholinyl, piperazinyl and oxopiperazinyl;
x is 1, 2, 3, 4, 5, 6, 7 or 8;
U is CH;
W is CH;
Z is N;
X is N;
Y is N;
or a pharmaceutically acceptable salt, or an enantiomer, or a diastereomer thereof.

11. A compound according to formula (II), or any one of items 1 to 3 and 10, wherein
$R^1$ is methyl;
$R^2$ is pyridinyl substituted by one, two or three groups independently selected from fluoro, chloro, iodo, methoxy, methyl, difluoroethoxy, tetrahydropyranyloxy, cyclopropylmethoxy, thietanylmethoxy, tetrahydrofuranylmethoxy, tetrahydropyranylmethoxy, oxomorpholinylpropoxy, (1,1-dioxo-thietanyl)methoxy, acetylazetidinylmethoxy, methylsulfonylazetidinylmethoxy, carboxybutoxy, carboxyheptyloxy, carboxyhexyloxy, carboxypentyloxy, carboxypropoxy, methoxycarbonylheptyloxy, aminocarbonylbutoxy, aminocarbonylheptyloxy, aminocarbonylhexyloxy, aminocarbonylmethoxy, aminocarbonylpentyloxy, aminocarbonylpropoxy, carboxymethoxypropoxy, aminocarbonylmethoxypropoxy, amino, methylamino, dimethylamino, methylsulfonylamino, pyrrolidinyl, morpholinyl, piperazinyl and oxopiperazinyl;
U is CH;
W is CH;
Z is N;
X is N;
Y is N;
or a pharmaceutically acceptable salt, or an enantiomer, or a diastereomer thereof.

12. A compound according to formula (II), or any one of items 1 to 3 and 10, or a pharmaceutically acceptable salt, or enantiomer, or diastereomer thereof, wherein $R^2$ is pyridinyl substituted by one, two or three groups independently selected from halogen, $C_{1-6}$alkoxy, halo$C_{1-6}$alkoxy, $C_{1-6}$alkylamino, di$C_{1-6}$alkylamino, pyrrolidinyl and oxopiperazinyl.

13. A compound according to formula (II), or any one of items 1 to 3, 10 and 11, or a pharmaceutically acceptable salt, or enantiomer, or diastereomer thereof, wherein $R^2$ is pyridinyl substituted by one, two or three groups independently selected from fluoro, chloro, methoxy, difluoroethoxy, methylamino, dimethylamino, pyrrolidinyl and oxopiperazinyl.

14. A compound according to formula (II), or any one of items 1, 2 and 10, wherein
$R^1$ is $C_{1-6}$alkyl;
$R^2$ is pyridinyl substituted by two or three groups independently selected from halogen, halo$C_{1-6}$alkoxy, —O—$C_xH_{2x}$—$R^3$ and $NR^9R^{10}$;
$R^3$ is hydrogen, tetrahydrofuranyl, tetrahydropyranyl, oxomorpholinyl or aminocarbonyl;
$R^9$ and $R^{10}$ are independently selected from hydrogen and $C_{1-6}$alkyl; or
$R^9$ and $R^{10}$ together with the nitrogen to which they are attached form pyrrolidinyl and oxopiperazinyl;
x is 1, 2, 3, 4, 5 or 6;
U is CH;
W is CH;
Z is N;
X is N;
Y is N;
or a pharmaceutically acceptable salt, or an enantiomer, or a diastereomer thereof.

15. A compound according to formula (II), or item 1, or item 6, wherein
$R^1$ is methyl;
$R^2$ is pyridinyl substituted by two or three groups independently selected from fluoro, chloro, methoxy, difluoroethoxy, tetrahydrofuranylmethoxy, tetrahydropyranylmethoxy, oxomorpholinylpropoxy, aminocarbonylhexyloxy, methylamino, dimethylamino, pyrrolidinyl and oxopiperazinyl;
U is CH;
W is CH;
Z is N;
X is N;
Y is N;
or a pharmaceutically acceptable salt, or an enantiomer, or a diastereomer thereof.

16. A compound according to formula (II), or item 1, wherein
$R^1$ is $C_{1-6}$alkyl, $C_{3-7}$cycloalkyl, hydroxy$C_{1-6}$alkyl, $C_{1-6}$alkoxycarbonyl$C_{1-6}$alkyl, or carboxy$C_{1-6}$alkyl;
$R^2$ is phenyl substituted by one, two or three groups independently selected from halogen, nitro, $C_{1-6}$alkylsulfonyl, —O—$C_xH_{2x}$—$R^3$ and —O—$C_yH_{2y}$—$NHR^6$; or pyridinyl substituted by two groups independently selected from halogen, halo$C_{1-6}$alkoxy, —O—$C_xH_{2x}$—$R^3$ and $NR^9R^{10}$; wherein
$R^3$ is hydrogen, $C_{3-7}$cycloalkyl, hydroxy, $C_{1-6}$alkoxy, tetrahydrofuranyl, tetrahydropyranyl, morpholinyl, —C(=O)—$R^4$, —$SO_2$—$R^5$ or aminocarbonyl$C_{1-6}$alkoxy; wherein
$R^4$ is hydroxy, $C_{1-6}$alkoxy, amino, di$C_{1-6}$alkylamino or pyrrolidinyl;
$R^5$ is $C_{1-6}$alkyl;
$R^6$ is hydrogen or $C_{1-6}$alkylsulfonyl;
$R^9$ and $R^{10}$ are $C_{1-6}$alkyl; or
$R^9$ and $R^{10}$ together with the nitrogen to which they are attached form pyrrolidinyl, morpholinyl, piperidinyl and oxopiperazinyl;
x is 1, 2, 3, 4, 5 or 6;
y is 1, 2, 3, 4, 5 or 6;
U is CH;
W is CH;
Z is CH;
X is N;
Y is N;
or a pharmaceutically acceptable salt, or an enantiomer, or a diastereomer thereof.

17. A compound according to formula (II), or item 1, or item 16, or a pharmaceutically acceptable salt, or enantiomer, or diastereomer thereof, wherein $R^1$ is $C_{1-6}$alkyl.

18. A compound according to formula (II), or any one of items 1, 16 and 17, or a pharmaceutically acceptable salt, or enantiomer, or diastereomer thereof, wherein $R^1$ is methyl.

19. A compound according to formula (II), or any one of items 1 and 16 to 18, or a pharmaceutically acceptable salt, or enantiomer, or diastereomer thereof, wherein $R^2$ is phenyl substituted by one, two or three groups independently selected from halogen and $C_{1-6}$alkoxy; or pyridinyl substituted by two groups independently selected from halogen, $diC_{1-6}$alkylamino, pyrrolidinyl, and oxopiperazinyl.

20. A compound according to formula (II), or any one of items 1, and 16 to 19, or a pharmaceutically acceptable salt, or enantiomer, or diastereomer thereof, wherein $R^2$ is phenyl substituted by one, two or three groups independently selected from fluoro and methoxy; or pyridinyl substituted by two groups independently selected from fluoro, dimethylamino, pyrrolidinyl and oxopiperazinyl.

As described above, the inhibitor of the present invention may also be a RNAi molecule against PAPD5 and/or PAPD7. Said RNAi molecule may be a siRNA or a shRNA.

For example, the inhibitor of the present invention may be a siRNA that is directed against PAPD5, wherein said siRNA is any one of the following siRNAs:

```
PAPD5 siRNA pool (L-010011-00-0010;
ON-TARGETplus Human PAPD5):
siRNA-1-J-010011-05-Target Sequence:
                              (SEQ ID NO: 10)
CAUCAAUGCUUUAUAUCGA siRNA-2-J-010011-06-Target Sequence:
                              (SEQ ID NO: 11)
GGACGACACUUCAAUUAUU siRNA-3-J-010011-07-Target Sequence:
                              (SEQ ID NO: 12)
GAUAAAGGAUGGUGGUUCA siRNA-4-J-010011-08-Target Sequence:
                              (SEQ ID NO: 13)
GAAUAGACCUGAGCCUUCA
```

The inhibitor of the present invention may also be a siRNA that is directed against PAPD7, wherein said siRNA is any one of the following siRNAs:

```
PAPD7 siRNA pool (L-009807-00-0005;
ON-TARGETplus Human PAPD7):
siRNA-1-J-009807-05-Target Sequence:
                              (SEQ ID NO: 14)
GGAGUGACGUUGAUUCAGA siRNA-2-J-009807-06-Target Sequence:
                              (SEQ ID NO: 15)
CGGAGUUCAUCAAGAAUUA siRNA-3-J-009807-07-Target Sequence:
                              (SEQ ID NO: 16)
CGGAGUUCAUCAAGAAUUA siRNA-4-J-009807-08-Target Sequence:
                              (SEQ ID NO: 17)
GCGAAUAGCCACAUGCAAU
```

Above, target sequences of suitable siRNAs are shown. The sequences of the corresponding siRNAs are directly complementary to these target sequences.

It is envisaged in context of the present invention that (a) siRNA(s) directed against PAPD5 is combined with (a) siRNA(s) directed against PAPD7, in order to inhibit expression of both, PAPD5 and PAPD7.

The appended examples surprisingly demonstrate that two anti-HBV agents that are completely different in structure (i.e. DHQ and THP) have a shared binding site for PAPD5 and PAPD7 or at least are binding in close proximity to each other. In particular, selected interaction domains (SIDs) within PAPD5 and PAPD7 have been identified. SIDs are the amino acid sequences that are shared by all prey fragments matching the same reference protein. Therefore, the SIDs correspond to the amino acid regions where the anti-HBV agents DHQ and THP bind to PAPD5 and PAPD7. Accordingly, binding to these regions leads to an inhibition of the activity of PAPD5 and PAPD7, which results in inhibition of propagation of HBV. Thus, the inhibitor of the invention may be an antibody that specifically binds to at least one SID of PAPD5 and/or of PAPD7. Accordingly, the inhibitor of the invention may be an antibody that specifically binds to the amino acid stretch of any one of SEQ ID NOs: 7-9. The inhibitor of the invention may also be an antibody that specifically binds to more than one of the amino acid stretches of SEQ ID NOs: 7-9.

Applications

In context of the present invention it has surprisingly been shown that the combined inhibition of PAPD5 and PAPD7 leads to a synergistic effect in the inhibition of HBV propagation. The appended examples show that reduction of the expression of PAPD5 alone leads to a reduction of the secretion of HBsAg and HBeAg of around 50%. Reduction of the expression of PAPD7 alone leads to a reduction of the secretion of HBsAg and HBeAg of not more than 15%. Simultaneous knock-down of PAPD5 and PAPD7 leads to a synergistic effect in the reduction of secretion of HBsAg and HBeAg that lies above the sum of the single knock-downs. Without being bound by theory, this synergistic effect may be due to a compensatory effect of PAPD5 and PAPD7 since both proteins have high sequence homology and same enzymatic functions. Therefore, one embodiment of the present invention relates to a combined preparation comprising an inhibitor of PAPD5 and an inhibitor of PAPD7 for use in the treatment and/or prevention of a HBV infection. Thus, the present invention relates to a combined preparation comprising an inhibitor of PAPD5 and an inhibitor of PAPD7 for simultaneous or sequential use in the treatment and/or prevention of a HBV infection. It is envisaged in context of the invention that said combined preparation is used for treating (e.g. ameliorating) a HBV infection. The definitions disclosed herein in connection with the inhibitor of the present invention apply, mutatis mutandis, to the combined preparation of the present invention. The combined preparation may comprise a molecule that is a PAPD5 inhibitor and a separate molecule that is a PAPD7 inhibitor (e.g. two separate siRNA molecules or two separate small molecules). These two separate inhibitors may be formulated within one unit, e.g., within one pill or vial. Alternatively, these two separate inhibitors may be formulated separately, in separate units, e.g. separate pills or vials. The two separate inhibitors may be administered together, (i.e. simultaneously) or separately (i.e. sequentially) provided that the synergistic effect of the two inhibitors is achieved. In one aspect of the invention the combined preparation leads to a reduction of secretion of HBsAg and HBeAg of at least 50% as compared to the no drug control (i.e. compared to cells or subjects to which no drug is administrated).

The present invention also relates to a pharmaceutical composition for use in the treatment and/or prevention of a HBV infection, wherein the pharmaceutical composition comprises
(i) the inhibitor of the invention; or the combined preparation of the invention; and
(ii) optionally a pharmaceutically acceptable carrier.

Accordingly, the present invention relates to a method of treating and/or preventing a HBV infection, wherein the method comprises administering an effective amount of the inhibitor of the invention, the pharmaceutical composition of the invention, or of the combined preparation of the invention to a subject in need of such a treatment.

The inhibitor of the invention, the combined preparation of the invention, or the pharmaceutical composition of the invention may be used in a combination therapy. For example, the inhibitor of the invention, the combined preparation of the invention, or the pharmaceutical composition of the invention may be combined with other anti-HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti-HBV agents such as a HBV RNA replication inhibitor, a HBsAg secretion inhibitor, a HBV capsid inhibitor, an antisense oligomer (e.g. as described in WO2012/145697 and WO 2014/179629), a siRNA (e.g. described in WO 2005/014806, WO 2012/024170, WO 2012/2055362, WO 2013/003520, WO 2013/159109, WO 2017/027350 and WO2017/015175), a HBV therapeutic vaccine, a HBV prophylactic vaccine, a HBV antibody therapy (monoclonal or polyclonal), or TLR 2, 3, 7, 8 or 9 agonists for the treatment and/or prophylaxis of HBV.

The appended examples demonstrate that down regulation of PAPD5 and/or PAPD7 goes along with a reduction in the production of HBsAg and HBeAg as well as of intracellular HBV mRNA in HBV infected cells. These results indicate that the amount and/or activity of PAPD5 and/or PAPD7 can be used for monitoring therapeutic success during the treatment of a HBV infection, e.g. if treatment with an inhibitor of PAPD5 and/or PAPD7 is ongoing or has been performed. Thus, the present invention relates to a method for monitoring the therapeutic success during the treatment of a HBV infection, wherein the method comprises:
(a) analyzing in a sample obtained from a test subject the amount and/or activity of PAPD5 and/or PAPD7;
(b) comparing said amount and/or activity with reference data corresponding to the amount and/or activity of PAPD5 and/or PAPD7 of at least one reference subject; and
(c) predicting therapeutic success based on the comparison step (b).

In the monitoring method of the invention the test subject may be a human being who receives medication for a HBV infection or has received medication for a HBV infection. The medication may comprise anti-HBV agents as described above. The medication may also comprise an inhibitor of PAPD5 and/or PAPD.

In the monitoring method of the invention the reference data may correspond to the amount and/or activity of PAPD5 and/or PAPD7 in a sample of at least one reference subject. Said sample may be blood or a liver biopsy.

One aspect of the invention relates to the monitoring method of the invention, wherein the at least one reference subject has a HBV infection but did not receive medication for a HBV infection; and wherein in step (c) a decreased amount and/or activity of PAPD5 and/or PAPD7 of the test subject as compared to the reference data indicates therapeutic success in the treatment of a HBV infection. For example, said decreased amount and/or activity of PAPD5 and/or PAPD7 may mean that the amount and/or activity of PAPD5 and/or PAPD7 in the sample of the test subject is 0 to 90% of the amount and/or activity of PAPD5 and/or PAPD7 in the sample of the at least one reference subject. For example, said decreased amount and/or activity of PAPD5 and/or PAPD7 may be 0 to 80%, preferably 0 to 70%, more preferably 0 to 60%, even more preferably 0 to 50%, even more preferably 0 to 40%, even more preferably 0 to 30, even more preferably 0 to 20%, and most preferably 0 to 10% of the amount and/or activity of PAPD5 and/or PAPD7 in the sample of the at least one reference subject.

Another aspect of the invention relates to the monitoring method of the invention, wherein the at least one reference subject has a HBV infection and has received medication for a HBV infection; and wherein in step (c) an identical or similar amount and/or activity of PAPD5 and/or PAPD7 of the test subject as compared to the reference data indicates therapeutic success in the treatment of a HBV infection. A further aspect of the invention relates to the monitoring method of the invention, wherein the at least one reference subject does not have a HBV infection; and wherein in step (c) an identical or similar amount and/or activity of PAPD5 and/or PAPD7 of the test subject as compared to the reference data indicates therapeutic success in the treatment of a HBV infection. An identical or similar amount and/or activity of PAPD5 and/or PAPD7 may mean that the amount and/or activity of PAPD5 and/or PAPD7 in the sample of the test subject is 90-110% of the amount and/or activity of PAPD5 and/or PAPD7 in the sample of the at least one reference subject. For example, said identical or similar amount and/or activity of PAPD5 and/or PAPD7 may be 95-105% of the amount and/or activity of PAPD5 and/or PAPD7 in the sample of the at least one reference subject.

Also encompassed by the present invention is a cell or a non-human animal (e.g. a mouse, rat, ferret or rabbit) with increased, reduced or absent PAPD5 and/or PAPD7 expression that can be used for identifying and/or characterizing a compound that prevents and/or treats (e.g. ameliorates) a HBV infection. For example, said cell or non-human animal may comprise an exogenous nucleotide sequence encoding PAPD5 and/or PAPD7, e.g. cloned into an expression vector and operable linked to an exogenous promoter. Said cell or non-human animal may overexpress PAPD5 and/or PAPD7, preferably PAPD5 and PAPD7. Alternatively, said cell or non-human animal may have a knock-down of PAPD5 and/or PAPD7, preferably of PAPD5 and PAPD7.

Embodiments of the Invention

Thus, the present invention relates to the following items:
1. A method for identifying a compound that prevents, ameliorates and/or inhibits a hepatitis B virus (HBV) infection, comprising:
(a) contacting a test compound with
(a1) PAP associated domain containing 5 (PAPD5) and/or PAP associated domain containing 7 (PAPD7); or
(a2) a cell expressing PAPD5 and/or PAPD7;
(b) measuring the expression and/or activity of PAPD5 and/or PAPD7 in the presence and absence of said test compound; and (c) identifying a compound that reduces the expression and/or activity of PAPD5 and/or PAPD7 as a compound that prevents, ameliorates and/or inhibits a HBV infection.

2. A method for identifying a compound that prevents, ameliorates and/or inhibits a HBV infection, comprising:
(a) contacting a test compound with
(a1) PAPD5 and/or PAPD7; or
(a2) a cell expressing PAPD5 and/or PAPD7;
(b) measuring whether the test compound binds to PAPD5 and/or to PAPD7;
(c) measuring whether the test compound inhibits propagation of HBV; and
(d) identifying a compound that binds to PAPD5 and/or PAPD7 and inhibits propagation of HBV as a compound that prevents, ameliorates and/or inhibits a HBV infection.

3. The method of item 1 or 2, wherein PAPD5 is the PAPD5 polypeptide or the PAPD5 mRNA.

4. The method of item 3, wherein the PAPD5 polypeptide is a polypeptide comprising or consisting of
(i) the amino acid sequence of SEQ ID NO: 1 or 2;
(ii) an amino acid sequence having at least 80% identity to an amino acid sequence of (i), wherein the polypeptide has poly-A polymerase function;
(iii) the amino acid sequence of an enzymatically active fragment of SEQ ID NO: 1 or 2; or
(iv) an amino acid sequence having at least 80% identity to an amino acid sequence of (iii), wherein the polypeptide has poly-A polymerase function.

5. The method of item 3, wherein the PAPD5 mRNA is a polynucleotide comprising or consisting of
(i) the nucleotide sequence encoding the amino acid sequence of SEQ ID NO: 1 or 2;
(ii) a nucleotide sequence encoding an amino acid sequence having at least 80% identity to SEQ ID NO: 1 or 2, wherein the polynucleotide encodes a polypeptide that has poly-A polymerase function;
(iii) the nucleotide sequence encoding an enzymatically active fragment of SEQ ID NO: 1 or 2; or
(iv) a nucleotide sequence encoding an amino acid sequence having at least 80% identity to an amino acid sequence of an enzymatically active fragment of SEQ ID NO: 1 or 2, wherein the polynucleotide encodes a polypeptide that has poly-A polymerase function.

6. The method of item 1 or 2, wherein PAPD7 is the PAPD7 polypeptide or the PAPD7 mRNA.

7. The method of item 6, wherein the PAPD7 polypeptide is a polypeptide comprising or consisting of
(i) the amino acid sequence of SEQ ID NO: 3;
(ii) an amino acid sequence having at least 80% identity to an amino acid sequence of (i), wherein the polypeptide has poly-A polymerase function;
(iii) the amino acid sequence of an enzymatically active fragment of SEQ ID NO: 3; or
(iv) an amino acid sequence having at least 80% identity to an amino acid sequence of (iii), wherein the polypeptide has poly-A polymerase function.

8. The method of item 6, wherein the PAPD7 mRNA is a polynucleotide comprising or consisting of
(i) the nucleotide sequence encoding the amino acid sequence of SEQ ID NO: 3;
(ii) a nucleotide sequence encoding an amino acid sequence having at least 80% identity to SEQ ID NO: 3, wherein the polynucleotide encodes a polypeptide that has poly-A polymerase function;
(iii) the nucleotide sequence encoding an enzymatically active fragment of SEQ ID NO: 3; or
(iv) a nucleotide sequence encoding an amino acid sequence having at least 80% identity to an amino acid sequence of an enzymatically active fragment of SEQ ID NO: 3, wherein the polynucleotide encodes a polypeptide that has poly-A polymerase function.

9. The method of any one of items 1 to 8, wherein said cell is a eukaryotic cell.

10. The method of any one of items 2 to 9, wherein the compound that inhibits propagation of HBV inhibits secretion of HBV surface antigen (HBsAg), inhibits secretion of HBV envelope antigen (HBeAg), and/or inhibits production of intracellular HBV mRNA or HBV DNA.

11. The method of any one of items 1 to 10, which additionally comprises the step of comparing the test compound to a control.

12. The method of item 11, wherein in said control an inactive test compound is used, wherein said inactive test compound is a compound that:
(i) does not reduce the expression and/or activity of PAPD5 and/or PAPD7; and/or
(ii) does not bind to PAPD5 and/or PAPD7 and does not inhibit propagation of HBV.

13. The method of any one of items 1 to 12, wherein said test compound is
(i) a small molecule of a screening library; or
(ii) a peptide of a phage display library, of an antibody fragment library, or derived from a cDNA library.

14. The method of any one of items 1 and 3 to 13, wherein the activity of PAPD5 and PAPD7 is the poly-A polymerase function.

15. An inhibitor of PAPD5 and/or PAPD7 for use in treating and/or preventing a HBV infection, wherein said inhibitor is
(i) a small molecule that binds to PAPD5 and/or PAPD7;
(ii) a RNA interference (RNAi) molecule against PAPD5 and/or PAPD7;
(iii) an antibody that specifically binds to PAPD5 and/or PAPD7; or
(iv) a genome editing machinery, comprising:
(a) a site-specific DNA nuclease or a polynucleotide encoding a site-specific DNA nuclease; and
(b) a guide RNA or a polynucleotide encoding a guide RNA.

16. The inhibitor for the use according to item 15, which
(i) binds to PAPD5 and/or PAPD7; and/or
(ii) inhibits expression and/or activity of PAPD5 and/or PAPD7.

17. The inhibitor for the use according to item 15 or 16, wherein the inhibitor reduces secretion of HBsAg and HBeAg.

18. The inhibitor for the use according to any one of items 15 to 17, wherein the inhibitor inhibits development of chronic HBV infection and/or reduces the infectiousness of a HBV infected person.

19. The inhibitor for the use according to any one of items 15 to 18, wherein the inhibitor is the compound of formula (III) or (IV):

formula (III)

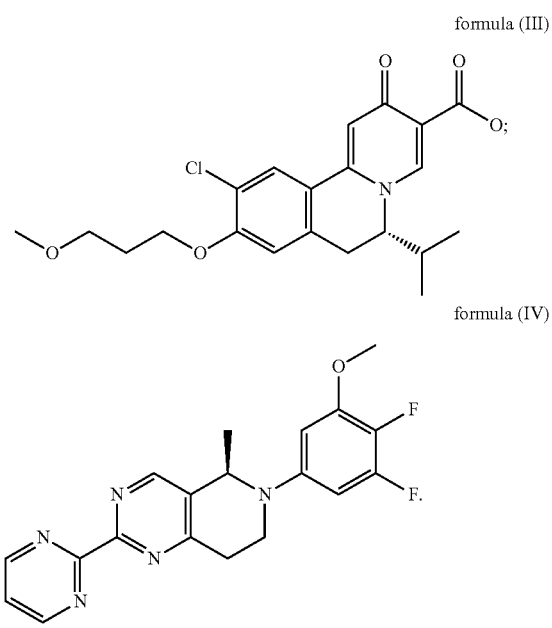

formula (IV)

20. The inhibitor for the use according to any one of items 15 to 18, wherein the inhibitor is an RNAi molecule such as a siRNA or a shRNA.

21. The inhibitor for the use according to any one of items 15 to 18, wherein the inhibitor is an antibody that specifically binds to the amino acid stretch of any one of SEQ ID NOs: 7-9.

22. Combined preparation comprising an inhibitor of PAPD5 and an inhibitor of PAPD7 for simultaneous or sequential use in the treatment and/or prevention of a HBV infection.

23. A pharmaceutical composition for use in the treatment and/or prevention of a HBV infection, wherein the pharmaceutical composition comprises
(i) the inhibitor for the use according to any one of items 15 to 21; or the combined preparation of item 22; and
(ii) optionally a pharmaceutically acceptable carrier.

24. A method for monitoring the therapeutic success during the treatment of a HBV infection, wherein the method comprises:
(a) analyzing in a sample obtained from a test subject the amount and/or activity of PAPD5 and/or PAPD7;
(b) comparing said amount and/or activity with reference data corresponding to the amount and/or activity of PAPD5 and/or PAPD7 of at least one reference subject; and
(c) predicting therapeutic success based on the comparison step (b).

25. The monitoring method of item 24, wherein the test subject is a human being who receives medication for a HBV infection or has received medication for a HBV infection.

26. The monitoring method of item 24 or 25, wherein the reference data corresponds to the amount and/or activity of PAPD5 and/or PAPD7 in a sample of at least one reference subject.

27. The monitoring method of any one of items 24 to 26, wherein the at least one reference subject has a HBV infection but did not receive medication for a HBV infection; and wherein in step (c) a decreased amount and/or activity of PAPD5 and/or PAPD7 of the test subject as compared to the reference data indicates therapeutic success in the treatment of a HBV infection.

28. The monitoring method of item 27, wherein said decreased amount and/or activity of PAPD5 and/or PAPD7 means that the amount and/or activity of PAPD5 and/or PAPD7 in the sample of the test subject is 0 to 90% of the amount and/or activity of PAPD5 and/or PAPD7 in the sample of the at least one reference subject.

29. The monitoring method of any one of items 24 to 26, wherein the at least one reference subject has a HBV infection and has received medication for a HBV infection; and wherein in step (c) an identical or similar amount and/or activity of PAPD5 and/or PAPD7 of the test subject as compared to the reference data indicates therapeutic success in the treatment of a HBV infection.

30. The monitoring method of any one of items 24 to 26, wherein the at least one reference subject does not have a HBV infection; and wherein in step (c) an identical or similar amount and/or activity of PAPD5 and/or PAPD7 of the test subject as compared to the reference data indicates therapeutic success in the treatment of a HBV infection.

31. The monitoring method of item 29 or 30, wherein said identical or similar amount and/or activity of PAPD5 and/or PAPD7 means that the amount and/or activity of PAPD5 and/or PAPD7 in the sample of the test subject is 90-110% of the amount and/or activity of PAPD5 and/or PAPD7 in the sample of the at least one reference subject.

Manufacture

A compound of formula (I) (i.e. a dihydroquinolizinone compound according to formula (I)) may be synthesized as described in WO 2015/113990 A1. In brief, a compound of formula (I) may be prepared by a method comprising the following steps:
(a) hydrolysis of a compound of formula (A)

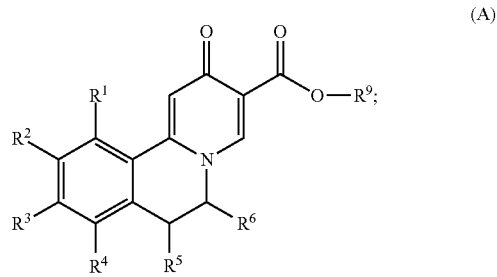

or
(b) hydrolysis of a compound of formula (B)

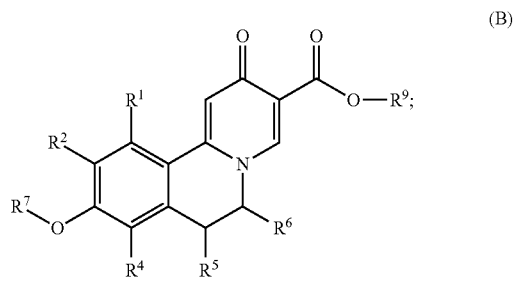

wherein $R^1$ to $R^7$ and $R^9$ are defined above with respect to formula (I) unless otherwise indicated.

In step (a) and step (b) a base such as lithium hydroxide or sodium hydroxide can for example be used.

A compound of formula (II) (i.e. a tetrahydropyridopyrimidine compound according to formula (II)) may be synthesized as described in WO2016/177655. In brief, a compound of formula (II) may be prepared by a method comprising one of the following steps:

(a) coupling of a compound of formula (A)

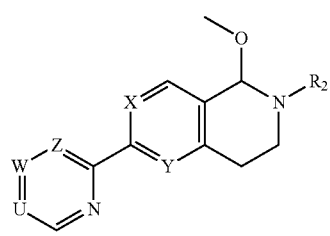

(A)

with a compound of formula (B)
$R^1M$ (B)
in the presence of a Lewis acid;
(b) coupling of a compound of formula (C)

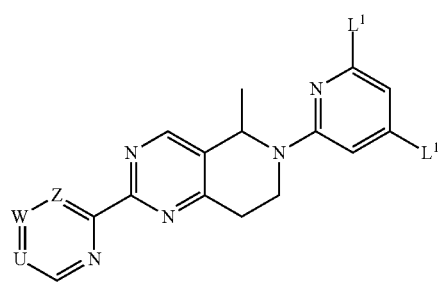

(C)

with a compound of formula (D)
$NHR^9R^{10}$ (D)
in the presence of a base;
(c) coupling of a compound of formula (E)

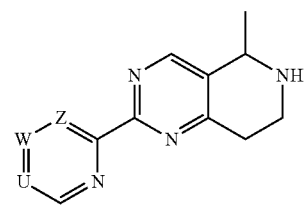

(E)

with a compound of formula (F)
$R^2$-$L^2$ (F);
wherein $R^1$, $R^2$, U, W, X, Y and Z are defined as above with respect to formula (II); M is H, Mg, Zn or Na; $L^1$ is F, Cl or Br; and $L^2$ is F, Cl or Br.

In step (a), the Lewis acid can for example be $BF_3 \cdot Et_2O$ or $Sc(OTf)_3$;

In step (b), the base can for example be $K_2CO_3$ or DIEA;

In step (c), the reaction can be carried out in the presence of a base, and the base can for example be $K_2CO_3$ or DIEA. The reaction can also be carried out in the absence of a base.

Compositions

As described above, the invention relates to an inhibitor of PAPD5 and/or PAPD7 for use in treating and/or preventing a HBV infection; a combined preparation comprising an inhibitor of PAPD5 and an inhibitor of PAPD7 for use in the treatment and/or prevention of a HBV infection; and a pharmaceutical composition comprising said inhibitor or said combined preparation. Said pharmaceutical composition (i.e. medicament) optionally comprises a pharmaceutically acceptable carrier. Said pharmaceutical composition may further comprise a therapeutically acceptable diluent or excipient.

A typical pharmaceutical composition is prepared by mixing a PAPD5 inhibitor and/or a PAPD7 inhibitor and a carrier or excipient. Suitable carriers and excipients are well known to those skilled in the art and are described in detail in, e.g., Ansel, Ansel's Pharmaceutical Dosage Forms and Drug Delivery Systems, Philadelphia: Lippincott, Williams & Wilkins, 2004; Gennaro, Remington: The Science and Practice of Pharmacy, Philadelphia: Lippincott, Williams & Wilkins, 2000; and Rowe, Handbook of Pharmaceutical Excipients, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to improve appearance of the drug or aid in the manufacturing of the pharmaceutical product (i.e., medicament). For example, the pharmaceutical composition of the invention may be formulated by mixing an inhibitor of PAPD5 and/or an inhibitor of PAPD7 at ambient temperature at an appropriate pH, and with the desired degree of purity, with physiologically acceptable carriers, i.e., carriers that are non-toxic to recipients at the dosages and concentrations employed into a suitable administration form. The pharmaceutical composition of the invention may be sterile.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

Compounds contain one or several chiral centers can either be present as racemates, diastereomeric mixtures, or optically active single isomers. The racemates can be separated according to known methods into the enantiomers.

Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of the inhibitor of the invention, the combined preparation of the invention, or the pharmaceutical composition of the invention will be governed by such considerations, and is the minimum amount necessary to inhibit HBsAg and/or HBeAg. For example, such amount may be below the amount that is toxic to the cells of the recipient, or to the mammal as a whole.

For example, if the PAPD5 inhibitor and/or the PAPD7 inhibitor is/are (a) compound(s) according to formula (I) or (II), then the pharmaceutically effective amount administered parenterally per dose may be in the range of about 0.01 to 100 mg/kg, alternatively about 0.01 to 100 mg/kg of patient body weight per day, with the typical initial range of compound used being 0.3 to 15 mg/kg/day. In another example, if the PAPD5 inhibitor and/or the PAPD7 inhibitor is/are (a) compound(s) according to formula (I) or (II), oral unit dosage forms, such as tablets and capsules, preferably contain from about 0.1 to about 1000 mg.

The inhibitor of the invention, the combined preparation of the invention, or the pharmaceutical composition of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The inhibitor of the invention, the combined preparation of the invention, or the pharmaceutical composition of the invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The inhibitor of the invention, the combined preparation of the invention, or the pharmaceutical composition of the invention are useful in the prevention and/or treatment of an HBV invention. They preferably inhibit secretion of HBsAg and/or HBeAg, most preferably of HBsAg and HBeAg.

Definitions

The terms "treatment", "treating", "treats" or the like are used herein to generally mean obtaining a desired pharmacological and/or physiological effect. This effect is therapeutic in terms of partially or completely curing a disease and/or adverse effect attributed to the disease. The term "treatment" as used herein covers any treatment of a disease in a subject and includes: (a) inhibiting the disease, i.e. arresting its development like the inhibition of increase of HBsAg and/or HBeAg; or (b) ameliorating (i.e. relieving) the disease, i.e. causing regression of the disease, like the repression of HBsAg and/or HBeAg production. Thus, a compound that ameliorates and/or inhibits a HBV infection is a compound that treats a HBV invention. Preferably, the term "treatment" as used herein relates to medical intervention of an already manifested disorder, like the treatment of an already defined and manifested HBV infection. Herein the term "preventing", "prevention" or "prevents" relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein "preventing a HBV infection" includes preventing a HBV infection from occurring in a subject, and preventing the occurrence of symptoms of a HBV infection.

For the purposes of the present invention the "subject" (or "patient") may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, guinea pig, ferret, cat, dog, chicken, sheep, bovine species, horse, camel, or primate. Preferably, the subject is a mammal. More preferably the subject is human.

The term "hepatitis B virus infection" or "HBV infection" is commonly known in the art and refers to an infectious disease that is caused by the hepatitis B virus (HBV) and affects the liver. A HBV infection can be an acute or a chronic infection. Some infected persons have no symptoms during the initial infection and some develop a rapid onset of sickness with vomiting, yellowish skin, tiredness, dark urine and abdominal pain ("Hepatitis B Fact sheet N°204". who.int. July 2014. Retrieved 4 Nov. 2014). Often these symptoms last a few weeks and can result in death. It may take 30 to 180 days for symptoms to begin. In those who get infected around the time of birth 90% develop a chronic hepatitis B infection while less than 10% of those infected after the age of five do ("Hepatitis B FAQs for the Public-Transmission", U.S. Centers for Disease Control and Prevention (CDC), retrieved 2011-11-29). Most of those with chronic disease have no symptoms; however, cirrhosis and liver cancer may eventually develop (Chang, 2007, Semin Fetal Neonatal Med, 12: 160-167). These complications result in the death of 15 to 25% of those with chronic disease ("Hepatitis B Fact sheet N°204". who.int. July 2014, retrieved 4 Nov. 2014). Herein, the term "HBV infection" includes the acute and chronic hepatitis B infection. The term "HBV infection" also includes the asymptotic stage of the initial infection, the symptomatic stages, as well as the asymptotic chronic stage of the HBV infection.

Herein, an enzymatically active fragment of SEQ ID NO: 1 or 2 (i.e. of PAPD5) relates to those polypeptides that comprise a stretch of contiguous amino acid residues of SEQ ID NO: 1 or 2 (i.e. of PAPD5) and that retain a biological activity (i.e. functionality) of PAPD5, particularly the poly-A polymerase function. In line with this, herein, an enzymatically active fragment of SEQ ID NO: 3 (i.e. of PAPD7) relates to those polypeptides that comprise a stretch of contiguous amino acid residues of SEQ ID NO: 3 (i.e. of PAPD7) and that retain a biological activity (i.e. functionality) of PAPD7, particularly the poly-A polymerase function. Examples for enzymatically active fragments of PAPD5 and PAPD7 are the nucleotidyltransferase domain and the Cid1 poly A polymerase.

Herein, term "polypeptide" includes all molecules that comprise or consist of amino acid monomers linked by peptide (amide) bonds. Thus, the term "polypeptide" comprises all amino acid sequences, such as peptides, oliogopeptides, polypeptides and proteins. The "polypeptide" described herein may be a naturally occurring polypeptide or a non-naturally occurring polypeptide. The non-naturally occurring polypeptide may comprise at least one mutation (e.g. amino acid substitution, amino acid deletion or amino acid addition) as compared to the naturally occurring counterpart. The non-naturally occurring polypeptide may also be cloned in a vector and/or be operable linked to a promoter that is not the natural promoter of said polypeptide. Said promoter may be a constitutively active promoter. The term "amino acid" or "residue" as used herein includes both L- and D-isomers of the naturally occurring amino acids as well as of other amino acids (e.g., non-naturally-occurring amino acids, amino acids which are not encoded by nucleic acid sequences, synthetic amino acids etc.). Examples of naturally-occurring amino acids are alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophane (Trp; W), tyrosine (Tyr; Y), valine (Val; V). Post-translationally modified naturally-occurring amino acids are dehydrobutyrine (Dhb) and labionin (Lab). Examples for non-naturally occurring amino acids are described above. The non-naturally occurring polypeptide may comprise one or more non-amino acid substituents, or heterologous amino acid substituents, compared to the amino acid sequence of a naturally occurring form of the polypeptide, for example a reporter molecule or another ligand, covalently or non-covalently bound to the amino acid sequence.

The term "nucleotide sequence" or "polynucleotide" is commonly known in the art and comprises molecules comprising or consisting of naturally occurring molecules such as DNA and RNA as well as nucleic acid analogues such as, e.g., oligonucleotides thiophosphates, substituted ribo-oligonucleotides, LNA molecules, PNA molecules, GNA (glycol nucleic acid) molecules, TNA (threose nucleic acid) molecules, morpholino polynucleotides, or nucleic acids with modified backbones such as polysiloxane, and 2—O—(2-methoxy) ethyl-phosphorothioate, or a nucleic acid with substituents, such as methyl-, thio-, sulphate, benzoyl-, phenyl-, amino-, propyl-, chloro-, and methanocarbanucleosides, or a reporter molecule to facilitate its detection. Furthermore, the term "nucleotide sequence" is to be construed equivalently with the term "nucleic acid molecule" in context of the present invention and may inter alia refer to DNA, RNA, PNA or LNA or hybrids thereof or any modification thereof that is known in the art (see, e.g., U.S. Pat. Nos. 5,525,711, 4,711,955, 5,792,608 or EP 302175 for examples of modifications). Nucleic acid residues comprised by the nucleic acid sequence described and provided herein may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). As understood by the person of skill in the art, thymine (T) and uracil (U) may be used interchangeably depending on the respective type of polynucleotide. For example, as the skilled person is aware of, a thymine (T) as part of a DNA corresponds to an uracil (U) as part of the corresponding transcribed mRNA. The polynucleotides described and provided herein may be single- or double-stranded, linear or circular, natural or synthetic.

The nucleotide sequences provided herein may be cloned into a vector. The term "vector" as used herein includes plasmids, cosmids, viruses, bacteriophages and other vectors commonly used in genetic engineering. In a preferred embodiment, these vectors are suitable for the transformation of cells, like mammalian cells or yeast cells. Herein, the vector may be an expression vector. Generally, expression vectors have been widely described in the literature. They may comprise a selection marker gene and a replication-origin ensuring replication in the host, a promoter, and a termination signal for transcription. Between the promoter and the termination signal there may be at least one restriction site or a polylinker which enables the insertion of a nucleic acid sequence desired to be expressed. Non-limiting examples for the vector into which a nucleotide sequence provided herein may be cloned are adenoviral, adeno-associated viral (AAV), lentiviral, HIV-based lentiviral, nonviral minicircle-vectors, or other vectors for bacterial and eukaryotic expression systems.

Herein, the term "compound" means any molecule, including organic molecules such as small molecules, polynucleotides such as RNAi molecules, polypeptides such as antibodies, and inorganic compounds. The term "compound" also includes lipids, hormone analogs, polypeptide ligands, enzymes, receptors, channels, and antibody conjugates. For example, herein the compound may be an RNAi molecule against PAPD5 and/or PAPD7, an antibody that specifically binds to PAPD5 and/or PAPD7, or a small molecule binding to PAPD5 and/or PAPD7.

The term "inhibitor" is known in the art and relates to a compound/substance capable of fully or partially preventing or reducing the physiologic function (i.e. the activity) of (a) specific protein(s) (e.g. of PAPD5 and/or PAPD7). Inhibitors are also known as "antagonists". In the context of the present invention, the inhibitor of PAPD5 and/or PAPD7 may prevent or reduce or inhibit or inactivate the physiological activity of PAPD5 and/or PAPD7, respectively, e.g., upon binding of said compound/substance to PAPD5 and/or PAPD7, respectively. Binding of an inhibitor/antagonist to PAPD5 and/or PAPD7 may reduce the enzymatic function of PAPD5 and/or PAPD7 (i.e. the poly-A polymerase function) or may prevent the binding of an endogenous activating molecule to PAPD5 and/or PAPD7, and thereby inhibiting the activity (i.e. function) of these proteins. In the context of the present invention, an "inhibitor" of PAPD5 and/or PAPD7 may be capable of preventing the activity/function of PAPD5 and/or PAPD7, respectively, by preventing or reducing the expression of the PAPD5 and/or PAPD7 gene. Thus, an inhibitor of PAPD5 and/or PAPD7 may lead to a decreased expression level of PAPD5 and/or PAPD7 (e.g. decreased level of PAPD5 and/or PAPD7 mRNA, or of PAPD5 and/or PAPD7 protein) which is reflected in a decreased functionality (i.e. activity) of PAPD5 and/or PAPD7, wherein said function comprises the poly-A polymerase function. An inhibitor of PAPD5 and/or PAPD7, in the context of the present invention, accordingly, may also encompass transcriptional repressors of PAPD5 and/or PAPD7 expression that are capable of reducing the level of PAPD5 and/or PAPD7. Accordingly, all means and methods that result in a decrease in activity (which may be the result of a lower expression) or PAPD5 and/or PAPD7, are to be used as inhibitors of PAPD5 and/or PAPD7 in accordance with the present invention.

Herein, the term "RNA interference (RNAi) molecule" refers to any molecule inhibiting RNA expression or translation. A small interfering RNA (siRNA) is a double-stranded RNA molecule that, by binding complementary mRNA after transcription, leads to their degradation and loss in translation. A small hairpin RNA (shRNA) is an artificial RNA molecule with a hairpin structure which upon expression is able to reduce mRNA via the DICER and RNA reducing silencing complex (RISC). RNAi molecules can be designed on the base of the RNA sequence of the gene of interest. Corresponding RNAi can then be synthesized chemically or by in vitro transcription, or expressed from a vector or PCR product The term "small molecule" refers to an organic compound with a low molecular weight (<900 daltons). Small molecules may help to regulate a biological process, and have generally a size on the order of $10^{-9}$ m. Many drugs are small molecules.

Herein the term "antibody" is used in the broadest sense and specifically encompasses intact monoclonal antibodies, polyclonal antibodies, multispecific antibodies (e.g., bispecific antibodies) formed from at least two intact antibodies, and antibody fragments, so long as they exhibit the desired biological activity (i.e. specifically binding to PAPD5 and/or PAPD7). Also human, humanized, camelized or CDR-grafted antibodies are comprised."Antibody fragments" comprise a portion of an intact antibody. The term "antibody fragments" includes antigen-binding portions, i.e., "antigen binding sites" (e.g., fragments, subsequences, complementarity determining regions (CDRs)) that retain capacity to bind an antigen (such as PAPD5 and/or PAPD7), comprising or alternatively consisting of, for example, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward; 1989; Nature 341; 544-546), which consists of a VH domain; and (vi) an isolated complementarity determining region (CDR). Antibody fragments or derivatives further comprise F(ab')2, Fv or scFv fragments or single chain antibodies.

The phrase "specifically bind(s)" or "bind(s) specifically" when referring to a binding molecule refers to a binding molecule (e.g. an antibody) which has intermediate or high binding affinity, exclusively or predominantly, to a target molecule, preferably PAPD5 and/or PAPD7. The phrase "specifically binds to" refers to a binding reaction that is determinative of the presence of a target (preferably the PAPD5 and/or the PAPD7 protein) in the presence of a heterogeneous population of proteins and other biologics. Thus, under designated assay conditions, the specified binding molecules bind preferentially to a particular target (preferably the PAPD5 and/or PAPD7 protein) and do not bind in a significant amount to other components present in a test sample. Specific binding to a target protein under such conditions may require a binding molecule that is selected for its specificity for a particular target protein. A variety of assay formats may be used to select binding molecules that are specifically reactive with a particular target protein. For example, solid-phase ELISA immunoassays, immunoprecipitation, Biacore and Western blot may be used to identify binding molecules that specifically react with the PAPD5 and/or PAPD7 protein. The PAPD5 protein is most preferably a polypeptide that has the amino acid sequence as shown in SEQ ID NO: 1 or 2. However, the PAPD5 protein may also be a polypeptide having at least 80%, preferably at least 90%, more preferably at least 95%, even more preferably at least 98%, and even more preferably at least 99% identity to the amino acid sequence of SEQ ID NO: 1 or 2 and being functional, wherein the function is poly-A polymerase function. The PAPD7 protein is most preferably a polypeptide that has the amino acid sequence as shown in SEQ ID NO: 3. However, the PAPD7 protein may also be a polypeptide having at least 80%, preferably at least 90%, more preferably at least 95%, even more preferably at least 98%, and even more preferably at least 99% identity to the amino acid sequence of SEQ ID NO: 3 and being functional, wherein the function is poly-A polymerase function. Typically, a specific or selective reaction will be at least twice background signal or noise and more typically more than 10 times background. Or, in other words, the phrase "specifically binds to" refers to a binding reaction that is determinative of the presence of the target protein (preferably PAPD5 and/or PAPD7) in a heterogeneous population of proteins and other biologics. Typically, an antibody which specifically binds to a certain target (preferably PAPD5 and/or PAPD7) binds to said target with an association constant ($K_a$) of at least about $1 \times 10^6$ $M^{-1}$ or $10^7$ $M^{-1}$, or preferably about $10^8$ $M^{-1}$ to $10^9$ $M^{-1}$, or more preferably about $10^{10}$ $M^{-1}$ to $10^{11}$ $M^{-1}$ or higher. Moreover, an antibody that specifically binds to a particular target (preferably PAPD5 and/or PAPD7) preferably binds to this target with an affinity that is at least two-fold greater than its affinity for binding to a non-specific target (e.g., BSA, casein) other than the predetermined target or a closely-related target.

In context of the present invention, the term "identity" or "percent identity" means that amino acid or nucleotide sequences have identities of at least 80%, preferably at least 90%, more preferably at least 95%, even more preferably at least 98%, and even more preferably at least 99% identity to the sequences shown herein, e.g. those of SEQ ID NO: 1, 2, or 3, wherein the higher identity values are preferred upon the lower ones. In accordance with the present invention, the term "identity/identities" or "percent identity/identities" in the context of two or more nucleic acid or amino acid sequences, refers to two or more sequences that are the same, or that have a specified percentage of amino acid residues or nucleotides that are the same (e.g., at least 80%, at least 90%, at least 95%, at least 98%, or at least 99% identity with the amino acid sequences of, e.g., SEQ ID NO: 1, 2 or 3, or with the nucleotide sequences of, e.g., SEQ ID NO: 4, 5 or 6), when compared and aligned for maximum correspondence over a window of comparison, or over a designated region as measured using a sequence comparison algorithm as known in the art, or by manual alignment and visual inspection.

Preferably the described identity to exists over a region that is at least about 50 amino acids, preferably at least 100 amino acids, more preferably at least 400 amino acids, more preferably at least 500 amino acids, more preferably at least 600 amino acids and most preferably all amino acids in length. In case of nucleotide sequences, the described identity most preferably exists over a region that is at least 100 nucleotides, preferably at least 1,000 nucleotides, more preferably at least 2,000 nucleotides and most preferably all nucleotides in length.

Those having skills in the art will know how to determine percent identity between/among sequences using, for example, algorithms such as those based on CLUSTALW computer program (Thompson, 1994, Nucl Acids Res, 2: 4673-4680) or FASTDB (Brutlag, 1990, Comp App Biosci, 6: 237-245), as known in the art. Also available to those having skills in this art are the BLAST and BLAST 2.0 algorithms (Altschul, 1997, Nucl Acids Res 25: 3389-3402; Altschul, 1993, J Mol Evol, 36: 290-300; Altschul, 1990, J Mol Biol 215: 403-410). For example, BLAST 2.0, which stands for Basic Local Alignment Search Tool BLAST (Altschul, 1997, loc. cit.; Altschul, 1993, loc. cit.; Altschul, 1990, loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. Analogous computer techniques using BLAST (Altschul, 1997, loc. cit.; Altschul, 1993, loc. cit.; Altschul, 1990, loc. cit.) are used to search for identical or related molecules in nucleotide databases such as GenBank or EMBL.

Herein, the term "measuring" also means "analyzing" or "determining" (i.e. detecting and/or quantifying). For example, the term "measuring the expression and/or activity of PAPD5 and/or PAPD7" means determining the amount of PAPD5 and/or PAPD7 expression and/or activity, for example, determining the amount of the PAPD5 and/or PAPD7 polypeptide (i.e. protein). Methods for measuring (i.e. determining) the amount and/or activity of PAPD5 and/or PAPD7 protein are known in the art and described herein above. Analogously, the term "measuring whether a test compound binds to PAPD5 and/or PAPD7" means analyzing or determining (i.e. detecting) whether a test compound binds to PAPD5 and/or PAPD7, e.g. to the PAPD5 polypeptide (i.e. protein) and/or to the PAPD7 polypeptide (i.e. protein). In line with this, the term "measuring whether a test compound inhibits propagation of HBV" means analyzing or determining (i.e. detecting and/or quantifying) whether a test compound inhibits propagation of HBV.

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{2-6}$alkenyl" denotes an unsaturated, linear or branched chain alkenyl group containing 2 to 6, particularly 2 to 4 carbon atoms, for example vinyl, propenyl, allyl, butenyl and the like. Particular "$C_{2-6}$alkenyl" group is allyl and vinyl.

The term "$C_{2-6}$alkynyl" denotes an unsaturated, linear or branched chain alkynyl group containing 2 to 6, particularly 2 to 4 carbon atoms, for example ethynyl, 1-propynyl, propargyl, butynyl and the like. Particular "$C_{2-6}$alkynyl" groups are ethynyl and 1-propynyl.

The term "$C_xH_{2x}$" alone or in combination signifies a saturated, linear- or branched chain alkyl group containing 1 to 6, particularly 1 to 4 carbon atoms. The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-bu-toxy, 2-butoxy, tert-butoxy, pentoxy, hexyloxy and the like. Particular "$C_{1-6}$alkoxy" groups are methoxy, ethoxy and propoxy.

The term "halogen" means fluorine, chlorine, bromine or iodine.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "halo$C_{1-6}$alkyl" group is difluoromethyl or trifluoromethyl.

The term "halo$C_{1-6}$alkoxy" denotes a $C_{1-6}$alkoxy group wherein at least one of the hydrogen atoms of the $C_{1-6}$alkoxy group has been replaced by same or different halogen atoms, particularly fluoro atoms. Examples of halo$C_{1-6}$alkoxyl include monofluoro-, difluoro- or trifluoro-methoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "halo$C_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "halo$C_{3-7}$cycloalkyl" denotes a $C_{3-7}$cycloalkyl group wherein at least one of the hydrogen atoms of the $C_{3-7}$cycloalkyl group has been replaced by same or different halogen atoms, particularly fluoro atoms. Examples of halo$C_{3-7}$cycloalkyl include monofluoro- or difluoro-cyclo-propyl, -cyclobutyl, -cyclopentyl or -cyclohexyl, for example fluorocyclopropyl, difluorocyclopropyl, fluocyclobutyl, difluocyclobutyl, fluocyclopentyl, difluocyclopentyl, fluocyclohexyl or difluocyclohexyl. Particular "halo$C_{1-6}$alkyl" group is difluorocyclopropyl.

With respect to formula (I) the term "amino", alone or in combination, refers to primary (—$NH_2$), secondary (—NH—) or tertiary amino

With respect to formula (II) the term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero$C_{3-7}$cycloalkyl.

The term "carbonyl" alone or in combination refers to the group —C(O)—.

The term "cyano" alone or in combination refers to the group —CN.

The term "$C_{1-6}$alkylsulfinyl" denotes a group —SO—$C_{1-6}$alkyl, wherein $C_{1-6}$alkyl group is defined above. Examples of $C_{1-6}$alkylsulfinyl include methylsulfinyl and ethylsulfinyl.

The term "$C_{1-6}$alkylsulfonyl" denotes a group —$SO_2$—$C_{1-6}$alkyl, wherein $C_{1-6}$alkyl group is defined above. Examples of $C_{1-6}$alkylsulfonyl include methylsulfonyl and ethylsulfonyl.

The term "monocyclic heteroaryl" denotes a monovalent aromatic heterocyclic mono-ring system of 5 to 8 ring atoms, comprising 1, 2, 3 or 4 heteroatoms selected from N, O and S, the remaining ring atoms being carbon. Examples of monocyclic heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, isothiazolyl and the like.

With regard to formula (I) the term "monocyclic heterocycloalkyl" refers to a monovalent saturated or partly unsaturated monocyclic ring system of 3 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Particular "monocyclic heterocycloalkyl" groups are morpholinyl, 2-oxo-pyrrolidinyl, pyrrolidinyl, tetrahydropyranyl, and more particularly pyrrolidin-1-yl, 2-oxo-pyrrolidin-1-yl, tetrahydropyran-4-yl and morpholin-1-yl.

With regard to formula (II) the term "monocyclic heterocycloalkyl" is a monovalent saturated or partly unsaturated monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, thietanyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, 2-oxomorpholinyl, 2-oxo-piperazinyl, thiomorpholinyl, 1,1-dioxo-thiomorpholin-4-yl, 1,1-dioxothiolanyl, 1,1-dioxothietanyl, oxoimidazolidinyl, azepanyl, diazepanyl, homopiperazinyl, or oxazepanyl. Particular "monocyclic heterocycloalkyl" groups are azetidinyl, oxetanyl, thietanyl, tetrahydrofuranyl, tetrahydropyranyl, 1,1-dioxothietanyl, 1,1-dioxothiolanyl, morpholinyl, pyrrolidinyl, piperidinyl, piperazinyl, oxoimidazolidinyl, 2-oxo-pyrrolidinyl, 2-oxomorpholinyl and 2-oxo-piperazinyl. More particularly, "monocyclic heterocycloalkyl" groups are azetidinyl, pyrrolidinyl, morpholinyl, oxomorpholinyl, piperidinyl, piperazinyl and oxopiperazinyl.

The term "aryl" denotes a monovalent aromatic carbocyclic mono- or bicyclic ring system comprising 6 to 10 carbon ring atoms. Examples of aryl moieties include phenyl and naphthyl, Particular "aryl" is phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular "heteroaryl" are pyridinyl and pyrimidinyl.

The term "N-containing monocyclic heteroaryl" refers to a monocyclic heteroaryl wherein at least one of the heteroatoms is N. Examples for N-containing monocyclic heteroaryl are pyrrolyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, isothiazolyl and the like. Particular "N-containing monocyclic heteroaryl" groups are imidazolyl, pyrazolyl and triazolyl, and more particularly imidazol-1-yl, pyrazol-1-yl and 1,2,4-triazol-1-yl.

The term "halogen" means fluorine, chlorine, bromine or iodine. Halogen is particularly fluorine, chlorine or bromine.

The term "hydroxy" alone or in combination refers to the group —OH.

The term "2-oxo-pyrrolidinyl" alone or in combination refers to the group.

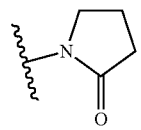 [SMILES: *N1CCCC1=O]

The term "sulfonyl" alone or in combination refers to the group —$S(O)_2$—.

The term "$C_{1-6}$alkylamino" refers to amino group as defined above wherein at least one of the hydrogen atoms of the amino group is replaced by a $C_{1-6}$alkyl group.

The term "$C_{1-6}$alkylsulfonyl" refers to a group $C_{1-6}$alkyl-$S(O)_2$—, wherein the "$C_{1-6}$alkyl" is as defined above.

The term "aminocarbonyl" refers to a group amino-C(O)—, wherein the "amino" is as defined above.

The term "cyano$C_{3-7}$cycloalkyl" refers to $C_{3-7}$cycloalkyl group as defined above wherein at least one of the hydrogen atoms of the $C_{3-7}$cycloalkyl group is replaced by a cyano group.

The term "pyrrolidinylcarbonyl" refers to a group pyrrolidinyl-C(O)—.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The present invention is further described by reference to the non-limiting figures and examples.

EXAMPLES

The Examples illustrate the invention.
Material and Methods
Compound Chemistry

Each one compound from the two chemical series DHQ and THP were synthesized to be suitable for the Y3H screening performed by HYBRIGENICS SERVICES SAS. Both compounds included PEGS linker and were tagged with a Trimethoprim (TMP) anchor ligand (Table 1).

TABLE 1

TMP-tagged compound IDs

| | Hybrigenics ID | Structure |
|---|---|---|
| DHQ compound-TMP | HBX129653 | 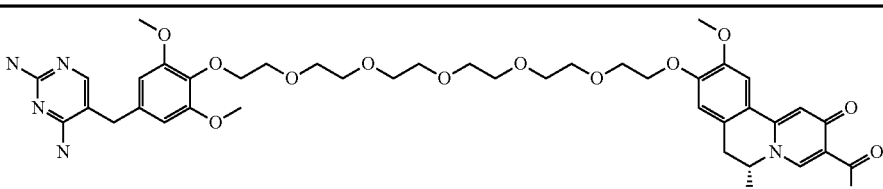 |
| THP compound-TMP | HBX129654 | 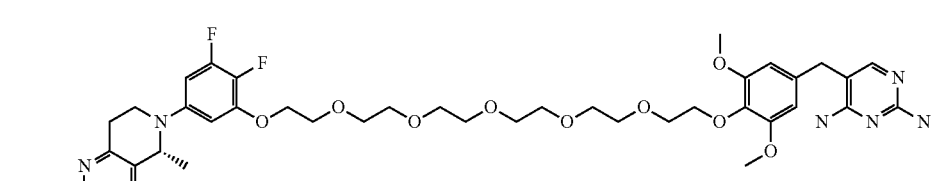 |

Y3H ULTImate YChemH™ Screen

The two compounds were provided by Roche to HYBRIGENICS SERVICES SAS and tested for permeability and toxicity. Compounds were then screened against HYBRIGENICS's cDNA Human placenta library (PLA). The screens were carried out according to the optimized cell-to-cell mating protocol developed for Hybrigenics ULTImate Y2H™ using at different compound concentration (Table 2).

TABLE 2

YChemH screens IDs

| | Hybrigenics ID | YChemH Project | YChemH screen Project ID | Probe concentration |
|---|---|---|---|---|
| DHQ compound | HBX129653 | hgx4240 | PLA_RP6_hgx4240v1_pB409_A | 5 µM |
| THP compound | HBX129654 | hgx4241 | PLA_RP6_hgx4241v1_pB409_A | 10 µM |

Y3H ULTImate YChemH™ Dependency Assay

Clones obtained from the screen were picked in 96-well format and clones positive for growth under selective conditions (HIS+) were evaluated in a dependency assay using spot assays. Only clones that were able to grow on selective medium in the presence of the tagged compound were being picked up, processed (cell lysis, PCR, gene sequencing) and mapped for protein alignment using Blast analysis.

Y3H ULTImate YChemH™ 1-by-1 Validation Experiment—Prey Fragments

In this validation step each one identified fragment prey and one chemical probe (HBX129653, HBX129654) is tested in a 1-by-1 experiment. The plasmids from 3 selected preys from the screening library were extracted from the yeast cells, amplified in E. coli and re-transformed into YHGX13 yeast cells. For each interaction, DO1, 1/10, 1/100 and 1/1000 of the diploid yeast culture expressing both hook and prey constructs were spotted on a selective medium without tryptophan, leucine and histidine and supplemented with the chemical probe and FK506. Interactions were tested in duplicate. One plate was used per chemical compound and concentration (DMSO, 5, 10 and 20 µM of HBX129653, 5, 10 and 20 µM of HBX129654, 5 µM of HBX24786 Trimethoprim (TMP) and 5 µM of HBX129634 (TMP-PEG5-OH)). Plates were incubated at 30° C. for 3 days.

Y3H ULTImate YChemH™ 1-by-1 Validation Experiment—Full Length Proteins

The coding sequence of full-length PAPD5var1 (NM_001040284.2) and PAPD7varX1 (XM_005248234.2) were reconstituted from an N-terminal codon-optimized gene fragment (to remove high GC content) and commercially available clones of the C-terminal regions of the proteins and cloned in frame with the Gal4 Activation Domain (AD) into plasmid pP7 (AD-Prey), derived from the original pGADGH (Bartel et al., 1993 in Cellular interactions in development: A practical approach. ed. Hartley, D. A., Oxford University Press, Oxford, pp. 153-179). The constructs were checked by sequencing the entire inserts. For each prey, a mini-mating was carried out between YHGX13 (Y187 ade2-101::loxP-kanMX-loxP, matα) transformed with the prey plasmids and YPT6AT yeast cells (mata) transformed with the DHFR hook (Dihydrofolate reductase) to produce a diploid yeast culture. For each interaction, DO1, 1/10, 1/100 and 1/1000 of the diploid yeast culture expressing both hook and prey constructs were spotted on a selective medium without tryptophan, leucine and histidine and supplemented with the chemical probe and FK506. Interactions were tested in duplicate. One plate was used per chemical compound and concentration (DMSO, 5, 10 and 20 µM of HBX129653, 5, 10 and 20 µM of HBX129654, 5 µM of HBX24786 Trimethoprim (TMP) and 5 µM of HBX129634 (TMP-PEG5-OH)). Plates were incubated at 30° C. for 3 days.

Y3H ULTImate YChemH™—Competition with Free Compound

The competition assay is based on the previously described 1-by-1 validation with a constant concentration for the chemical probe (HBX129653, HBX 129654) and increasing concentrations of the parent compound of the chemical probe (MOL653, MOL654) or its inactive enantiomer (INACT653, INACT654) (Table 3). The competition assays were performed on selective medium at 8 concentrations of the free compound (0, 0.25, 0.5, 1, 2, 5, 10 and 20 μM) and a consistent concentration for the tagged Y3H-compound (1 μM).

medium consisting of William's E Medium (GIBCO), Growth Medium Supplement (Biopredics, Cat #ADD710) and 1% (v/v) GlutaMAX-I (Gibco #32551) and 1×Pen/Strep (Gibco, #15140) for 2 weeks. To initiate differentiation, 0.9% (v/v) DMSO (Sigma-Aldrich, D2650) was added to the growth medium on confluent cells. After one week, medium was replaced by complete differentiation medium (HepaRG growth medium supplemented with 1.8% (v/v) DMSO) in which cells were maintained for approximately 4 weeks with differentiation medium renewal every 7 days. Differentiated HepaRG cells (dHepaRG), displayed hepatocyte-like cell islands surrounded by monolayer of biliary-

TABLE 3

YChemH competitions IDs

| | Hybrigenics ID | Structure |
|---|---|---|
| DHQ compound-active | MOL653 | 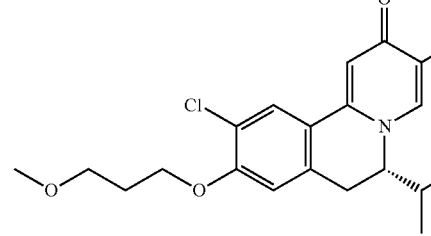 |
| DHQ compound-inactive | INACT653 | 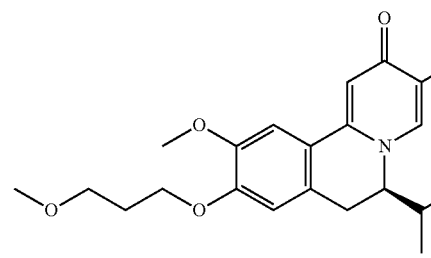 |
| THP compound-active | MOL654 | 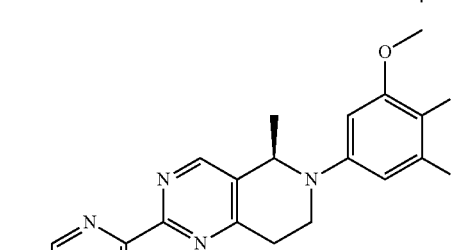 |
| THP compound-inactive | INACT654 | 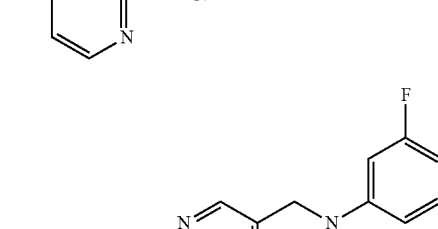 |

HepaRG Cell Culture

HepaRG cells (Biopredics International, Rennes, France, Cat #HPR101) were cultured at 37° C. in a humidified atmosphere with 5% CO2 in complete HepaRG growth like cells. Prior to HBV infection and compound treatment, dHepaRG cells were seeded into collagen I coated 96-well plates (Gibco, Cat #A11428-03) at 60,000 cells per well in 100 μL of complete differentiation medium. Cells were allowed to recover their differentiated phenotype in 96-well plates for approximately 1 week after plating prior to HBV infection.

HBV Infection of dHepaRG dHepaRG cells were infected with HBV particles at an MOI of 30. The HBV particles were produced from HBV-producing HepG2.2.15 cells (Sells et al 1987 Proc Natl Acad Sci USA 84, 1005-1009). dHepaRG culture conditions, differentiation and HBV infection have been described previously (Hantz, 2009, J. Gen. Virol., 2009, 90: 127-135). In brief complete differentiation medium (120 µL/well) containing 4% PEG-8000 and virus stock (20 to 30 GE/cell) was added. One day post-infection, the cells were washed three times with phosphate-buffered saline and medium (complete differentiation medium) was replaced every two days during the experiment.

siRNA Treatment of HBV-Infected HepaRG

A pool of four different siRNAs was acquired from GE Dharmacon (ON TARGETplus) (Table 4).

TABLE 4

Overview siRNAs

| ON TARGETplus | siRNA (Cat.No.) | Target Sequence | SEQ ID NO |
|---|---|---|---|
| siPAPD5 (Cat. No. L-010011-00-0010) | # J-010011-05 | CAUCAAUGCUUUAUAUCGA | 10 |
| | J-010011-06 | GGACGACACUUCAAUUAUU | 11 |
| | J-010011-07 | GAUAAAGGAUGGUGGUUCA | 12 |
| | J-010011-08 | GAAUAGACCUGAGCCUUCA | 13 |
| siPAPD7 (Cat. No. L-009807-00-0005) | # J-009807-05 | GGAGUGACGUUGAUUCAGA | 14 |
| | J-009807-06 | CGGAGUUCAUCAAGAAUUA | 15 |
| | J-009807-07 | CGGAGUUCAUCAAGAAUUA | 16 |
| | J-009807-08 | GCGAAUAGCCACAUGCAAU | 17 |

One day before infection with HBV cells and 4 days after infection cells were treated with siRNA pool either against PAPD5, PAPD7, both or the non-targeting siRNA as control. The siRNAs were transfected using DharmaFect 4 (GE Dharmacon; Cat. No. T-2004-01) and OPTI-MEM (Thermo Scientific; Cat. No. 51985034) according to manufacturer's protocol. The cells were treated for 11 days.

HBV Antigen Measurements

To evaluate the impact on HBV antigen expression and secretion, supernatants were collected on Day 11. HBV HBsAg and HBeAg levels were measured using CLIA ELISA Kits (Autobio Diagnostic #CL0310-2, #CL0312-2), according to the manufacturer's protocol. Briefly, 25 µL of supernatant per well were transferred to the respective antibody coated microtiter plate and 25 µL of enzyme conjugate reagent were added. The plate was incubated for 60 min on a shaker at room temperature before the wells were washed five times with washing buffer using an automatic washer. 25 µL of substrate A and B were added to each well. The plates were incubated on a shaker for 10 min at room temperature before luminescence was measured using an Envision luminescence reader (Perkin Elmer).

Cell Viability

After the removal of supernatant media from the HBV infected dHepaRG cells, cells were incubated with CellTiterGlo One Solution (Promega) to measure cell viability.

Real-Time PCR for Intracellular mRNA

For intracellular mRNA isolation, dHepaRG were washed once with PBS (Gibco) and lysed using the MagNA Pure "96 Cellular RNA Large Volume Kit" (Roche #05467535001). The lystates may be stored at −80° C. For the real-time qPCR reaction an AB7900 HT sequence detection system (Applied Biosystems), the TaqMan® Gene Expression Master Mix (Thermo Fisher Scientific) were used. For detection of HBV mRNA HBV core-specific primer (Integrated DNA Technologies) (Table 5) and to measure reduction of PAPD5 and PAPD7, in the presence of siRNA, gene-specific TaqMan® Expression Assay probes (ThermoFisher Scientific; PAPD5 Cat. No. 4331182; PAPD7 Cat. No. 4331182) were used. Samples were normalized using TaqMan® Expression Assay probe against b-Actin (ThermoFisher Scientific; PAPD5 Cat. No. 4331182).

TABLE 5

HBV core specific TaqMan probes

| | Name | Dye | Sequence | SEQ ID NO |
|---|---|---|---|---|
| HBV core Primer | Forward (F3_HBVcore) | | CTG TGC CTT GGG TGG CTT T | 18 |
| | Reverse (R3_HBVcore) | | AAG GAA AGA AGT CAG AAG GCA AAA | 19 |
| | Probe (P3_HBVcore) | FAM-MGB | AGC TCC AAA/ZEN/TTC TTT ATA GGG TCA GAT GTC CAT G | 20 |

Example 1

DHQ and THP Binds to PAPD5 and PAPD7

PAPD5/7 were Identified in Y3H Ultimate YChemH Screen as Common Interaction Partner of DHQ and THP Both proteins PAPD5 (variant 1: NP_001035374; variant 2: NP_001035375) and PAPD7 (XP_005248291) were identified by a numerous number of fragments in the Y3H screen for both compounds (DHQ and THP) as described in the Materials and Method section. The identified proteins were ranked with a confidence score of A (scale A-D) by HYBRIGENICS (Table 6).

TABLE 6

YChemH screen results for PAPD5/7

| | Hybrigenics ID | Protein prey identified | # of fragments | Confidence score |
|---|---|---|---|---|
| DHQ compound | HBX129653 | PAPD5 variant 1 | 28 | A |
| | | PAPD5 variant 2 | 1 | N/A |
| | | PAPD7 | 12 | A |
| THP compound | HBX129654 | PAPD5 variant 1 | 5 | N/A |
| | | PAPD5 variant 2 | 49 | A |
| | | PAPD7 | 24 | A |

PAPD5/7 Interaction with DHQ and THP Could be Confirmed Using Y3H ULTImate YChemH 1-by-1 Validation of Identified Prey Fragments and Further with Full Length Proteins In a first validation step three fragments identified in the first screen were selected for the 1-by-1 validation assay (as described in the Materials and Method section) and tested at three different concentrations (5, 10 and 20 µM) (Table 7).

TABLE 7 interacting fragment selected for validation assay

| Interaction # | Prey fragment ID | Protein Prey |
|---|---|---|
| A | PLA_RP6_hgx4240v1_pB409_A-15 | PAPD7 |
| B | PLA_RP6_hgx4241v1_pB409_A-112 | PAPD5 variant 1 |
| C | PLA_RP6_hgx4240v1_pB409_A-24 | PAPD5 variant 2 |

All three fragments could be validated as specific binders for DHQ and THP already at the lowest tested concentration (FIG. 1).

In a second validation step, full length proteins for PAPD5 and PAPD7 were synthesized and used for 1-by-1 validation (as described in the Materials and Method section) with DHQ and THP (Table 8).

TABLE 8

Reference ID for full length protein prey used in 1-by-1 validation assay

| Interaction # | HYBRIGENICS Reference | Protein Prey |
|---|---|---|
| A | hgx4386v1_pP7 | PAPD5 var1 full length |
| B | hgx4388v2_pP7 | PAPD7 var1 full length |

Figure 2:
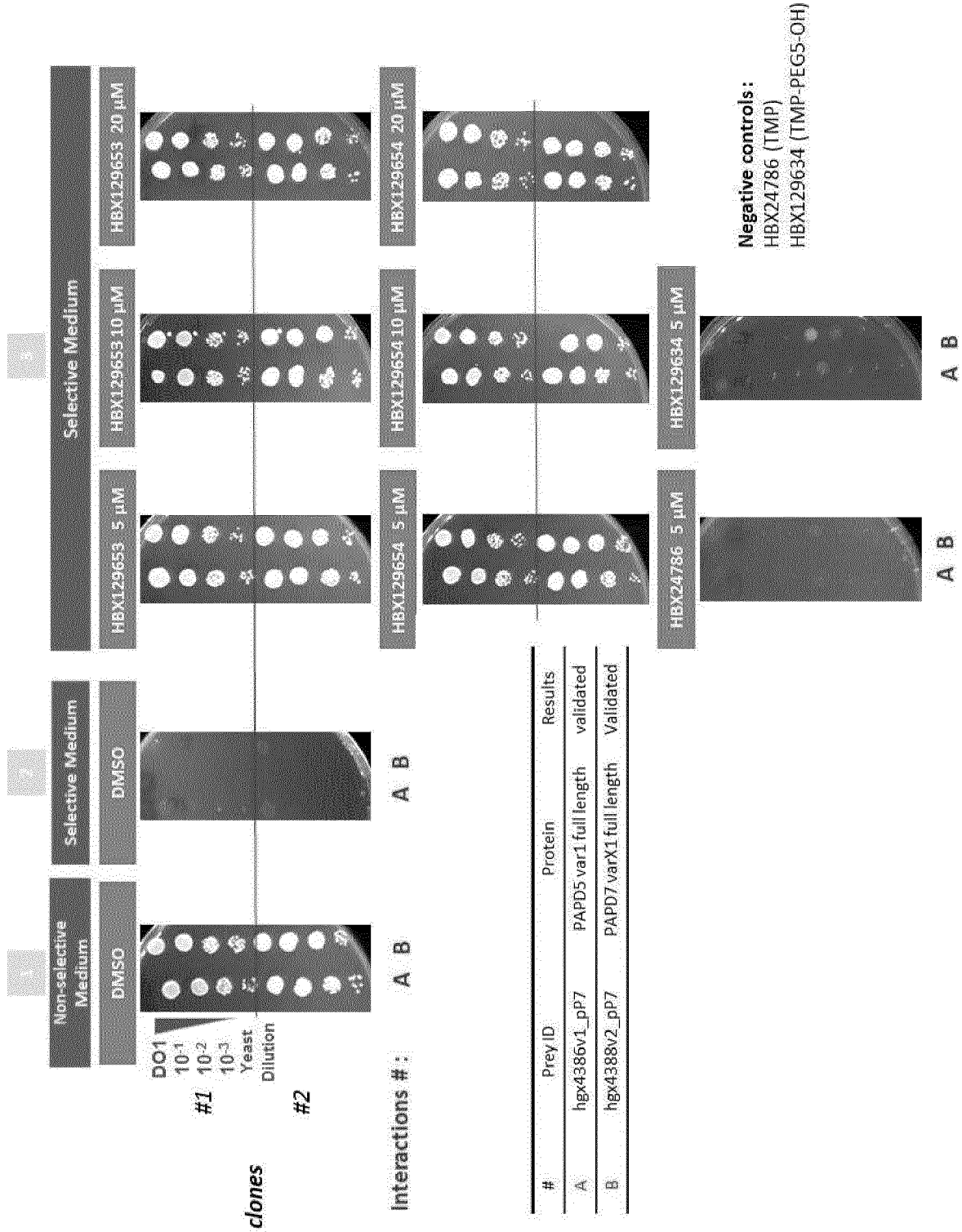
FIG. 2: Pictures from 1-by-1 experiment with HBX129653/HBX129654 chemical probes and PAPD5/7 full length proteins.

The interaction between these full length proteins and the DHQ and THP compounds were confirmed at the lowest tested concentration and shown to be specific for the chemical probes (FIG. 2).

PAPD5/7 Interaction with DHQ and THP in Y3H Can Be Competed By Both Free Active Compound, But Not the Inactive Enantiomer After validation of binding of DHQ and THP to protein fragments and full length PAPD5 and PAPD7 the binding was confirmed in a Y3H ULTImate YChenH competition experiment (as described in the Materials and Method section) using either inactive or active free compound (Table 9). A decrease of loss of yeast growth in the presence of the parent active compound, but not in the presence of the inactive enantiomer, means that the parent compound competes with the chemical probe and interacts with the protein target.

Figure 3:
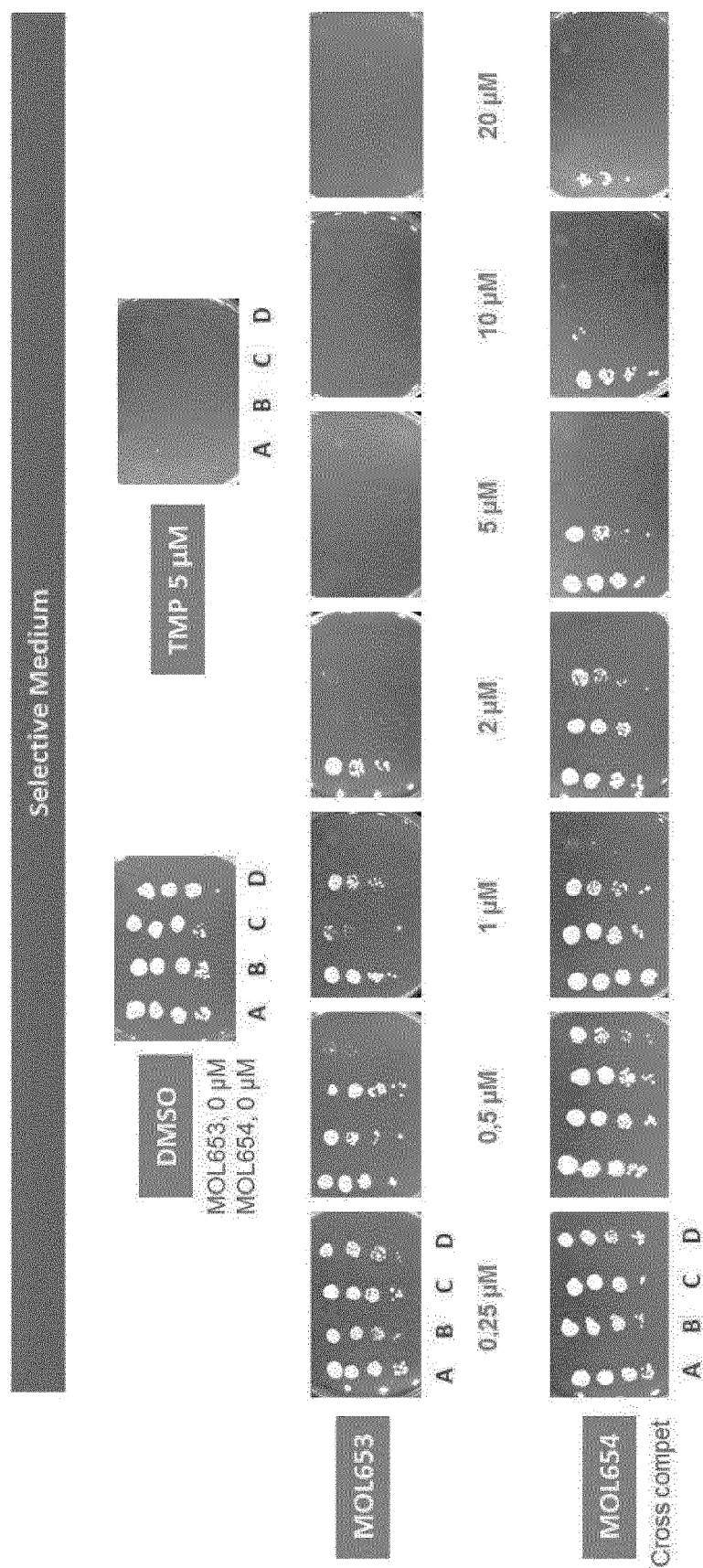
FIG. 3: Pictures from competition assay using HBX129653 (DHQ) and MOL653/654 for competition
Figure 4:
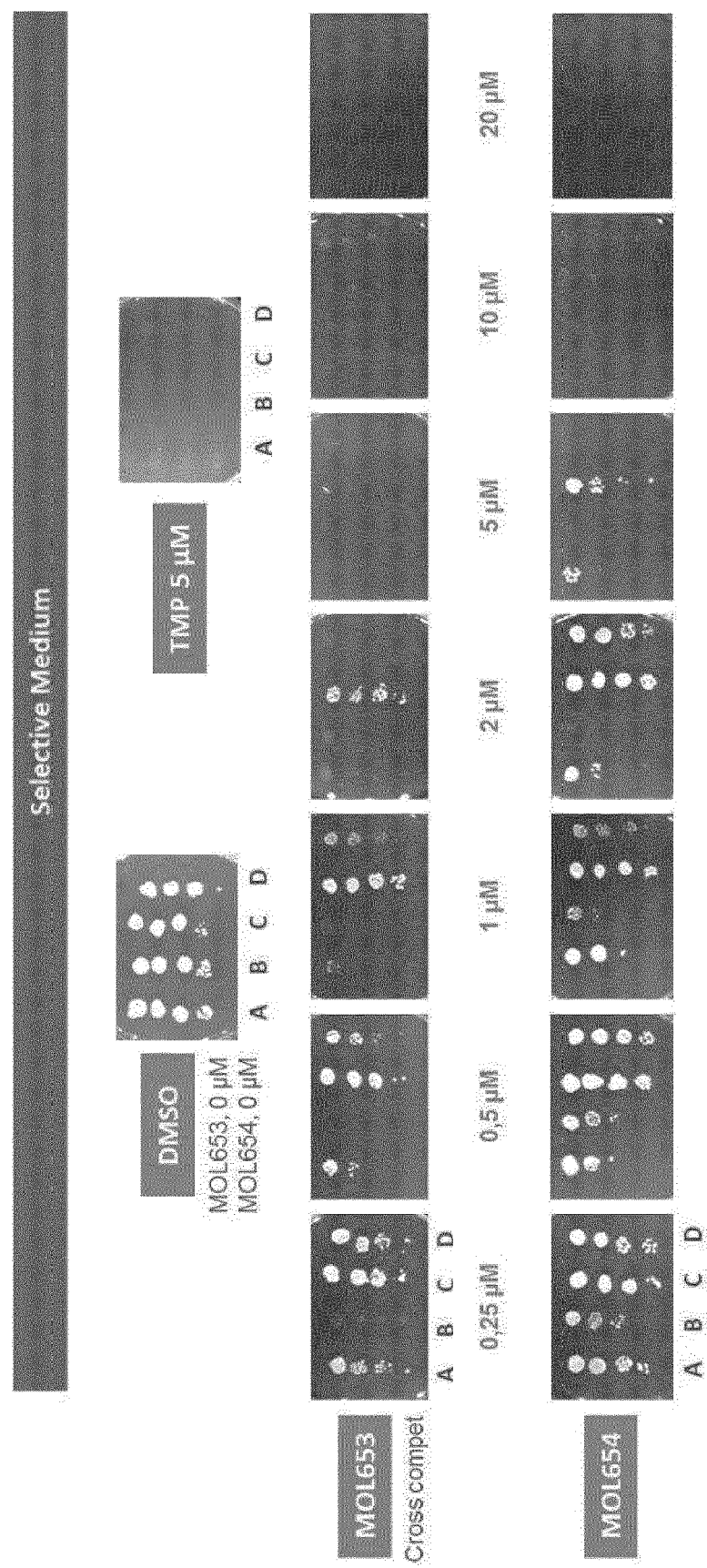
FIG. 4: Pictures from competition assay using HBX129654 (THP) and MOL653/654 for competition
Figure 5:
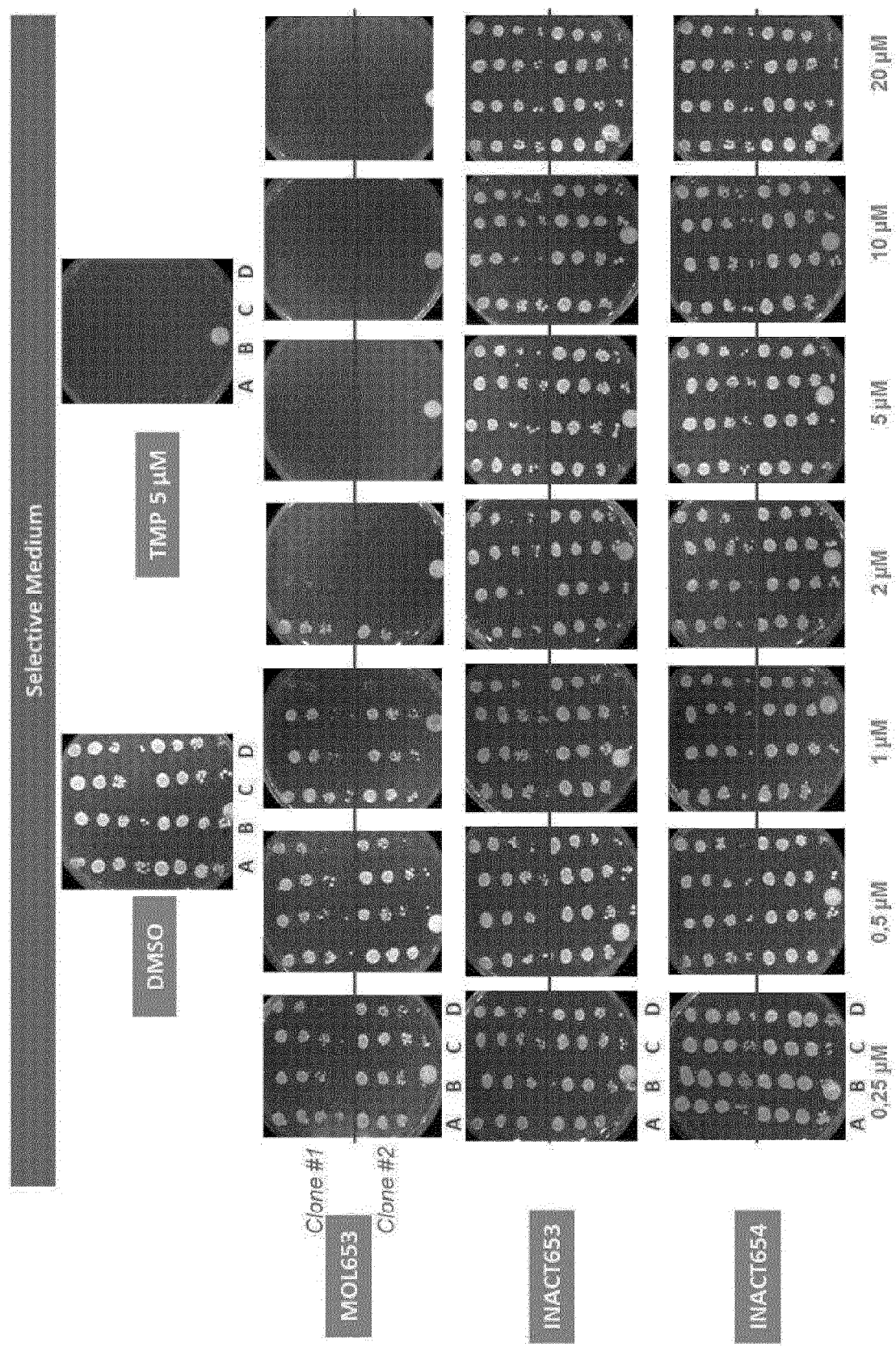
FIG. 5: Pictures from competition assay using HBX129653 (DHQ) and INACT653/INACT654 for competition. MOL653 was included as positive control.
Figure 6:
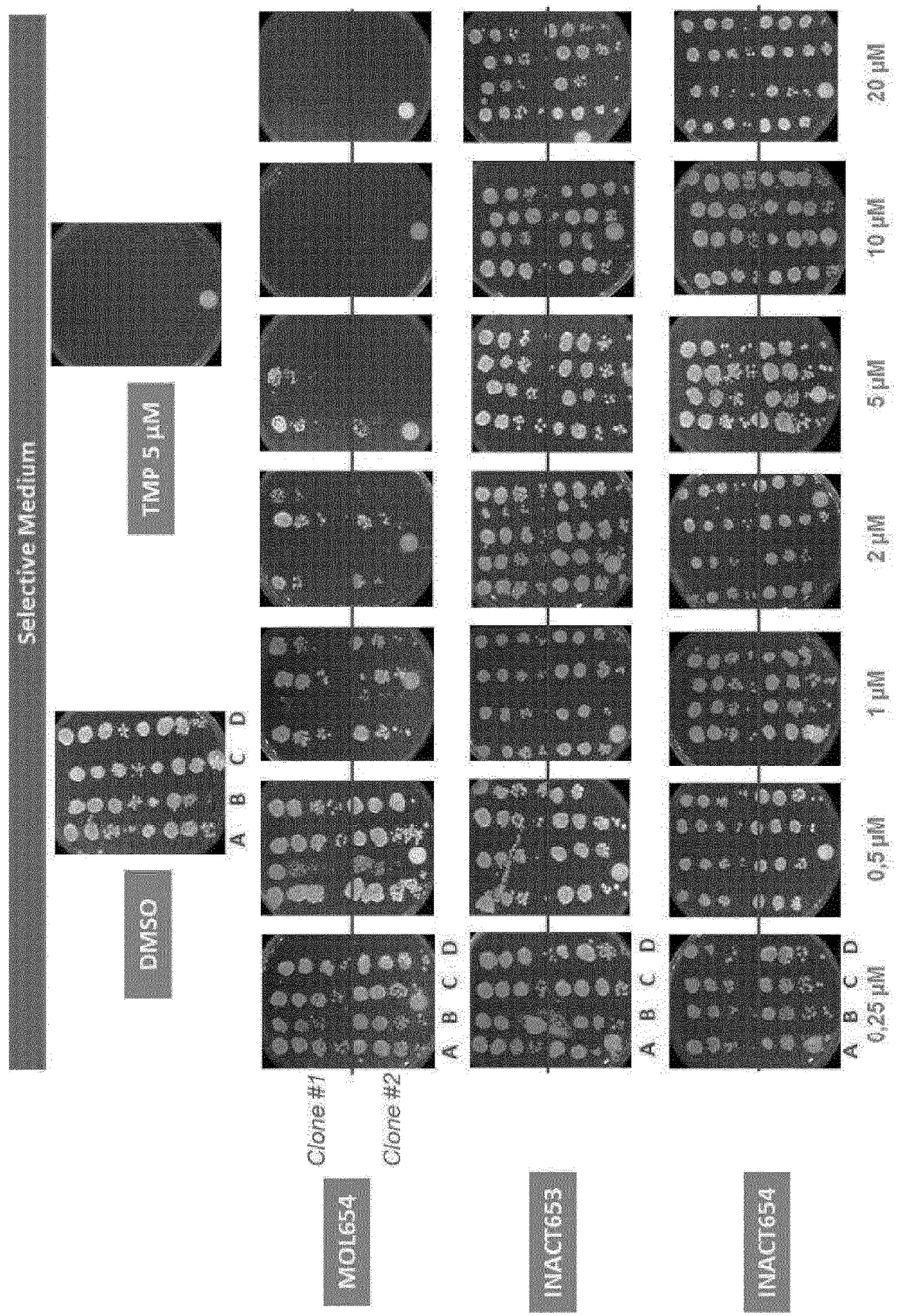
FIG. 6: Pictures from competition assay using HBX129654 (THP) and INACT653/INACT654 for competition. MOL653 was included as positive control.

For all tested compounds toxicity on non-selective medium at the highest concentration (20 µM) was tested using CellTiter-Glo Luminescent Cell Viability Assay (Promega) according to the manufacturer's protocol. No toxicity was observed at this concentration for any compound as yeast growth was not affected (data not shown). For both active free parent compounds (DHQ and THP, MOL653 and MOL654, respectively) competition could be observed, with lower concentration needed for competing the binding to the full length protein than for the fragment interactions (FIG. 3+4). Successful cross competition suggests a shared binding side for DHQ and THP to PAPD5/7 or at least binding in close proximity to each other.

TABLE 9

Reference ID for protein prey used in competition assay

| Interaction # | Prey fragment ID | Protein Prey |
|---|---|---|
| A | PLA_RP6_hgx4241v1_pB409_A-112 | PAPD5 var1 experimental fragment |
| B | hgx4386v1_pP7 | PAPD5 var1 full length |
| C | PLA_RP6_hgx4240v1_pB409_A-15 | PAPD7 varX1 experimental fragment |
| D | hgx4388v2_pP7 | PAPD7 varX1 full length |

Example 2

Inhibition of PAPD5 and/or PAPD7 with siRNA Results in Effective Treatment of HBV Infection To correlate the binding of DHQ and THP to PAPD5/7 and the impact of these two proteins on HBV gene expression, we used RNAi technology to reduce these proteins in naturally HBV infected dHepaRG and to monitor the impact of this reduction on viral parameters. For that we used siRNA pools against PAPD5 and PAPD7 (see table 4) in HBV infected dHepaRG cells as described in the Materials and methods section.

Figure 7:
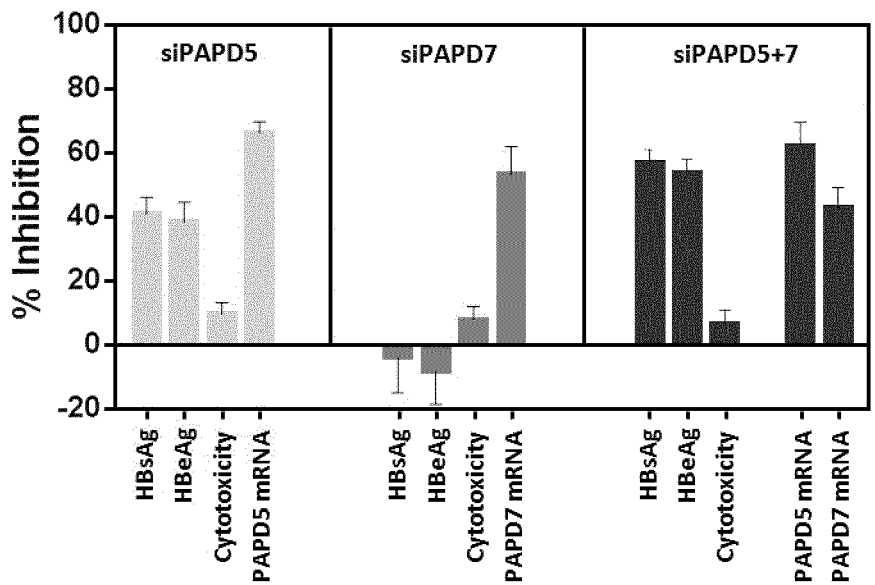
FIG. 7: (A) SiRNA knock-down (KD) of PAPD5 and PAPD7 in HBV-infected dHepaRG leads to reduction in HBV expression. Differentiated HepaRG cells were infected with HBV and treated with siRNA against either PAPD5, PAPD7 or both (25 nM each) one day prior to HBV infection and on day 4 post infection. Supernatant were harvested on day 11, levels of HBsAg and HBeAg secreted in the supernatant were measured by ELISA and normalized to non-treated control. Cell toxicity and inhibition of gene expression was measured subsequently and also normalized to the non-treated control. (B) The same experiment as described in (A) was performed, with the exception that only the level of HBsAg secreted in the supernatant was measured.
Figure 7:
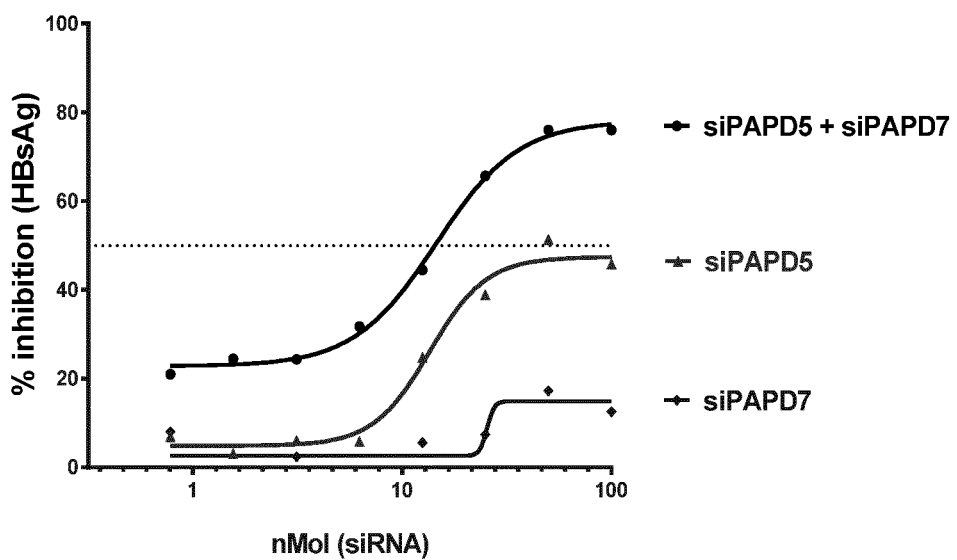

Reduction of PAPD5 led to inhibition of viral expression measured by secreted HBsAg and HBeAg as well as intracellular HBV mRNA (measured using CLIA ELISA and real-time PCR as described in the Materials and Methods section). While the reduction of PAPD5 mRNA dramatically reduced HBV gene expression, inhibition of PAPD7 had a modest effect on HBV expression (FIG. 7). However, an enhanced synergistic anti-HBV activity was observed when siRNA against PAPD7 and PAPD5 were combined (FIG. 7), suggesting a compensative role for PAPD7 in the absence of PAPD5.

Example 3

DHQ and THP Effectively Reduces HBsAg and HBeAg

The potency of DHQ and THP and their variants against HBV infection were measured in HepG2.2.15 cells using HBsAg and HBeAg as read out.

HepG2.2.15 cells (Sells et al 1987 Proc Natl Acad Sci USA 84, 1005-1009) were cultured in 96 well plates (15.000 cells/well in 100 uL) in DMEM+GluTaMax-1 (GiBCO Cat. NO. 10569), 1% Pen Strep (Gibco Cat. No. 15140), 10% FBS (Clontech Cat. No. 631106), Geneticin 0.25 ug/ml (Invitrogen 10131035). The compunds were tested using three-fold serial dilutions in DMSO with a top concentration of 100 µM and 9 serial dilutions. Each compound was tested in quadricate. The cells were incubated for 3 days, supernatents were collected and HBsAg and HBeAg were measured as described in the Materials and Methods section. The $IC_{50}$ values of the tested compounds in the reduction of secretion of HBsAg and HBeAg are shown in the following:
HBX129653 (DHQ—TMP): $IC_{50}$ HBsAg 1.181 uM
HBX129654 (THP—TMP): $IC_{50}$ HBsAg 0.299 uM
MOL653 (DHQ—free-active): $IC_{50}$ HBsAg 0.003 uM; $IC_{50}$ HBeAg 0.007 uM
MOL654 (THP—free-active): $IC_{50}$ HBsAg 0.003 uM
INACT653 (DHQ—free-inactive): $IC_{50}$ HBsAg 3.15 uM
INACT654 (THP—free-inactive): $IC_{50}$ HBsAg >25 uM

---

The invention claimed is:

1. A method for identifying a compound that ameliorates and/or inhibits a hepatitis B virus (HBV) infection, comprising:
   a. contacting a test compound with
      i. poly(A) polymerase associated domain containing protein 5 (PAPD5) polypeptide and/or poly(A) polymerase associated domain containing protein 7 (PAPD7) polypeptide; or
      ii. a cell expressing PAPD5 and/or PAPD7;
   b. measuring the expression and/or activity of PAPD5 and/or PAPD7 in the presence and absence of said test compound; and
   c. identifying a compound that reduces the expression and/or activity of PAPD5 and/or PAPD7 as a compound that ameliorates and/or inhibits a HBV infection.

2. A method for identifying a compound that ameliorates and/or inhibits a HBV infection, comprising:
   a. contacting a test compound with
      i. PAPD5 and/or PAPD7 polypeptide; or
      ii. a cell expressing PAPD5 and/or PAPD7;

b. measuring whether the test compound binds to the PAPD5 and/or to PAPD7 polypeptide;
c. measuring whether the test compound inhibits propagation of HBV; and
d. identifying a compound that binds to PAPD5 and/or PAPD7 polypeptide and inhibits propagation of HBV as a compound that ameliorates and/or inhibits a HBV infection.

3. The method of claim 1, wherein the PAPD5 polypeptide comprises:
   a. the amino acid sequence of SEQ ID NO: 1 or 2;
   b. an amino acid sequence having at least 80% identity to one of the amino acid sequence of (a), wherein the polypeptide has poly-A polymerase function;
   c. the amino acid sequence of an enzymatically active fragment of SEQ ID NO: 1 or 2; or
   d. an amino acid sequence having at least 80% identity to one of the amino acid sequence of (c), wherein the polypeptide has poly-A polymerase function.

4. The method of claim 1, wherein the PAPD7 polypeptide comprises:
   a. the amino acid sequence of SEQ ID NO: 3;
   b. an amino acid sequence having at least 80% identity to one of the amino acid sequence of (a), wherein the polypeptide has poly-A polymerase function;
   c. the amino acid sequence of an enzymatically active fragment of SEQ ID NO: 3; or
   d. an amino acid sequence having at least 80% identity to one of the amino acid sequence of (c), wherein the polypeptide has poly-A polymerase function.

5. The method of claim 2, wherein the compound that inhibits propagation of HBV, inhibits secretion of HBV surface antigen (HBsAg), and/or inhibits secretion of HBV envelope antigen (HBeAg), and/or inhibits production of intracellular HBV mRNA or HBV DNA.

6. The method of claim 1, wherein the activity of PAPD5 and PAPD7 is a poly-A polymerase function.

7. The method of claim 2, wherein the PAPD5 polypeptide comprises:
   a. the amino acid sequence of SEQ ID NO: 1 or 2;
   b. an amino acid sequence having at least 80% identity to one of the amino acid sequence of (a), wherein the polypeptide has poly-A polymerase function;
   c. the amino acid sequence of an enzymatically active fragment of SEQ ID NO: 1 or 2; or
   d. an amino acid sequence having at least 80% identity to one of amino acid sequence of (c), wherein the polypeptide has poly-A polymerase function.

8. The method of claim 2, wherein the PAPD7 polypeptide comprises:
   a. the amino acid sequence of SEQ ID NO: 3;
   b. an amino acid sequence having at least 80% identity to one of the amino acid sequence of (a), wherein the polypeptide has poly-A polymerase function;
   c. the amino acid sequence of an enzymatically active fragment of SEQ ID NO: 3; or
   d. an amino acid sequence having at least 80% identity to one of the amino acid sequence of (c), wherein the polypeptide has poly-A polymerase function.

* * * * *